(12) United States Patent
Choi et al.

(10) Patent No.: US 10,756,277 B2
(45) Date of Patent: Aug. 25, 2020

(54) ORGANIC COMPOUND AND ORGANIC ELECTROLUMINESCENT DEVICE COMPRISING THE SAME

(71) Applicant: DOOSAN CORPORATION, Seoul (KR)

(72) Inventors: Tae Jin Choi, Seoul (KR); Ho-Cheol Park, Yongin-si (KR); Youngmi Beak, Yongin-si (KR); Eunjin Kim, Seoul (KR)

(73) Assignee: DOOSAN SOLUS CO., LTD., Iksan-si (KR)

( * ) Notice: Subject to any disclaimer, the term of this patent is extended or adjusted under 35 U.S.C. 154(b) by 0 days.

(21) Appl. No.: 15/302,301

(22) PCT Filed: Apr. 7, 2015

(86) PCT No.: PCT/KR2015/003473
§ 371 (c)(1),
(2) Date: Dec. 5, 2016

(87) PCT Pub. No.: WO2015/156580
PCT Pub. Date: Oct. 15, 2015

(65) Prior Publication Data
US 2017/0170406 A1  Jun. 15, 2017

(30) Foreign Application Priority Data
Apr. 9, 2014 (KR) .................... 10-2014-0042512

(51) Int. Cl.
| | | |
|---|---|---|
| H01L 51/00 | (2006.01) | |
| C09K 11/06 | (2006.01) | |
| C07D 491/04 | (2006.01) | |
| C07D 319/24 | (2006.01) | |
| C07D 493/04 | (2006.01) | |
| C07D 495/04 | (2006.01) | |
| C07D 491/056 | (2006.01) | |
| H01L 51/50 | (2006.01) | |

(52) U.S. Cl.
CPC ........ *H01L 51/0071* (2013.01); *C07D 319/24* (2013.01); *C07D 491/04* (2013.01); *C07D 491/056* (2013.01); *C07D 493/04* (2013.01); *C07D 495/04* (2013.01); *C09K 11/06* (2013.01); *H01L 51/006* (2013.01); *H01L 51/0059* (2013.01); *H01L 51/0061* (2013.01); *H01L 51/0067* (2013.01); *H01L 51/0072* (2013.01); *H01L 51/0074* (2013.01); *C09K 2211/1007* (2013.01); *C09K 2211/1011* (2013.01); *C09K 2211/1014* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/0052* (2013.01); *H01L 51/0054* (2013.01); *H01L 51/0058* (2013.01); *H01L 51/0065* (2013.01); *H01L 51/0068* (2013.01); *H01L 51/0069* (2013.01); *H01L 51/0081* (2013.01); *H01L 51/0085* (2013.01); *H01L 51/5012* (2013.01); *H01L 51/5016* (2013.01); *H01L 51/5056* (2013.01); *H01L 51/5072* (2013.01)

(58) Field of Classification Search
None
See application file for complete search history.

(56) References Cited

FOREIGN PATENT DOCUMENTS

| | | | | |
|---|---|---|---|---|
| JP | 2007217339 A | * | 8/2007 | |
| KR | 10-2009-0041040 A | | 4/2009 | |
| KR | 10-2011-0018688 A | | 2/2011 | |
| KR | 10-2014-0103391 A | | 8/2014 | |
| KR | 10-2014-0142021 A | | 12/2014 | |
| WO | WO-2004/037831 A1 | * | 5/2004 | .......... C07D 487/04 |
| WO | WO-2011/021803 A2 | * | 2/2011 | |
| WO | WO-2014/051232 A1 | * | 4/2014 | |

OTHER PUBLICATIONS

Machine English translation of KR 10-2011-0018688. Translated Mar. 1, 2018.*
Machine English translation of Ryu et al. (WO 2014/051232 A1). Aug. 9, 2018.*
Machine English translation of Sugiura et al. (JP 2007-217339 A). Sep. 7, 2019.*
Maloney et al. (Environ. Sci. Technol. 1986, 20, p. 249).*
International Searching Authority, International Search Report for PCT/KR2015/003473 dated Sep. 9, 2015 [PCT/ISA/210].

* cited by examiner

*Primary Examiner* — Jay Yang
(74) *Attorney, Agent, or Firm* — Sughrue Mion, PLLC

(57) ABSTRACT

The present disclosure relates to a novel organic compound and an organic electroluminescent device comprising the same, and the organic compound of the present disclosure may be used for an organic material layer of the organic electroluminescent device, thereby improving the light emitting efficiency, driving voltage, lifetime, and the like of the organic electroluminescent device.

17 Claims, No Drawings

ORGANIC COMPOUND AND ORGANIC ELECTROLUMINESCENT DEVICE COMPRISING THE SAME

CROSS REFERENCE TO RELATED APPLICATIONS

This application is a National Stage of International Application No. PCT/KR2015/0034734, filed on Apr. 7, 2015, which claims priority from Korean Patent Application No. 10-2014-0042512, filed on Apr. 9, 2014, the contents of all of which are incorporated herein by reference in their entirety.

TECHNICAL FIELD

The present disclosure relates to a novel organic compound and an organic electroluminescent device comprising the same.

BACKGROUND ART

Since 1965, studies on an organic electroluminescent (EL) device (hereinafter, simply referred to as an 'organic EL device') leading to blue electric light emission using an anthracene single crystal had been continuously conducted, and in 1987, an organic EL device having a two-layer laminated structure including a hole layer (NPB) and a light emitting layer ($Alq_3$) was proposed by Tang. Since then, the organic EL device has been proposed in the form of a multilayer-laminated structure which imparts each characteristic and subdivided function, such as an organic layer which is responsible for injecting and transporting holes, an organic layer which is responsible for injecting and transporting electrons, and an organic layer which induces electroluminescence to occur due to the combination of holes and electrons in the device in order to implement high efficiency and long lifetime characteristics required for commercialization.

In the organic EL device, when voltage is applied between two electrodes, holes are injected into the organic material layer at the anode, and electrons are injected into the organic material layer at the cathode. When the injected holes and electrons meet each other, an exciton is formed, and when the exciton falls down to a bottom state, light is emitted. Materials included in the organic material layer may be classified into a light emitting material, a hole injection material, a hole transporting material, an electron transporting material, an electron injection material, and the like according to the function.

In the electron spins of the excitons formed by recombining electrons and holes, the singlet exciton and the triplet exciton are produced at a ratio of 25% and 75%, respectively. In this case, the organic EL device may be classified into a fluorescent EL device in which singlet excitons contribute to light emission and a phosphorescent EL device in which triplet excitons contribute to light emission, according to the type of electron spin of the excitons formed.

In the fluorescent EL device in which light is emitted by singlet excitons, it is impossible for the internal quantum efficiency to theoretically exceed 25% according to the production ratio, and the external quantum efficiency of 5% is accepted as the limitation.

In the phosphorescent EL device in which light is emitted by triplet excitons, when a metal complex compound including a transition metal heavy atom such as Jr and Pt is used as a phosphorescent dopant, the light emitting efficiency may be improved up to 4 times compared to the fluorescent electroluminescent device.

As described above, the phosphorescent EL device exhibits theoretically higher efficiency than that of the fluorescent EL device in terms of light emitting efficiency. However, unlike green or red phosphorescent devices, in blue phosphorescent devices, the level of development for the color purity of a dark blue color, a phosphorescent dopant with high efficiency, and a host with a wide energy gap has been so little that commercialization has not even started, and instead, a blue fluorescent device has been used in products.

As the performance of the organic EL device has been improved to the level of commercialization characteristics due to the introduction of a multilayer-laminated structure, it has been attempted to expand the application range of the organic EL device from the start of a radio display product for a vehicle since 1997 to a mobile information display device and a display device for TV.

Further, according to the recent trends of an increase in size and a high resolution in a display, there is a need for developing an organic EL display having high efficiency and a long lifetime. In particular, the high resolution in a display may be implemented when more pixels are formed in the same area. Due to the high resolution, the light emitting area of the organic EL pixels has decreased, thereby resulting in reduction in the lifetime of the device. This reduction in the lifetime of the device has become the most important technical problem that the organic EL device needs to overcome.

However, since the materials for the organic EL device in the related art have a low glass transition temperature and thus are very poor in thermal stability, the materials fail to reach a level which is satisfactory in terms of a lifetime of an organic EL device, and need to be improved even in terms of light emitting characteristics.

DISCLOSURE

Technical Problem

Therefore, an object of the present disclosure is to provide a novel compound which has excellent carrier transporting capability and light emitting capability, and the like, and thus may be used as a material of light emitting layer, a material of hole transport layer, a material of light emitting auxiliary layer, a material of electron transport auxiliary layer, and the like.

Further, another object of the present disclosure is to provide an organic electroluminescent device which includes the novel compound to have a low driving voltage, high light emitting efficiency, and an improved lifetime.

Technical Solution

The present disclosure provides a compound represented by the following Formula 1:

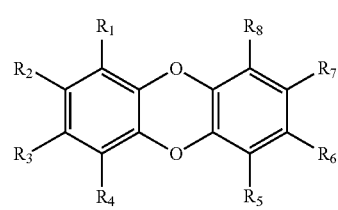

[Formula 1]

in Formula 1,
one of $R_1$ and $R_2$, $R_2$ and $R_3$, $R_3$ and $R_4$, $R_4$ and $R_5$, $R_5$ and $R_6$, $R_6$ and $R_7$, and $R_7$ and $R_8$ combines with each other to form a fused ring represented by the following Formula 2;

[Formula 2]

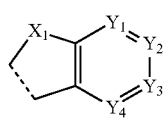

in Formula 2,
a dotted line is a portion to be bonded to Formula 1,
$X_1$ is selected from the group consisting of $N(Ar_1)$, O, S, $C(Ar_2)(Ar_3)$, and $Si(Ar_4)(Ar_5)$,
$Y_1$ to $Y_4$ are each independently N or $C(R_9)$,
$Ar_1$ to $Ar_5$ are the same as or different from each other, and are each independently selected from the group consisting of a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring,
$R_1$ to $R_8$, which do not form the fused ring of Formula 2, and $R_9$ are the same as or different from each other, and are each independently selected from the group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring, and
the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ and $R_1$ to $R_9$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, the substituent may combine with an adjacent group to form a fused ring, and when the substituent is present in plural numbers, the substituents are the same as or different from each other.

Further, the present disclosure provides an organic electroluminescent device including an anode, a cathode, and one or more organic material layers interposed between the anode and the cathode, in which at least one of the organic material layers comprises the above-described compound represented by Formula 1.

Advantageous Effects

The compound of the present disclosure has excellent thermal stability, carrier transporting capability, light emitting capability, and the like, and thus may be usefully applied as a material of organic material layer for an organic electroluminescent device.

Further, for the organic electroluminescent device including the compound of the present disclosure in an organic material layer, the aspects such as light emitting performance, driving voltage, lifetime, and efficiency may be significantly improved, and accordingly, the organic electroluminescent device may be effectively applied to a full-color display panel, and the like.

BEST MODE

Hereinafter, the present disclosure will be described.

In the organic compound according to the present disclosure, an indole moiety, a benzothiophene moiety, a benzofuran moiety, or the like is fused with dibenzo[b,e][1,4]dioxine to form a basic skeleton, and the organic compound has a structure in which various substituents are bonded to or fused with the basic skeleton, and is represented by Formula 1.

In general, the phosphorescent light emitting layer in the organic material layers included in the organic electroluminescent device includes a host and a dopant in order to increase the color purity and the light emitting efficiency. In this case, the host needs to have a higher triplet energy gap than that of the dopant. That is, in order to effectively provide a phosphorescent light emission from the dopant, the lowest excitation state energy of the host needs to be higher than the lowest emission state energy of the dopant. The compound represented by Formula 1 has a wide singlet energy level and a high triplet energy level in which the dibenzo[b,e][1,4]dioxine portion. A specific substituent may be introduced into the indole moiety which is fused with dibenzo[b,e][1,4]dioxine to exhibit a higher energy level than that of the dopant when the compound of Formula 1 is applied as a host of the light emitting layer.

Further, since the compound represented by Formula 1 has a high triplet energy as described above, it is possible to prevent diffusing (moving) an exciton produced from a light emitting layer to an adjacent electron transport layer or an adjacent hole transport layer. Accordingly, when the compound of Formula 1 is used to form an organic material layer (hereinafter, referred to as a 'light emitting auxiliary layer') between a hole transport layer and a light emitting layer or form an organic material layer (hereinafter, referred to as an 'electron transport auxiliary layer') between a light emitting layer and an electron transport layer, the diffusion of excitons is prevented by the compound, so that the number of excitons substantially contributing to light emission in the light emitting layer is increased, and thus the light emitting efficiency of the device may be improved, unlike an organic electroluminescent device in the related art, which does not include the light emitting auxiliary layer or the electron transport auxiliary layer.

Further, the compound represented by Formula 1 may have a wide bandgap and high carrier transporting property because the HOMO and LUMO energy levels may be adjusted according to the substituent to be introduced into the basic skeleton.

Additionally, the compound of the present disclosure may be easily used as a material of hole transport layer when an electron donating group (EDG) having a high electron donating property is bonded to the basic skeleton due to high hole transporting capability of an oxygen atom in the dibenzo[b,e][1,4]dioxine. Further, when an electron withdrawing group (EWG) having a high electron absorbing property is bonded to the basic skeleton, the entire molecule has bipolar characteristics, and thus may increase the binding power of holes and electrons.

Furthermore, according to the compound represented by Formula 1 of the present disclosure, the molecular weight of the compound is significantly increased as various substitution products, particularly, an aryl group and/or a heteroaryl group, are introduced into the basic skeleton, and accordingly, the glass transition temperature is enhanced, so that the compound represented by Formula 1 of the present disclosure may have thermal stability higher than that of the organic material layer material in the related art (for example, CBP). Further, the compound represented by Formula 1 is also effective for suppressing crystallization of the organic material layer.

As described above, when the compound represented by Formula 1 of the present disclosure is applied as a material of organic material layer material for an organic electroluminescent device, preferably a material of light emitting layer (a blue, green, and/or red phosphorescent host material), a material of electron transport layer/injection layer, a material of hole transport layer/injection layer, a material of light emitting auxiliary layer, and a material of lifetime improvement layer, the performance and lifetime characteristics of the organic electroluminescent device may be greatly enhanced. The organic electroluminescent device may resultantly maximize the performance of a full-color organic light emitting panel.

When one of $R_1$ and $R_2$, $R_2$ and $R_3$, $R_3$ and $R_4$, $R_4$ and $R_5$, $R_5$ and $R_6$, $R_6$ and $R_7$, and $R_7$ and $R_8$ combines with each other to form a fused ring represented by the following Formula 2, the compound of Formula 1 may be represented by any one selected from the following Formulae 3 to 5.

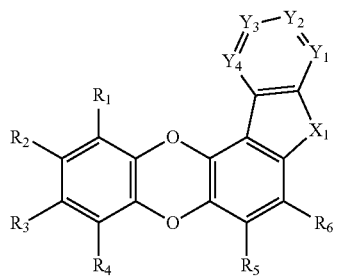

[Formula 3]

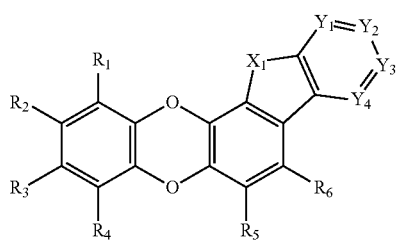

[Formula 4]

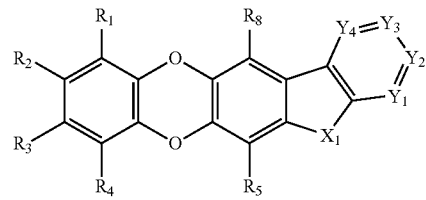

[Formula 5]

In Formulae 3 to 5, $X_1$, $Y_1$ to $Y_4$, and $R_1$ to $R_8$ are each the same as those defined in Formula 1.

The $R_1$ to $R_8$, which do not form the fused ring of Formula 2, are the same as or different from each other, and are each independently selected from a group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring.

In Formula 2, a dotted line means a portion bonded to Formula 1.

The $X_1$ is selected from a group consisting of $N(Ar_1)$, O, S, $C(Ar_2)(Ar_3)$, and $Si(Ar_4)(Ar_5)$, and may be preferably selected from a group consisting of $N(Ar_1)$, O, and S.

The $Ar_1$ to $Ar_5$ are the same as or different from each other, and are each independently selected from a group consisting of a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring.

Preferably, the $Ar_1$ to $Ar_5$ are the same as or different from each other, and may be each independently selected from a group consisting of a $C_6$ to $C_{60}$ aryl group and a heteroaryl group having 5 to 60 nuclear atoms.

The $Y_1$ to $Y_4$ are each independently N or $C(R_9)$, and may be all preferably $C(R_9)$. In this case, when $C(R_9)$ is present in plural numbers, a plurality of $C(R_9)$'s is the same as or different from each other.

The $R_9$ is selected from a group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring.

Preferably, the $R_9$ may be selected from a group consisting of hydrogen, deuterium (D), a $C_6$ to $C_{60}$ aryl group, a heteroaryl group having 5 to 60 nuclear atoms, and a $C_6$ to $C_{60}$ arylamine group.

The alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$, $R_1$ to $R_8$, which do not form the fused ring of Formula 2, and $R_9$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and the substituent may combine with an adjacent group to form a fused ring. In this case, when the substituent is present in plural numbers, a plurality of substituents is the same as or different from each other.

Alternatively, at least one of the $Ar_1$ to $Ar_5$, $R_1$ to $R_8$, which do not form the fused ring of Formula 2, and $R_9$ preferably at least one of the $Ar_1$ to $Ar_5$ and $R_9$ may be a substitution product represented by the following Formula 6.

[Formula 6]

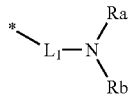

In Formula 6, $L_1$ is a single bond (direct bond), or selected from a group consisting of a $C_6$ to $C_{18}$ arylene group and a heteroarylene group having 5 to 18 nuclear atoms, or may combine with an adjacent substituent (for example, $R_a$, $R_b$) to form a fused ring, $R_a$ and $R_b$ are the same as or different from each other, and are each independently a substitution product selected from a group consisting of a $C_1$ to $C_{40}$ alkyl group, a $C_6$ to $C_{60}$ aryl group, and a heteroaryl group having 5 to 60 nuclear atoms, or represented by the following Formula 7 or 8, or may combine with an adjacent substituent (for example, $L_1$) to form a fused ring,

[Formula 7]

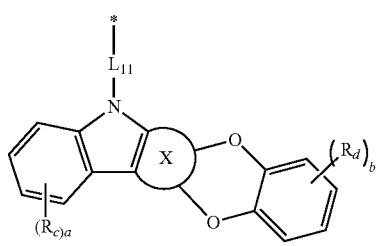

-continued

[Formula 8]

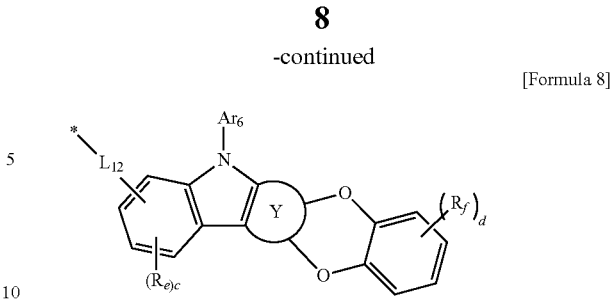

in Formulae 7 and 8,

X and Y are each a 6-membered aromatic ring, $L_{11}$ and $L_{12}$ are each a single bond, or selected from a group consisting of a $C_6$ to $C_{18}$ arylene group and a heteroarylene group having 5 to 18 nuclear atoms, $Ar_6$ is selected from a group consisting of a $C_6$ to $C_{18}$ aryl group and a heteroaryl group having 5 to 18 nuclear atoms, a, b, and d are each an integer of 0 to 4, and the case where the a, b, and d are 0 means that hydrogen is not substituted with the substituent $R_c$, $R_d$, or $R_f$, and when the a, b, and d are each an integer of 1 to 3, $R_c$, $R_d$, and $R_f$ are each selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, c is an integer of 0 to 3, and the case where the c is 0 means that hydrogen is not substituted with the substituent $R_c$, and when the c is 1 to 3, $R_c$ is selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, in this case, a plurality of $R_c$'s is the same as or different from each other, a plurality of $R_d$'s is the same as or different from each other, a plurality of $R_e$'s is the same as or different from each other, and a plurality of $R_f$'s is the same as or different from each other, and the arylene group and the heteroarylene group of $L_1$ and the alkyl group, the aryl group, and the heteroaryl group of $R_a$ and $R_b$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

Further, at least one of the $Ar_1$ to $Ar_5$, $R_1$ to $R_8$, which do not form the fused ring of Formula 2, and $R_9$ preferably at least one of the $Ar_1$ to $Ar_5$ and $R_9$ may be a substitution product represented by the following Formula 9.

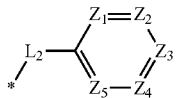

[Formula 9]

In Formula 9, $L_2$ is a single bond (direct bond) or selected from a group consisting of a $C_6$ to $C_{18}$ arylene group and a heteroarylene group having 5 to 18 nuclear atoms, $Z_1$ to $Z_5$ are the same as or different from each other, and are each independently N or $C(R_{11})$, in this case, at least one of $Z_1$ to $Z_5$ is N, when $C(R_{11})$ is present in plural numbers, a plurality of $C(R_{11})$'s is the same as or different from each other, $R_{11}$ is selected from a group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or may combine with an adjacent group to form a fused ring, and the arylene group and the heteroarylene group of $L_2$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{11}$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

Further, at least one of the $Ar_1$ to $Ar_5$, $R_1$ to $R_8$, which do not form the fused ring of Formula 2, and $R_9$ preferably at least one of the $Ar_1$ to $Ar_5$ and $R_9$ may be selected from a group consisting of substituents represented by the following Formulae A-1 to A-15.

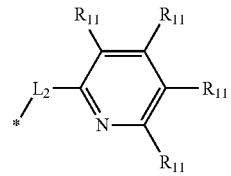

A-1

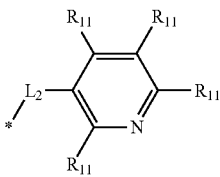

A-2

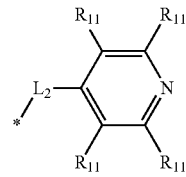

A-3

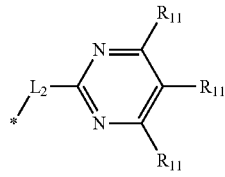

A-4

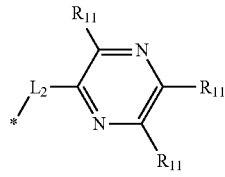

A-5

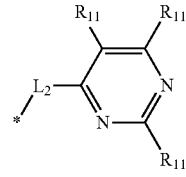

A-6

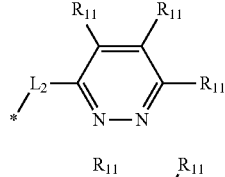

A-7

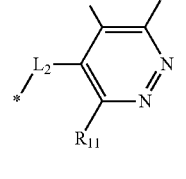

A-8

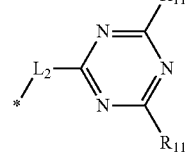

A-9

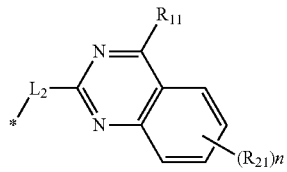

A-10

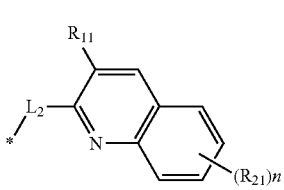

A-11

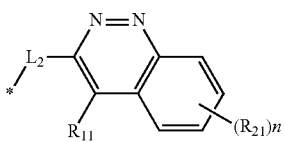

A-12

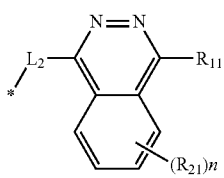

A-13

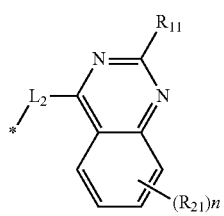

A-14

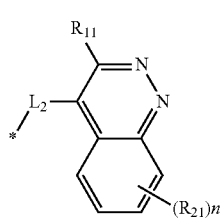

A-15

In Formulae A-1 to A-15, $L_2$ and $L_{11}$ are each the same as those defined in Formula 9, n is an integer of 0 to 4, and the case where the n is 0 means that hydrogen is not substituted with the substituent $R_{21}$, and when the n is an integer of 1 to 4, $R_{21}$ is selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or may combine with an adjacent group to form a fused ring, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the arylsilyl group, the alkylboron group, the arylboron group, the arylphosphine group, the arylphosphine oxide group, and the arylsilyl group of $R_{21}$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

Further, at least one of the $Ar_1$ to $Ar_5$, $R_1$ to $R_8$, which do not form the fused ring of Formula 2, and $R_9$ preferably at least one of the $Ar_1$ to $Ar_5$ and $R_9$ may be a substitution product represented by the following Formula 10 or 11.

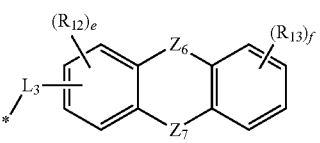

[Formula 10]

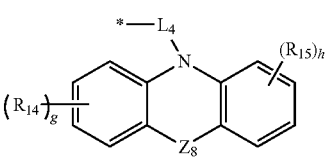

[Formula 11]

In Formulae 10 and 11, $L_3$ and $L_4$ are each a single bond (direct bond), or selected from a group consisting of a $C_6$ to $C_{18}$ arylene group and a heteroarylene group having 5 to 18 nuclear atoms, $Z_6$ to $Z_8$ are the same as or different from each other, and are each independently a single bond, or O, S, or $N(R_{16})$, provided that a case where $Z_6$ and $Z_7$ are all a single bond is excluded, in this case, when $N(R_{16})$ is present in plural numbers, a plurality of $N(R_{16})$'s is the same as or different from each other, $R_{16}$ is selected from a group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or may combine with an adjacent group to form a fused ring, e is an integer of 0 to 3, and when the e is 1 to 3, $R_{12}$ is selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, f, g, and h are an integer of 0 to 4, and when the f, g, and h are each an integer of 1 to 4, $R_{13}$ to $R_{15}$ are selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, and in this case, the arylene group and the heteroarylene group of $L_3$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{12}$ to $R_{16}$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

In Formula 1, the $X_1$ may be $N(Ar_1)$. In this case, the $Ar_1$ is the same as that defined in Formula 1, and may be preferably a substitution product represented by the following Formula 12:

[Formula 12]

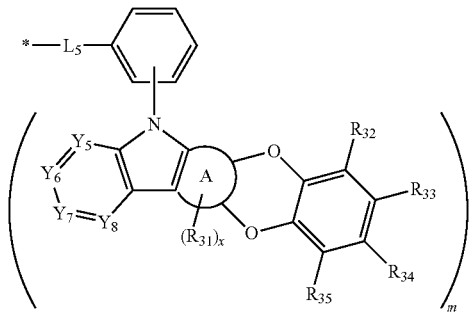

in Formula 12, $L_5$ is a single bond, or selected from a group consisting of a $C_6$ to $C_{60}$ aryl group, m is an integer of 1 and 2, A is a 6-membered aromatic ring, x is an integer of 0 to 2, and when the x is an integer of 1 and 2, $R_{31}$ are selected from a group consisting of deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring, and in this case, when the $R_{31}$ is present in plural numbers, a plurality of $R_{31}$'s is the same as or different from each other, $Y_5$ to $Y_8$ are each independently N or $C(R_{36})$, and in this case, when the $C(R_{36})$ is present in plural numbers, a plurality of $C(R_{36})$'s is the same as or different from each other, $R_{32}$ to $R_{36}$ are the same as or different from each other, and are each independently selected from a group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or may combine with an adjacent group to form a fused ring, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_{31}$ to $R_{36}$ are each independently unsubstituted or substituted with one or more substituents selected from a group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, the substituent may combine with an adjacent group to form a fused ring, and in this case, when the substituent is present in plural numbers, the substituents are the same as or different from each other.

Specifically, the substitution product represented by Formula 12 may be a substitution product represented by any one of the following Formulae 13 to 15.

[Formula 13]

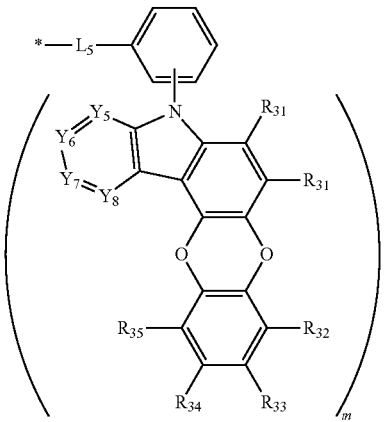

15
-continued
[Formula 14]
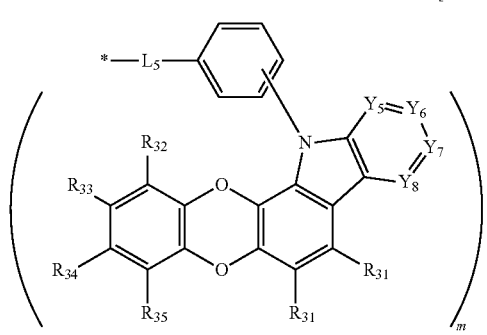
16
-continued
[Formula 15]
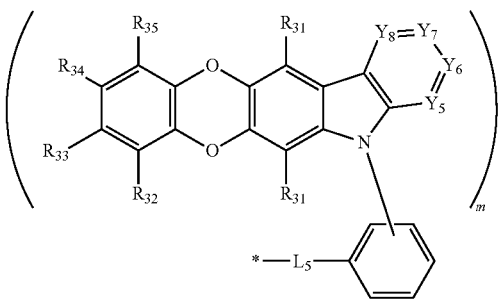
In Formulae 13 to 15,
$L_4$, $Y_5$ to $Y_8$, and $R_{31}$ to $R_{35}$ are each the same as those defined in Formula 12.
The compound of Formula 1 according to the present disclosure may be embodied as the following exemplified compounds, but is not limited thereto.
Cpd 1
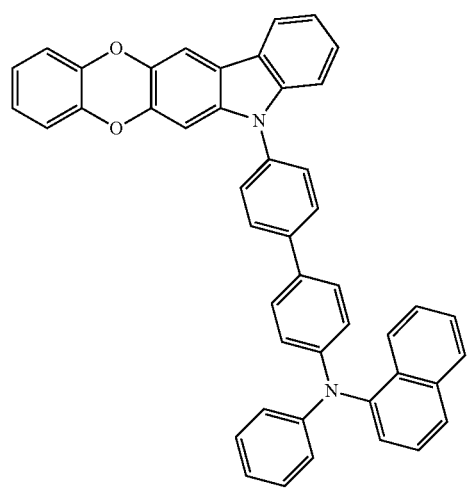
Cpd 2
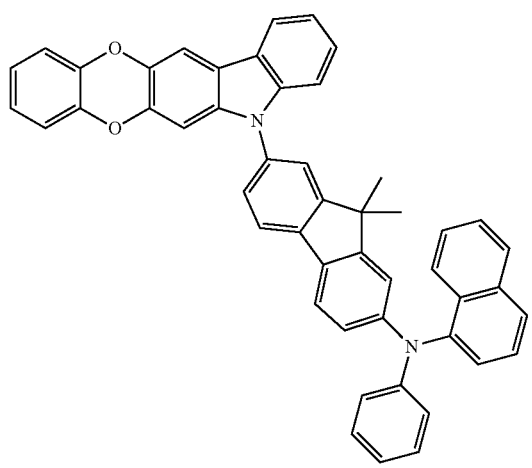
Cpd 3
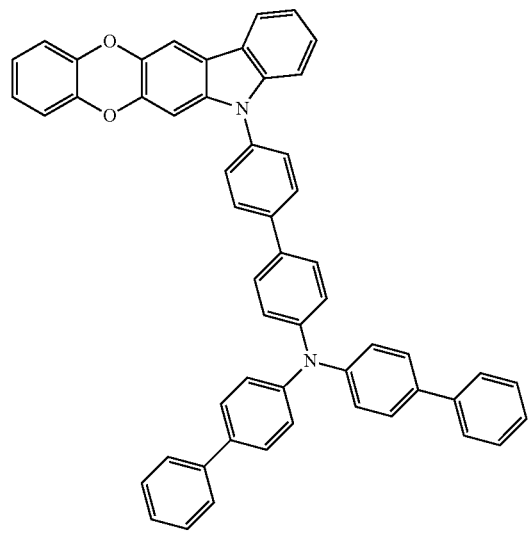
Cpd 4
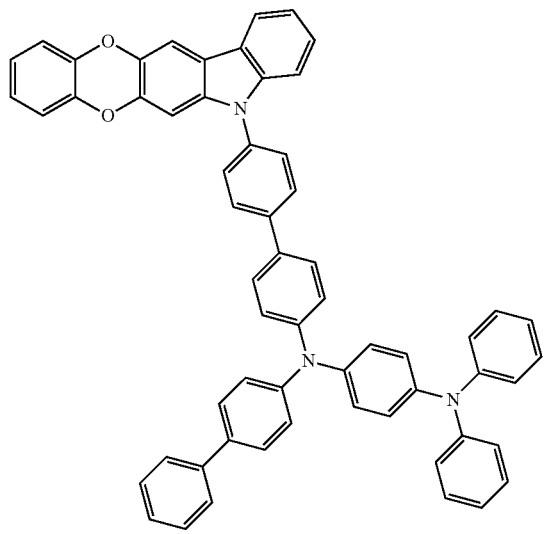

-continued
Cpd 5
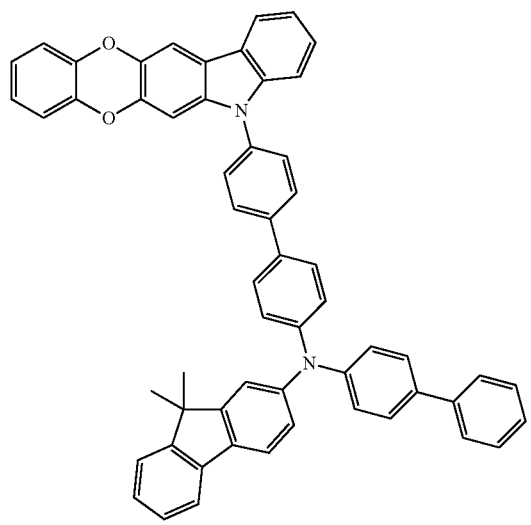
Cpd 6
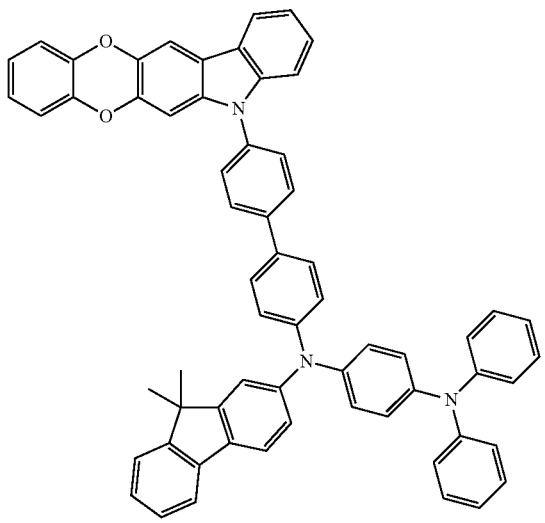
Cpd 7
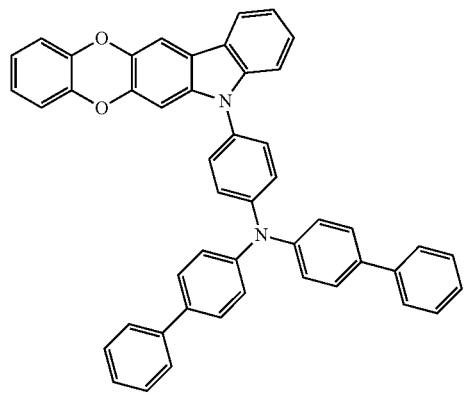
Cpd 8
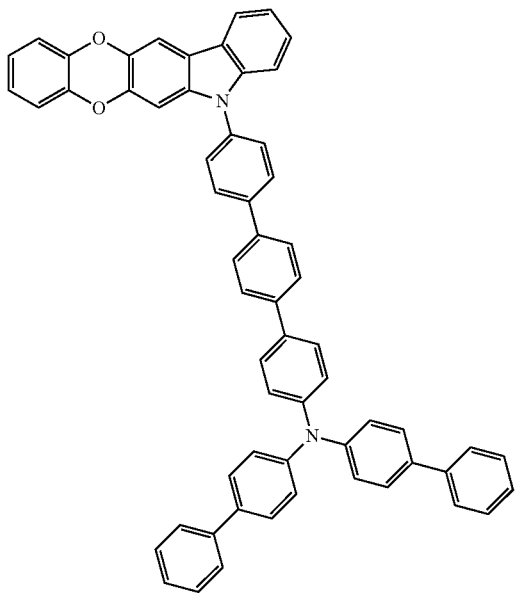

-continued
Cpd 9
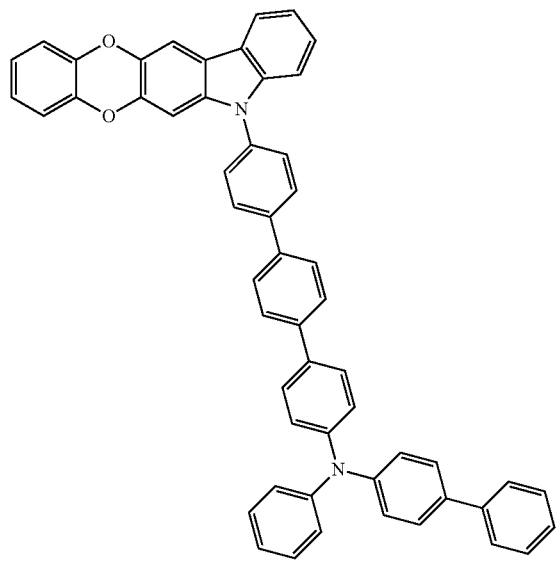
Cpd 10
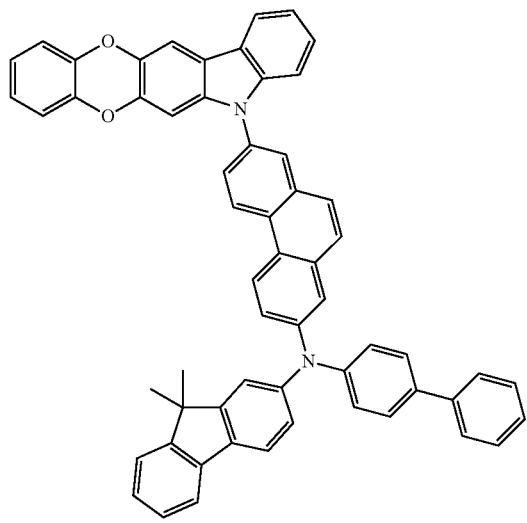
Cpd 11
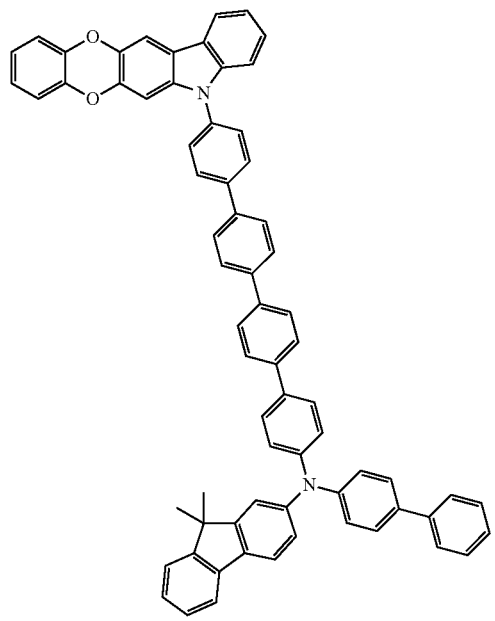
Cpd 12
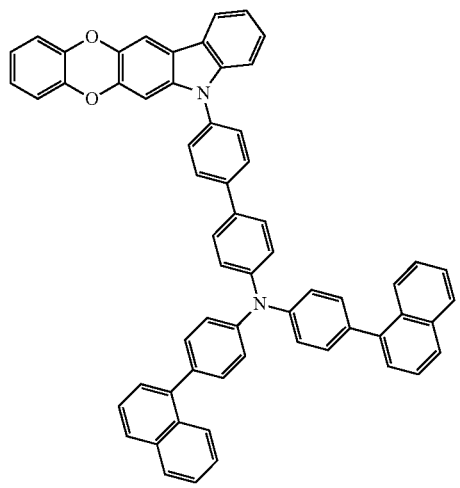

-continued
Cpd 13
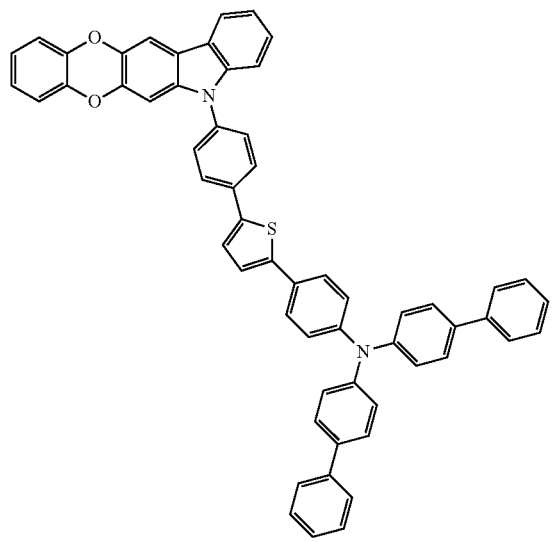
Cpd 14
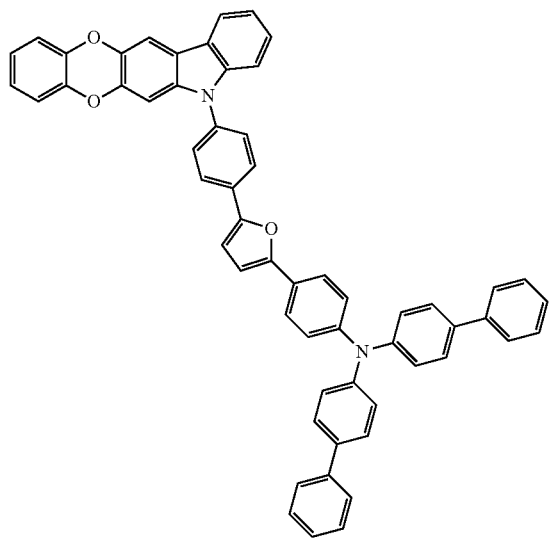
Cpd 15
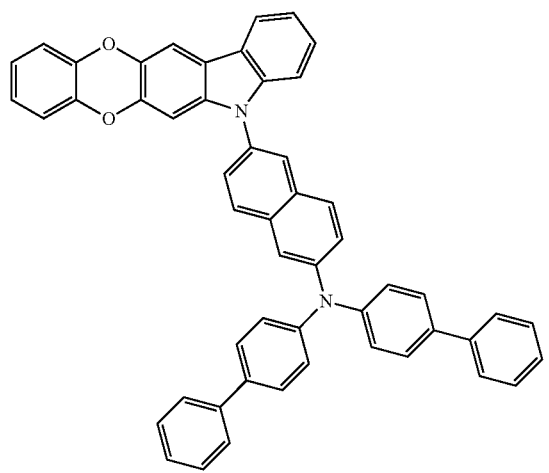
Cpd 16
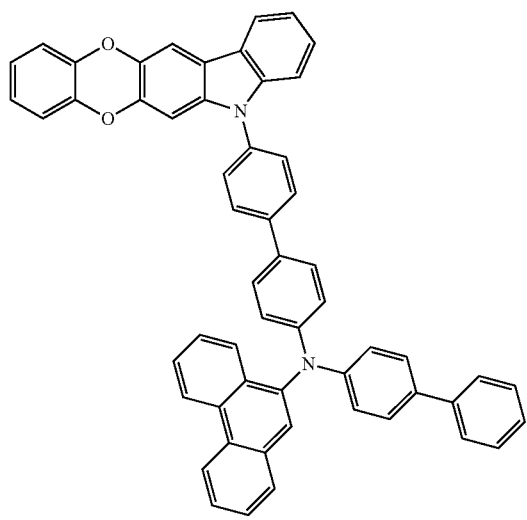

-continued
Cpd 17
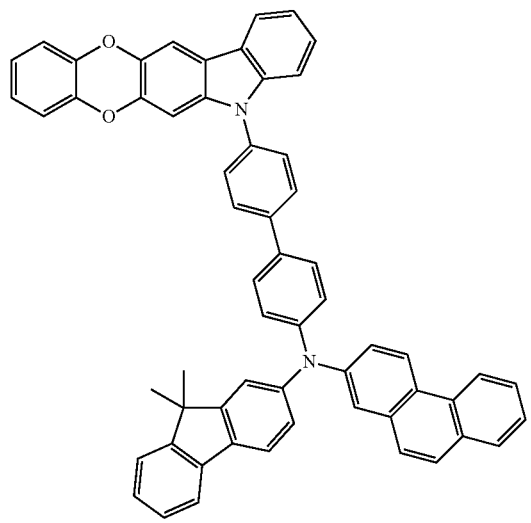
Cpd 18
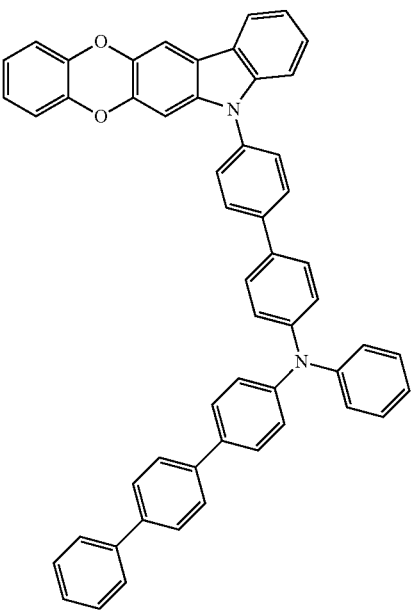
Cpd 19
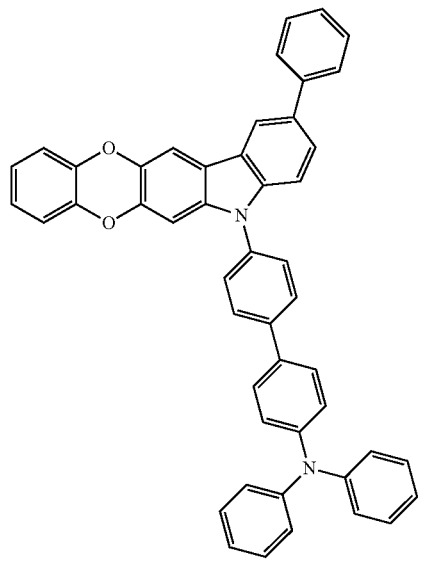
Cpd 20
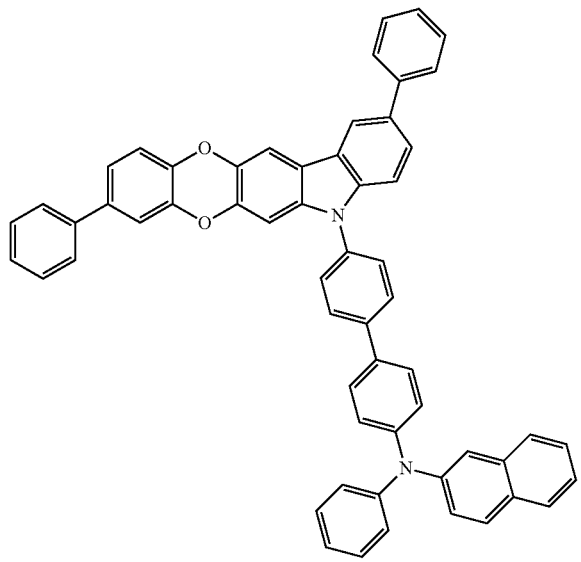

-continued
Cpd 21
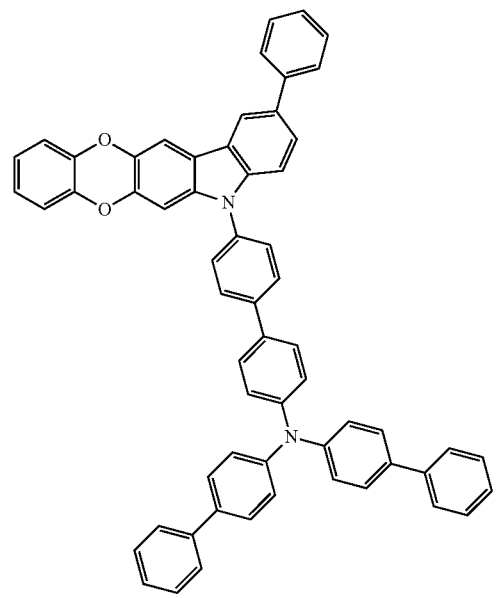
Cpd 22
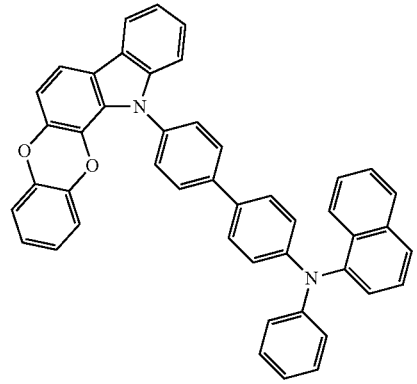
Cpd 23
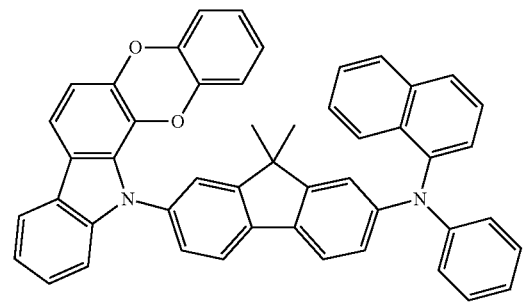
Cpd 24
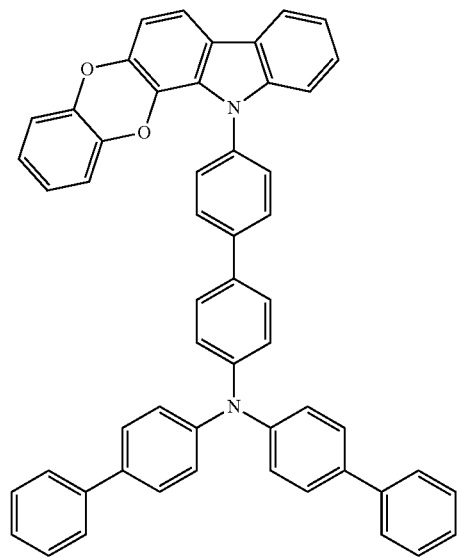

-continued
Cpd 25
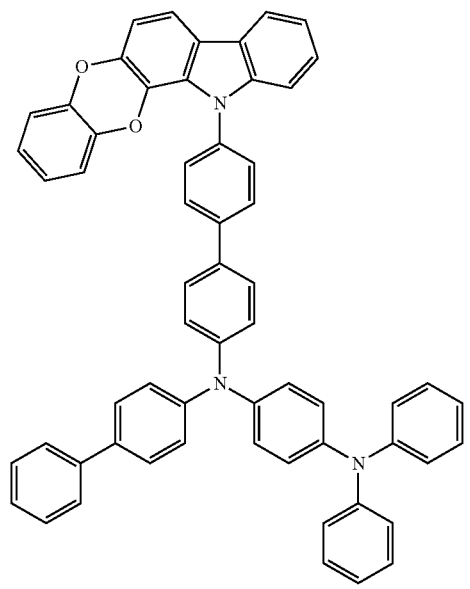
Cpd 26
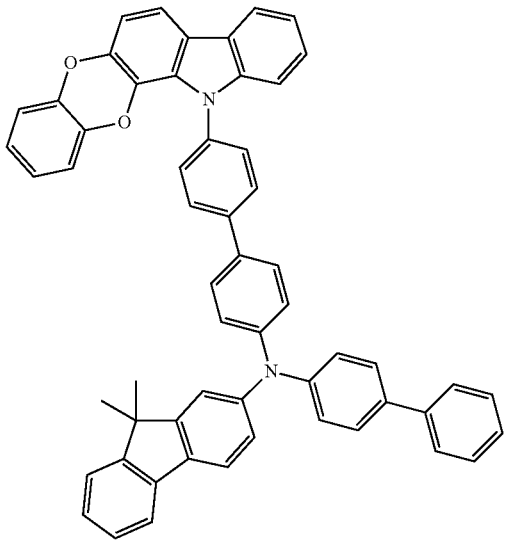
Cpd 27
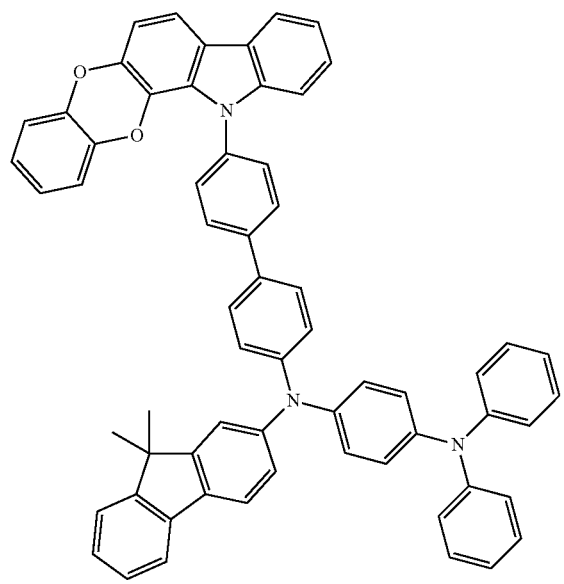
Cpd 28
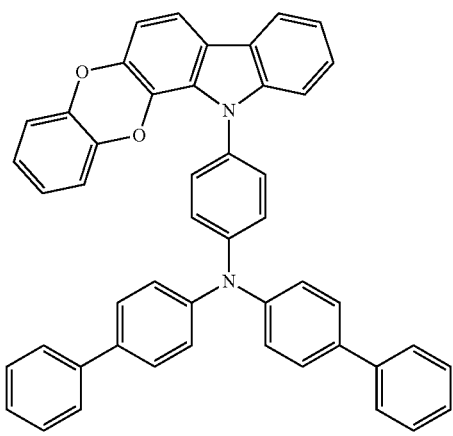

-continued
Cpd 29
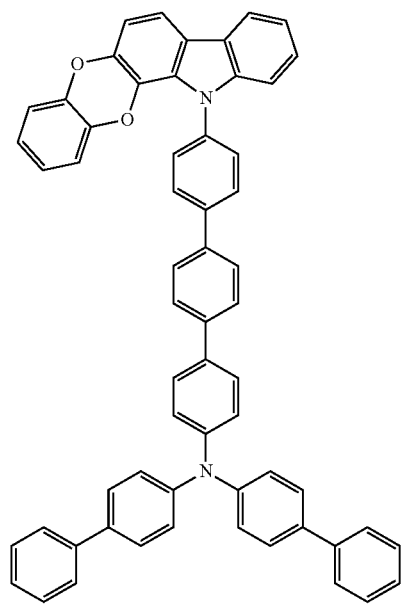
Cpd 30
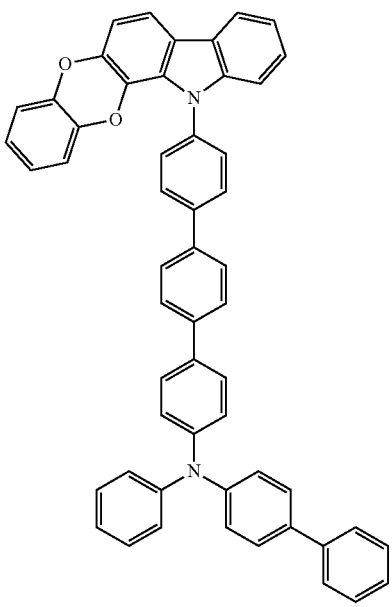
Cpd 31
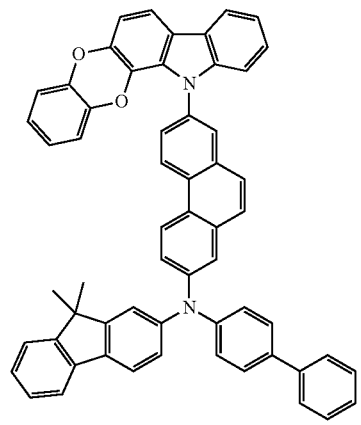
Cpd 32
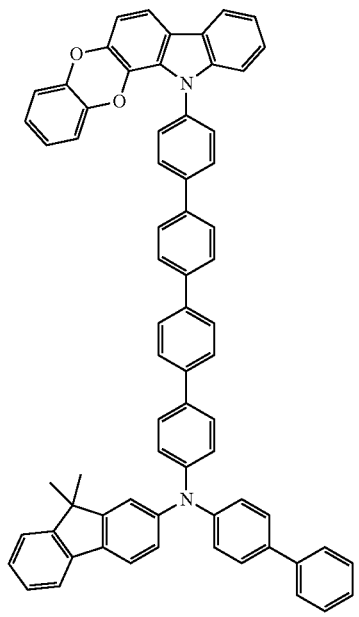

-continued
Cpd 33
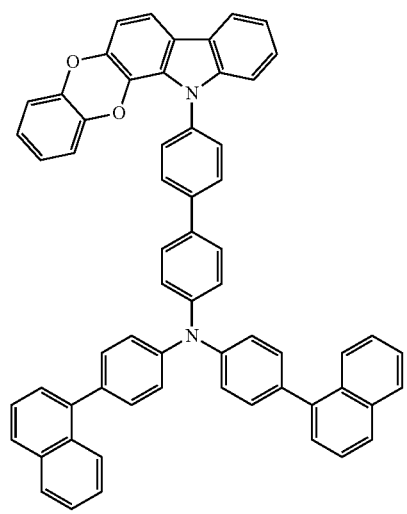
Cpd 34
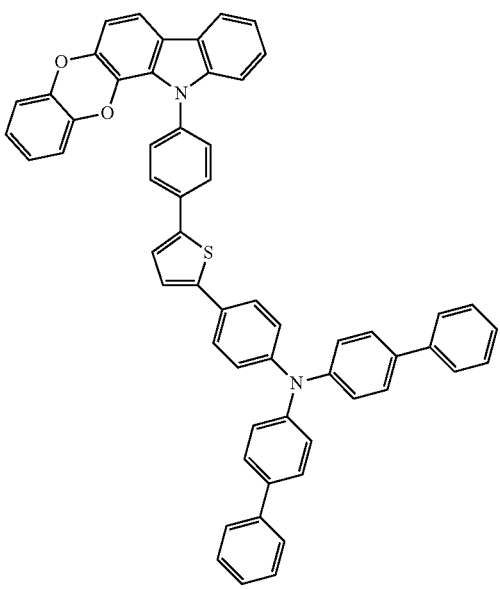
Cpd 35
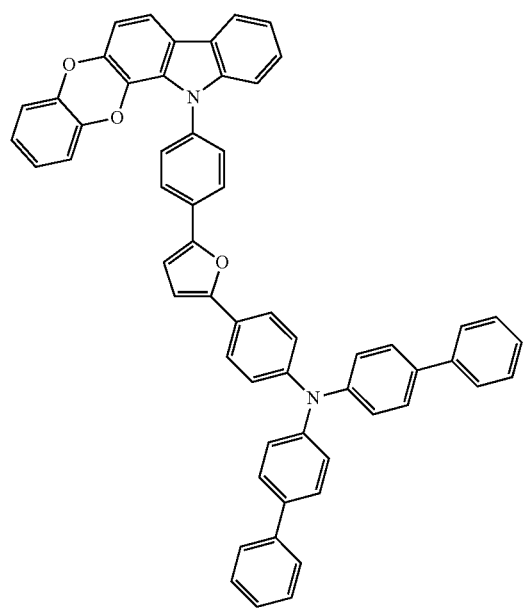
Cpd 36
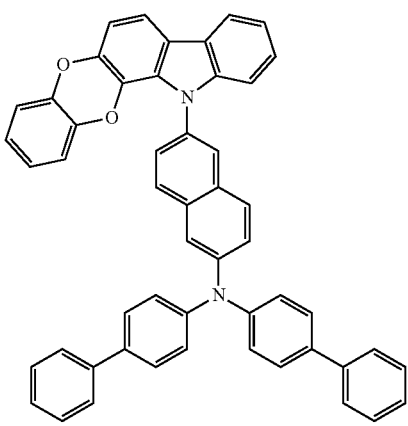

Cpd 37
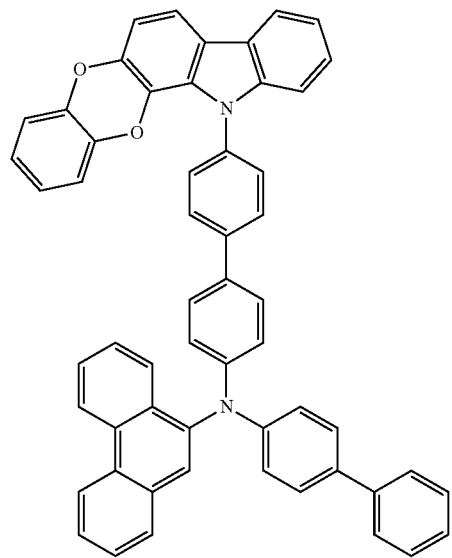
Cpd 38
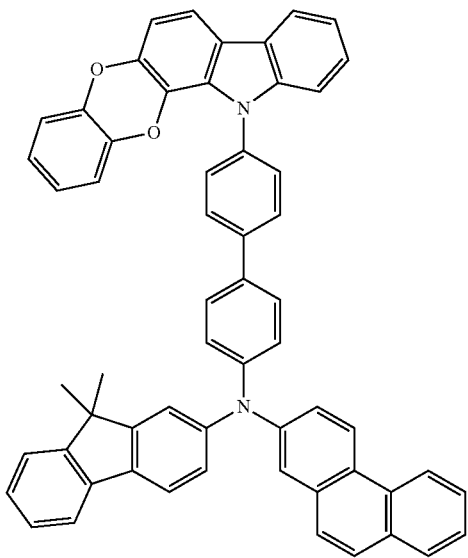
Cpd 39
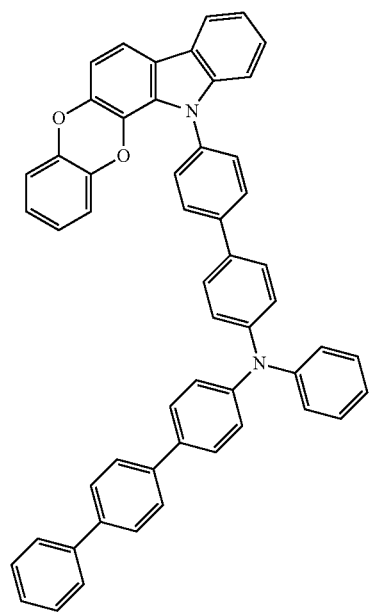
Cpd 40

-continued
Cpd 41
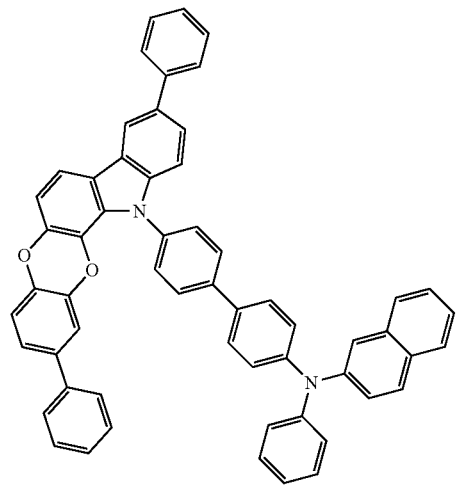
Cpd 42
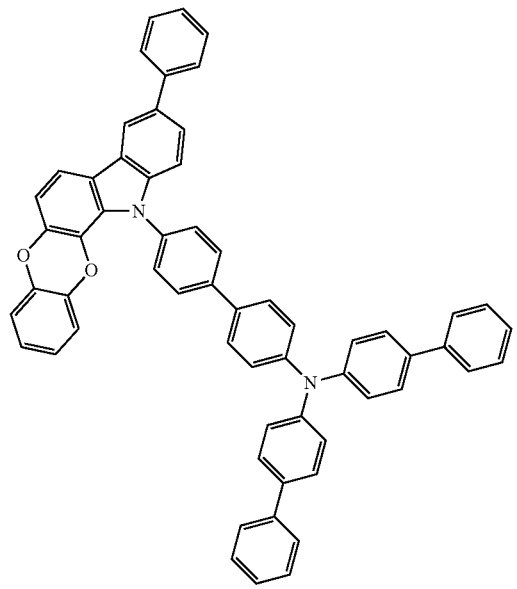
Cpd 43
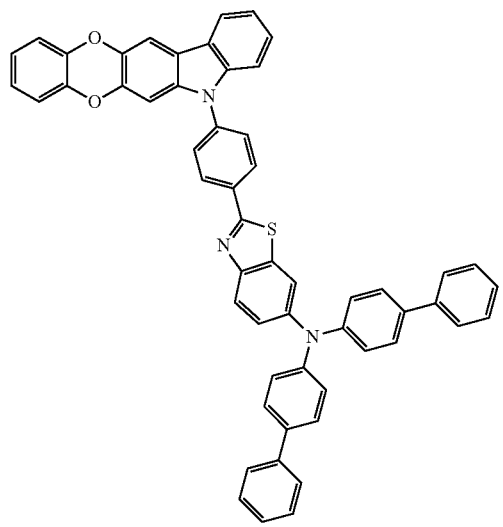
Cpd 44
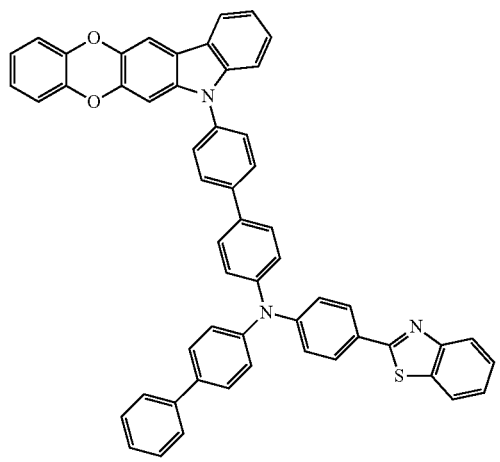

-continued
Cpd 45
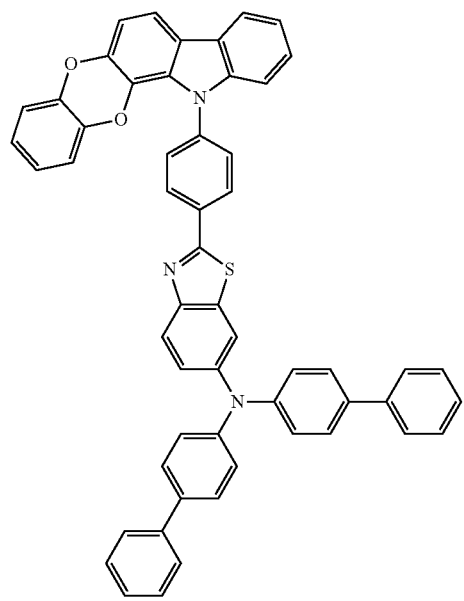
Cpd 46
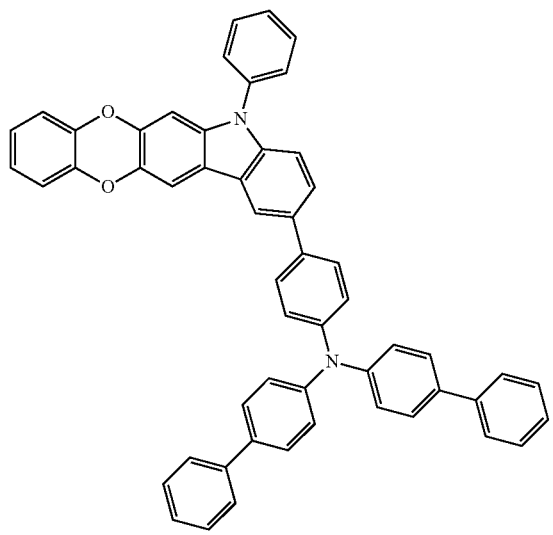
Cpd 47
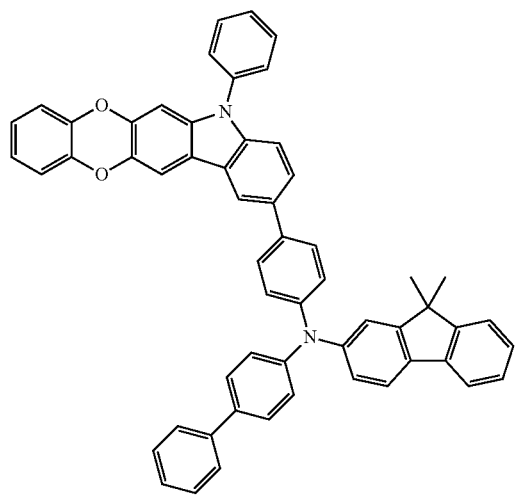
Cpd 48
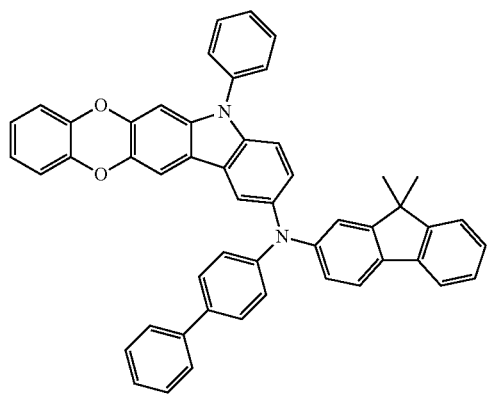

-continued
Cpd 49
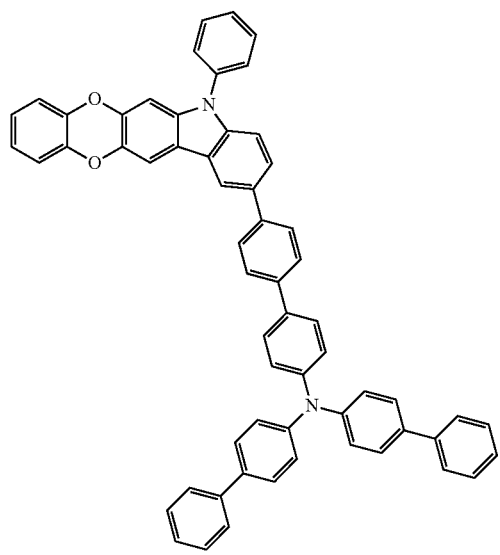
Cpd 50
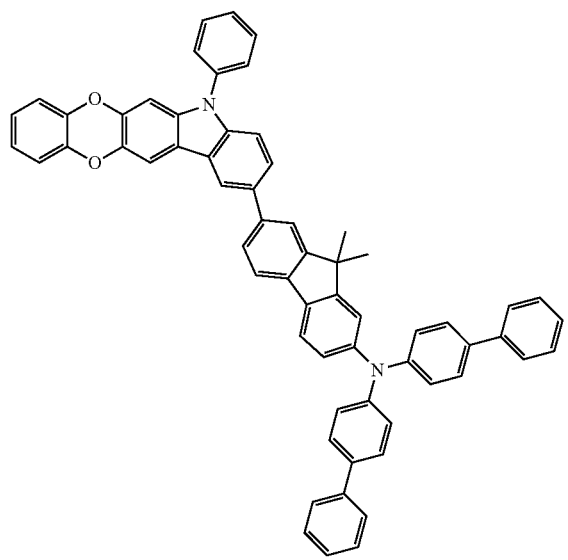
Cpd 51
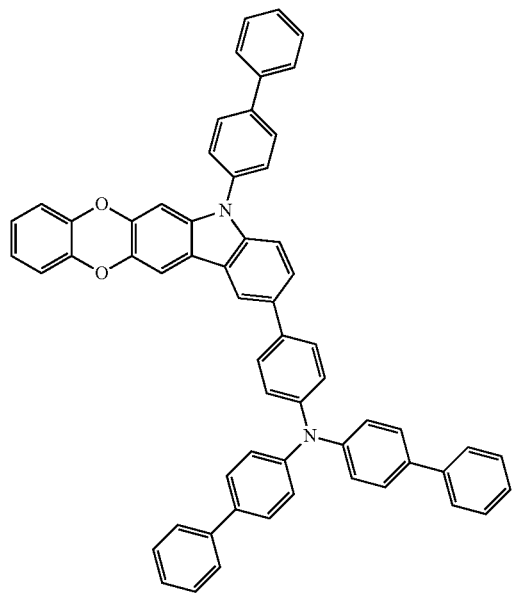
Cpd 52
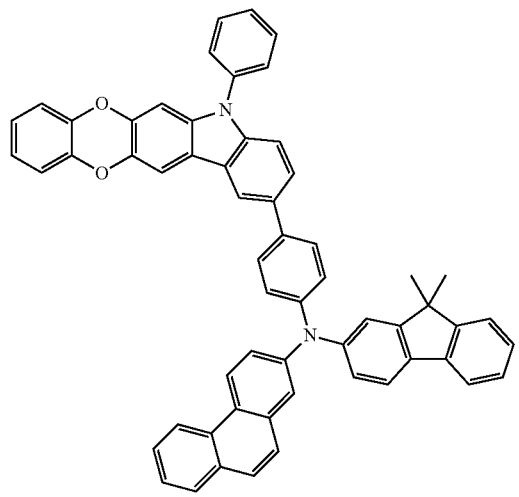

-continued
Cpd 53
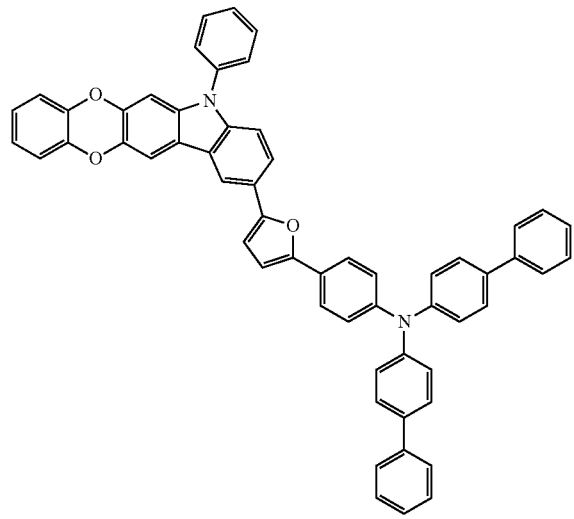
Cpd 54
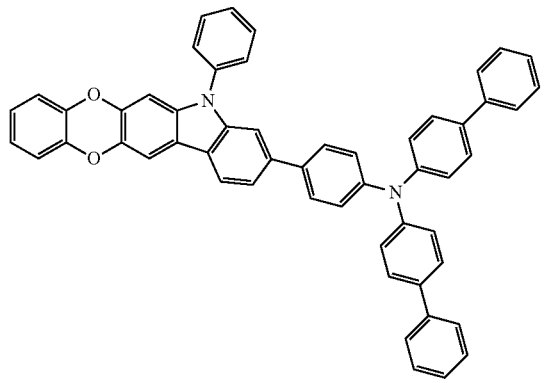
Cpd 55
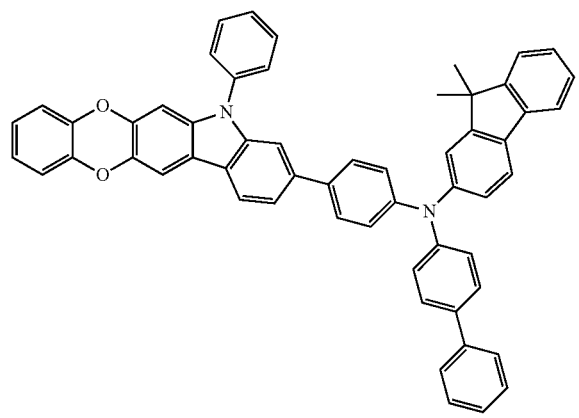
Cpd 56
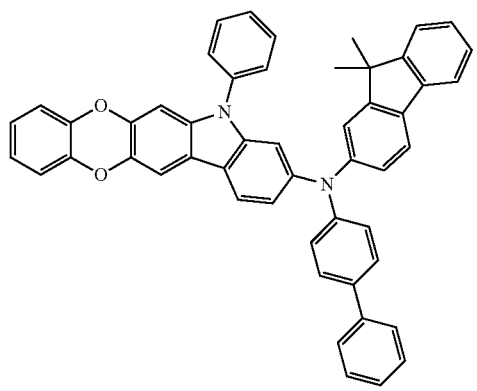
Cpd 57
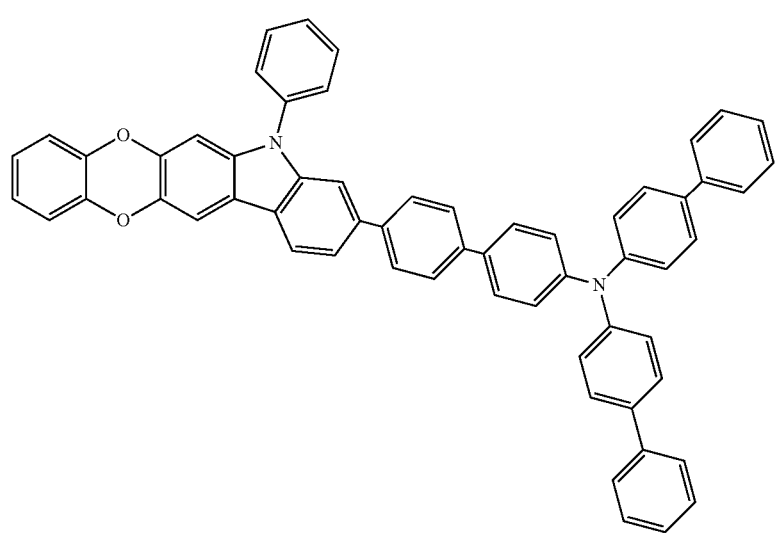

-continued
Cpd 58
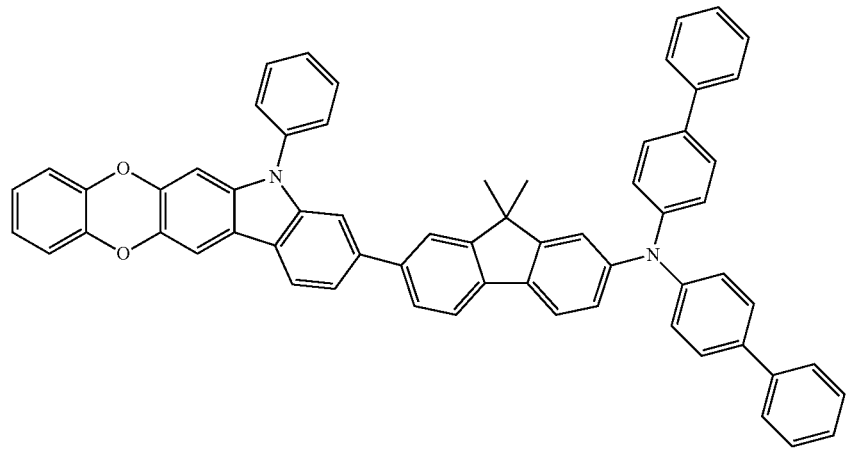
Cpd 59
Cpd 60
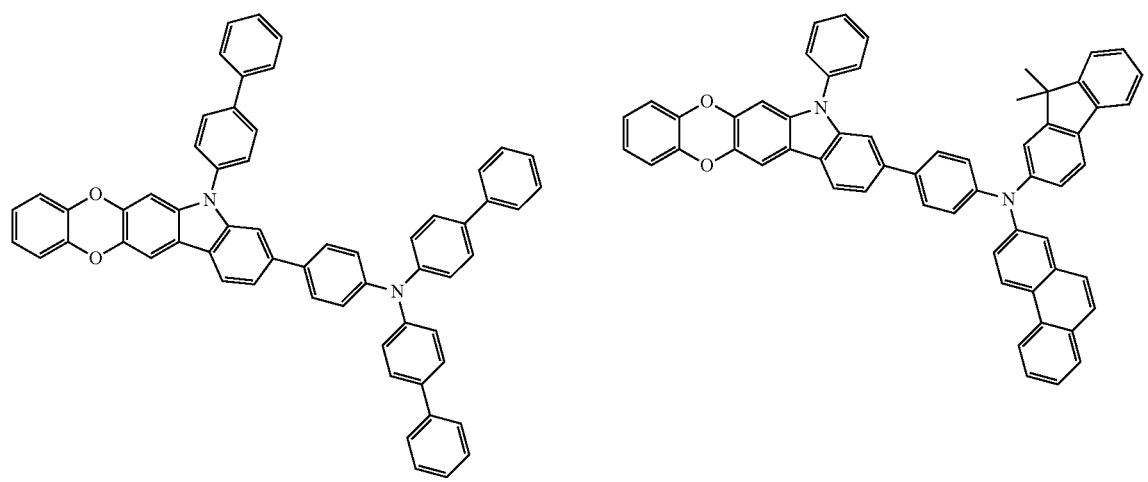
Cpd 61
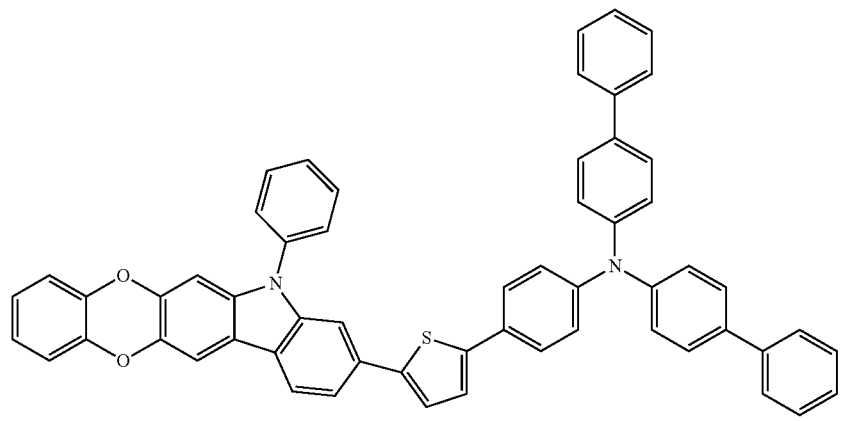

-continued
Cpd 62
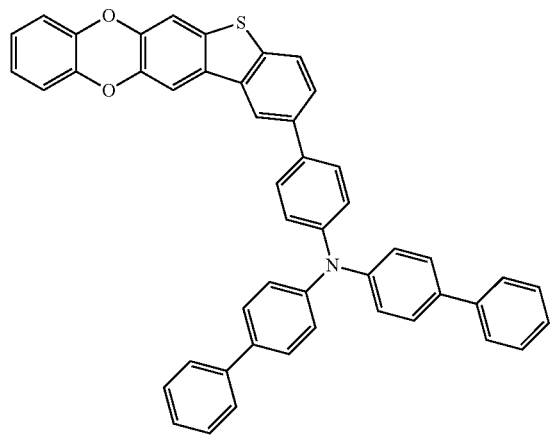
Cpd 63
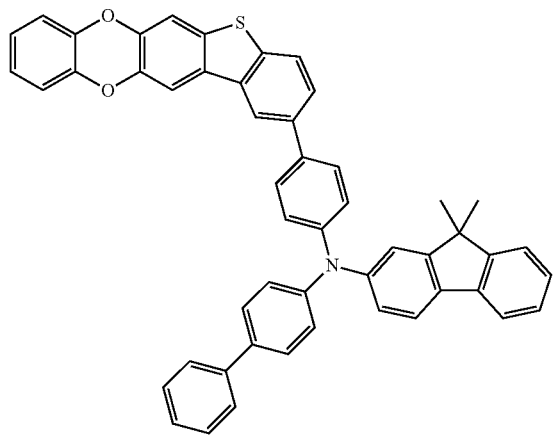
Cpd 64
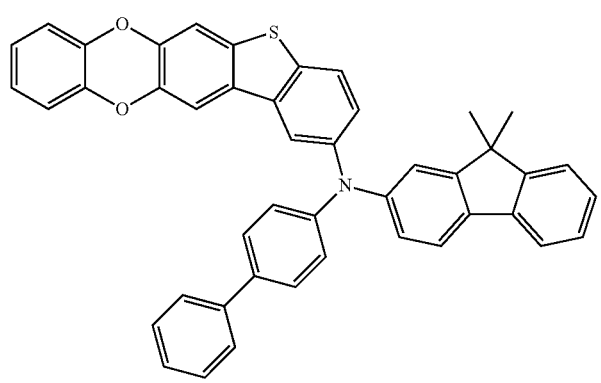
Cpd 65
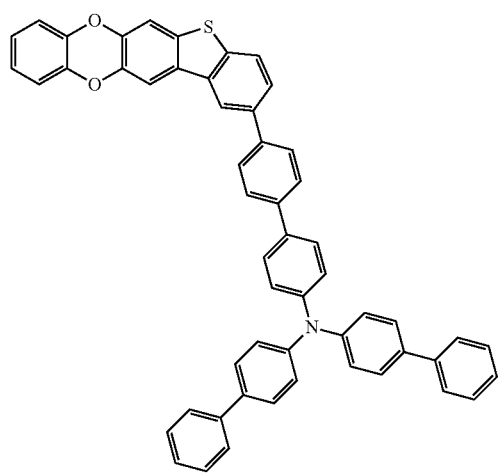
Cpd 66
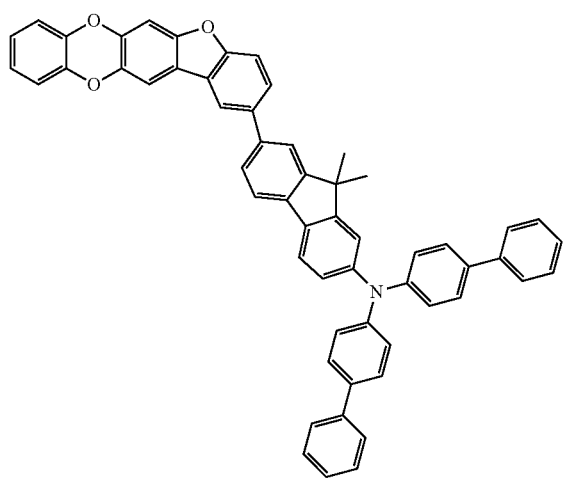

-continued
Cpd 67
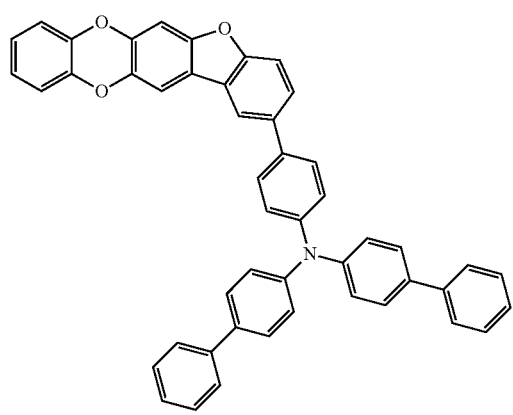
Cpd 68
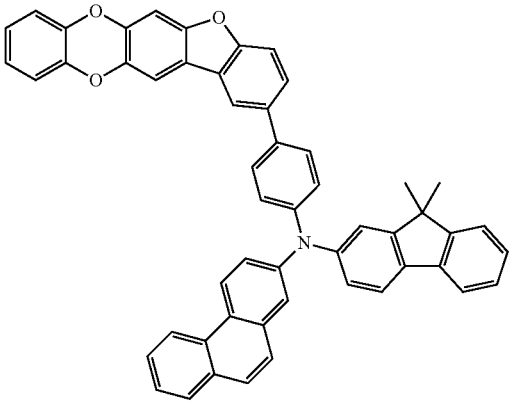
Cpd 69
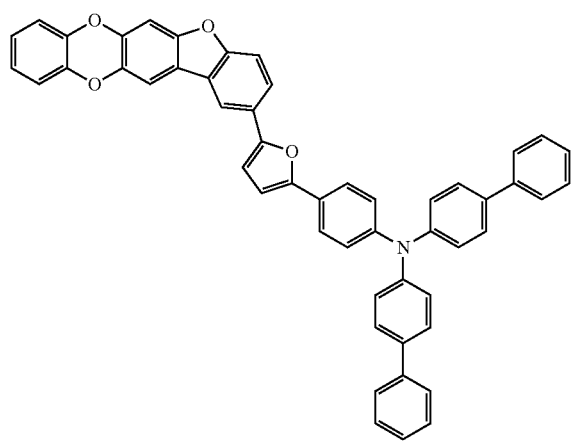
Cpd 70
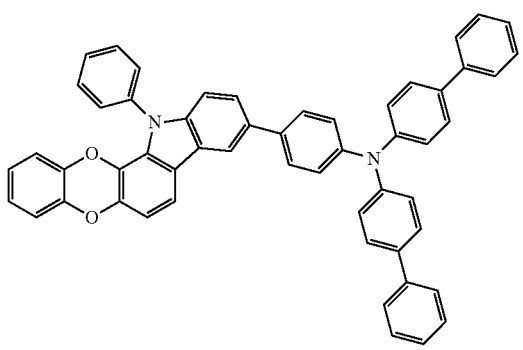
Cpd 71
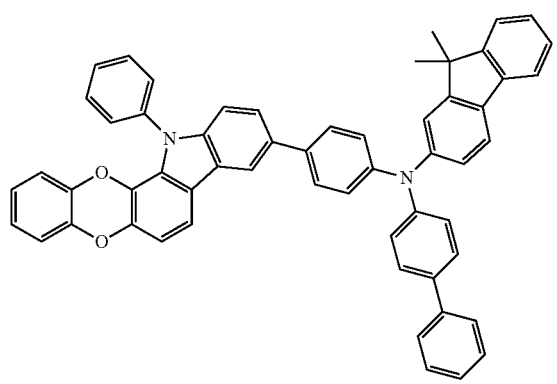
Cpd 72
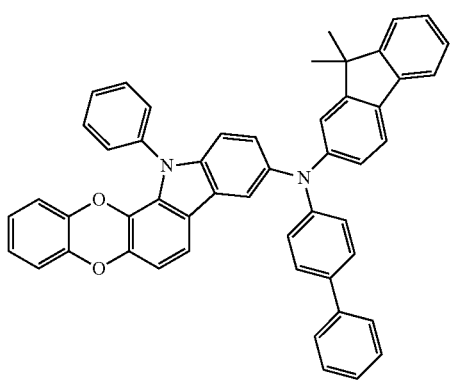

-continued
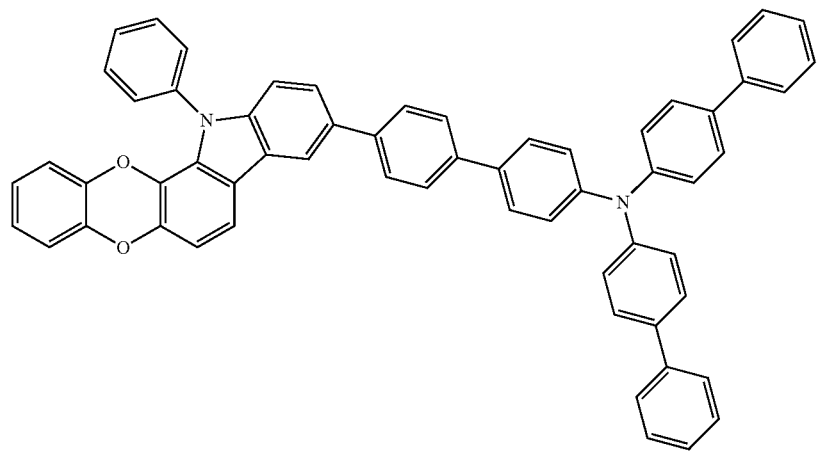
Cpd 73
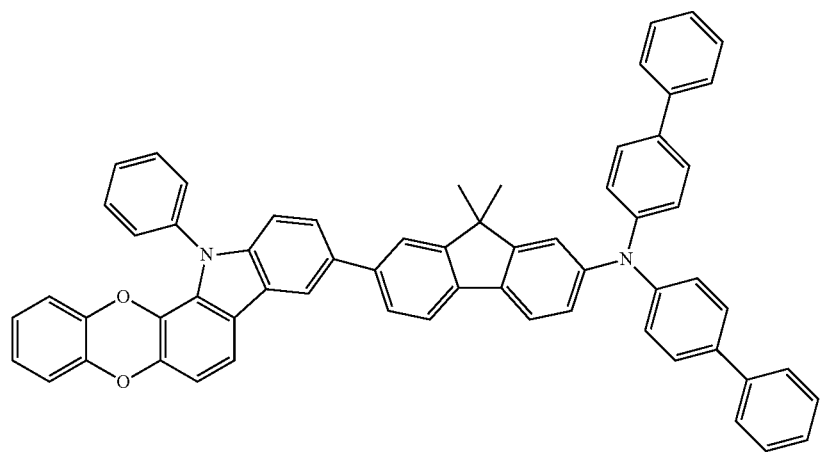
Cpd 74
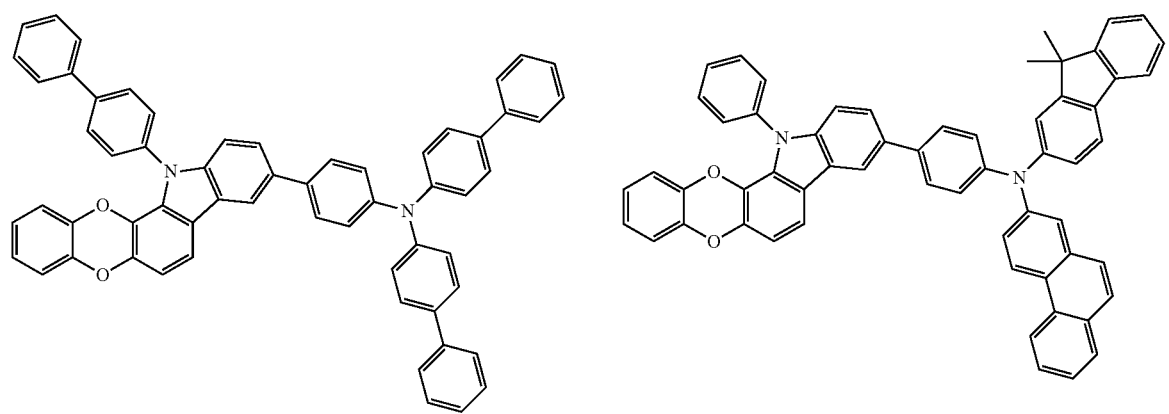
Cpd 75
Cpd 76

-continued
Cpd 77
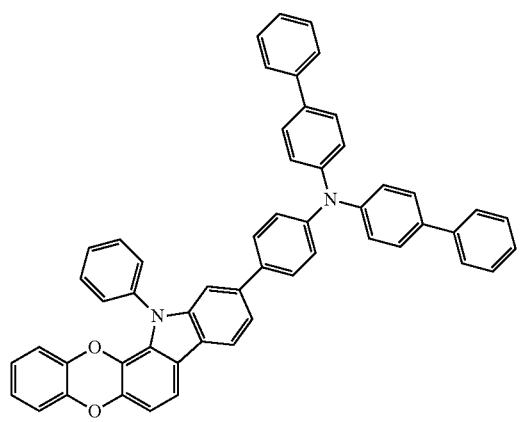
Cpd 78
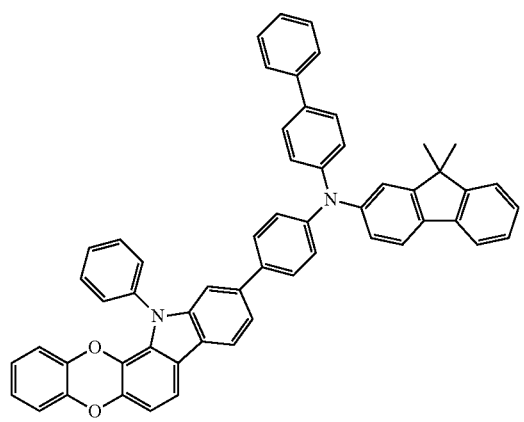
Cpd 79
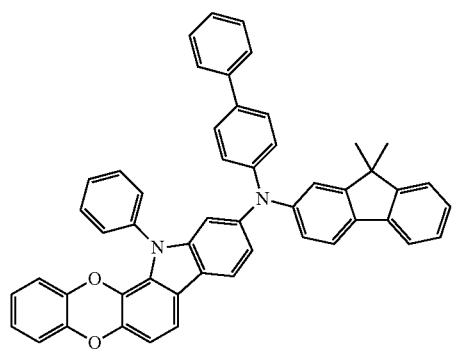
Cpd 80
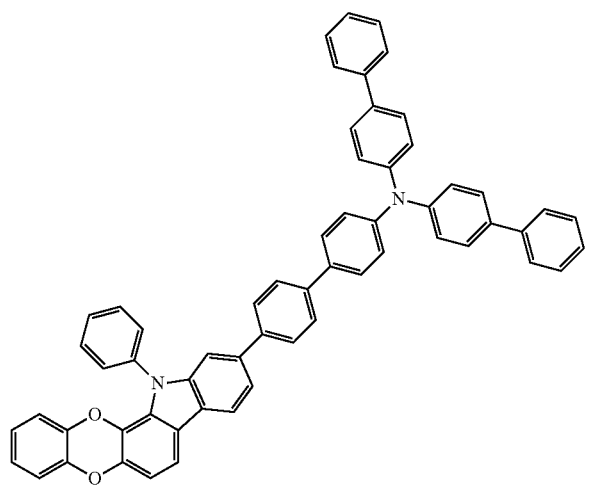
Cpd 81
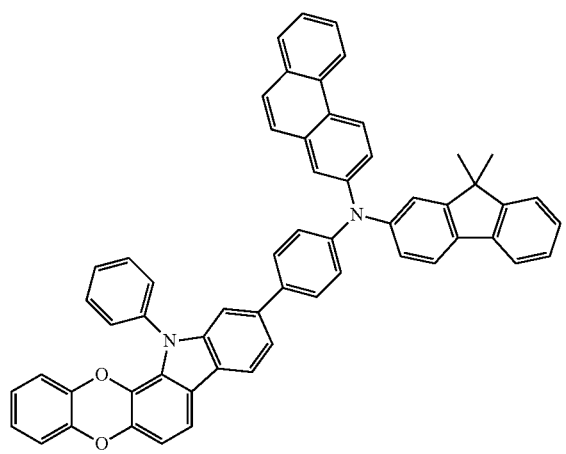
Cpd 82
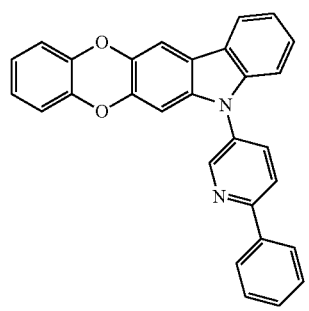

-continued
Cpd 83
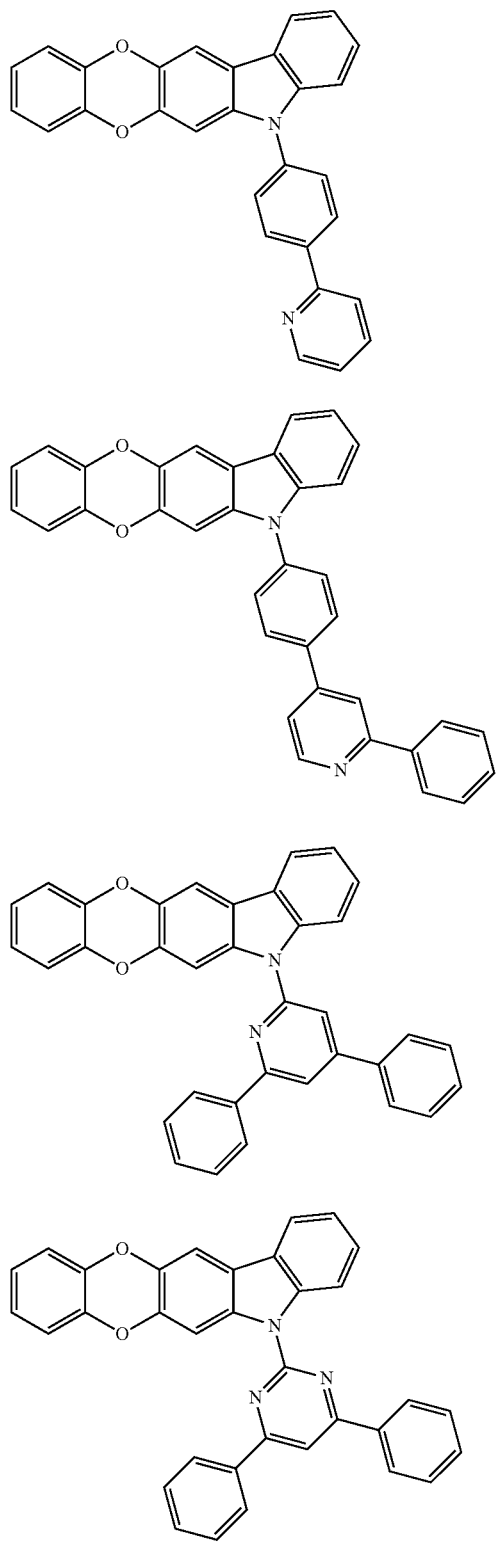
Cpd 84
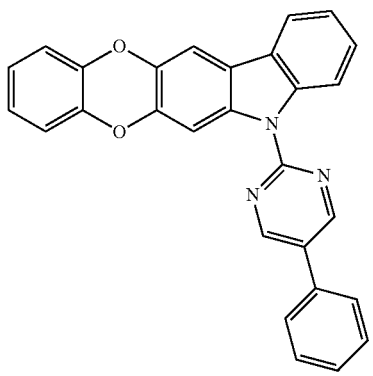
Cpd 85
Cpd 86
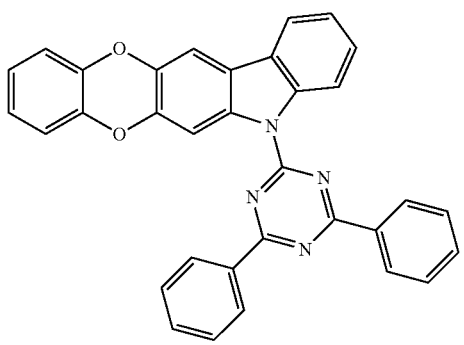
Cpd 87
Cpd 88
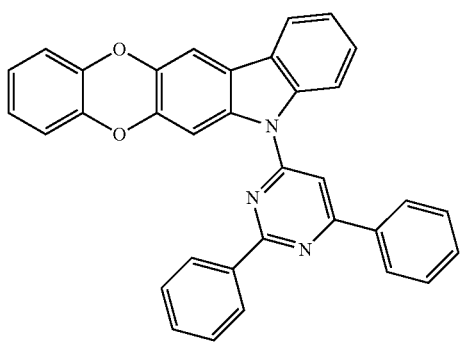
Cpd 89
Cpd 90
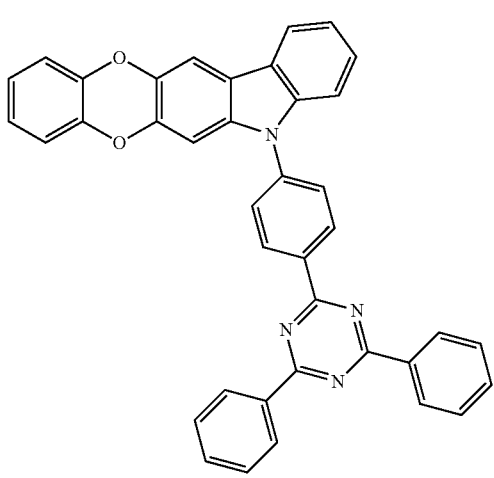

-continued
Cpd 91
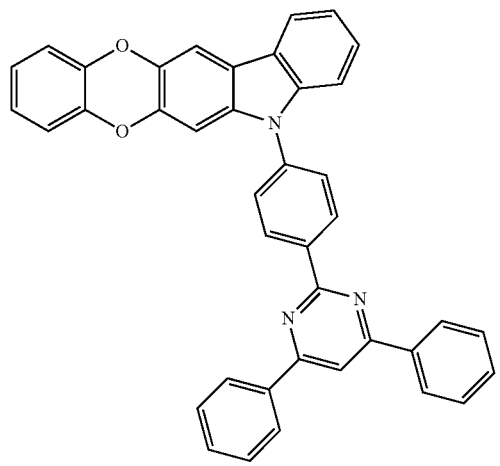
Cpd 92
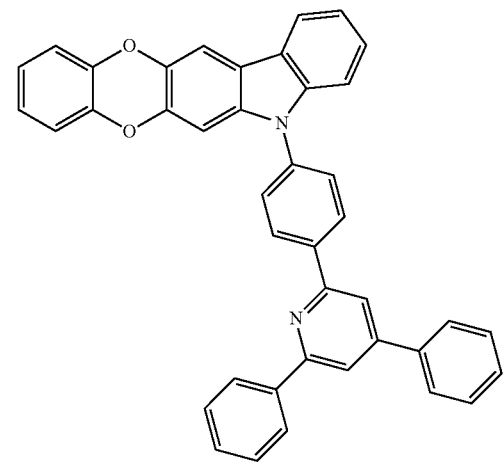
Cpd 93
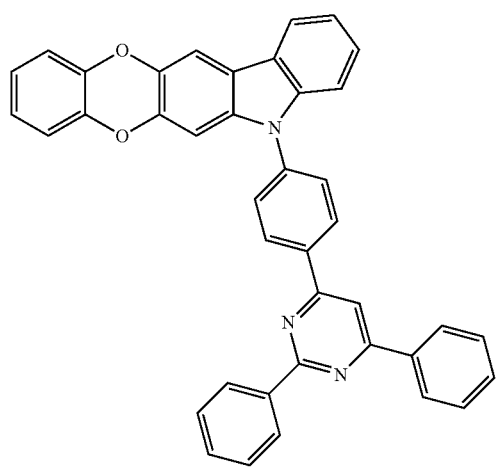
Cpd 94
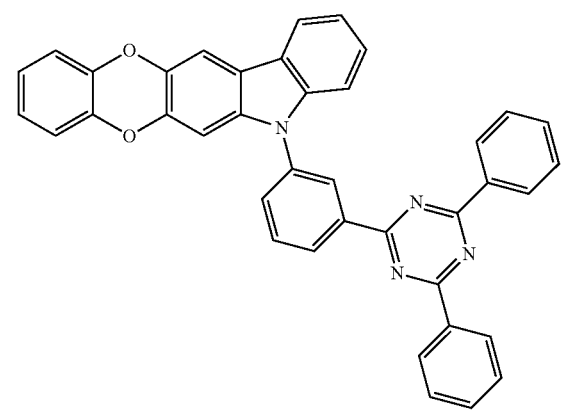
Cpd 95
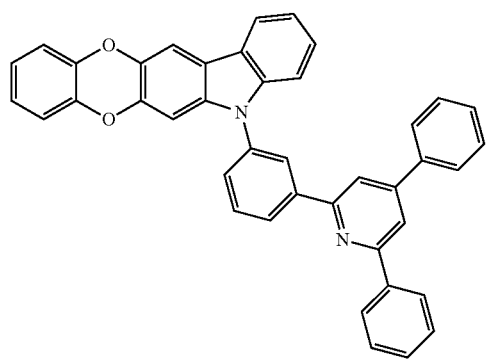
Cpd 96
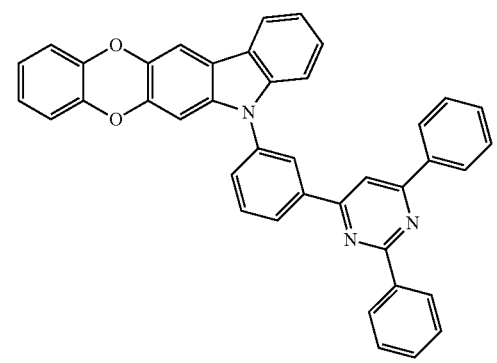

-continued
Cpd 97
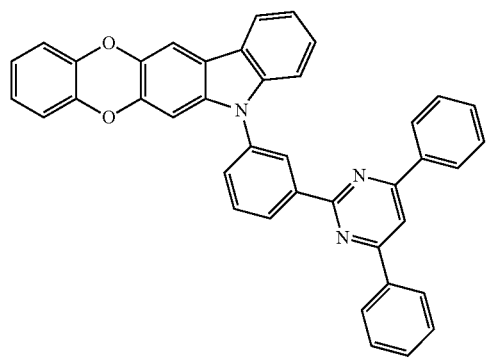
Cpd 98
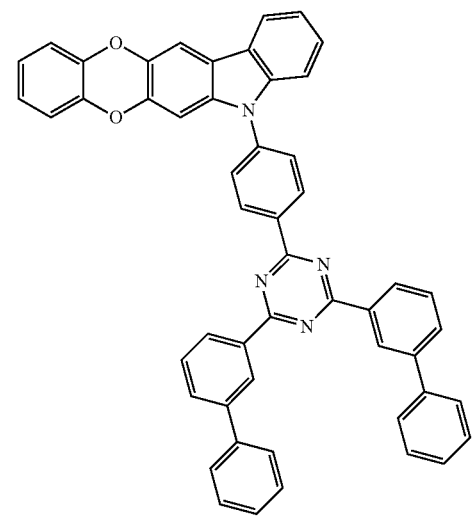
Cpd 99
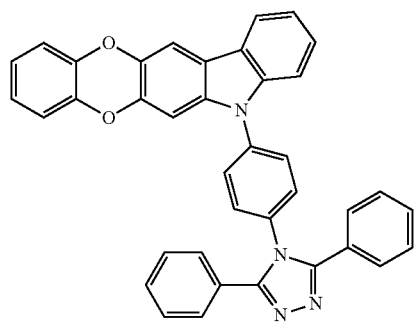
Cpd 100
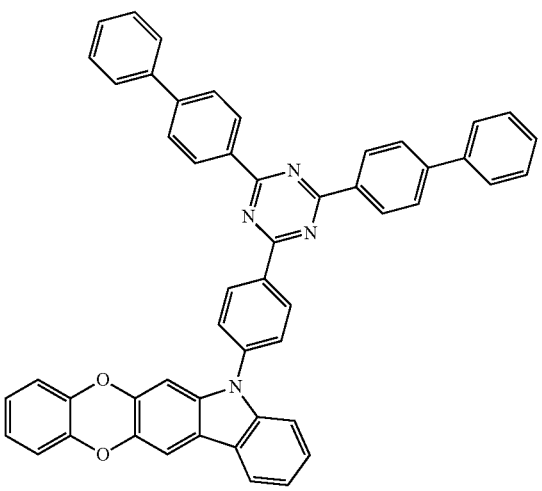
Cpd 101
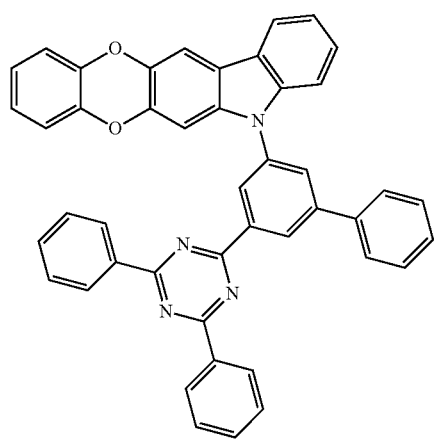
Cpd 102
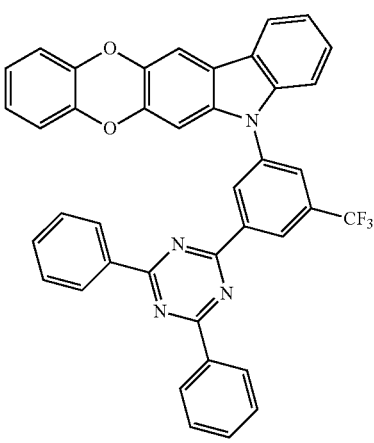

-continued
Cpd 103
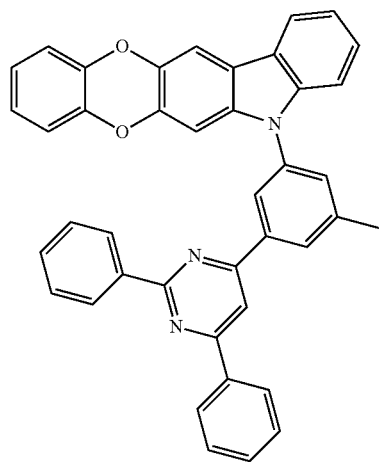
Cpd 104
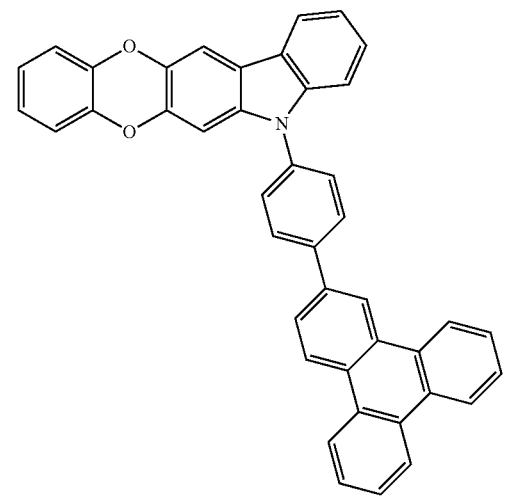
Cpd 105
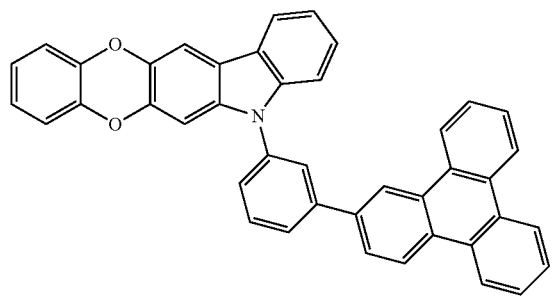
Cpd 106
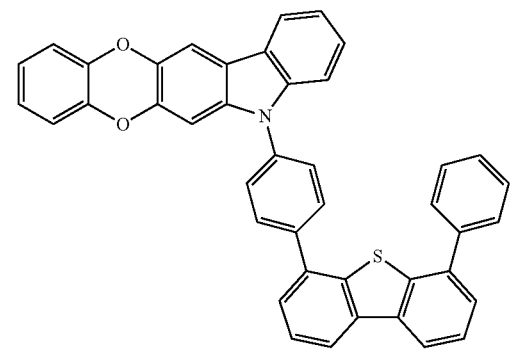
Cpd 107
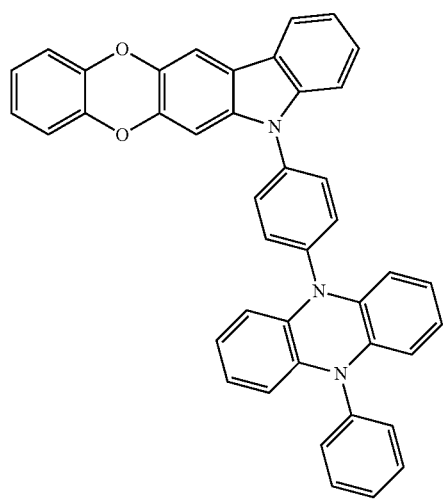
Cpd 108
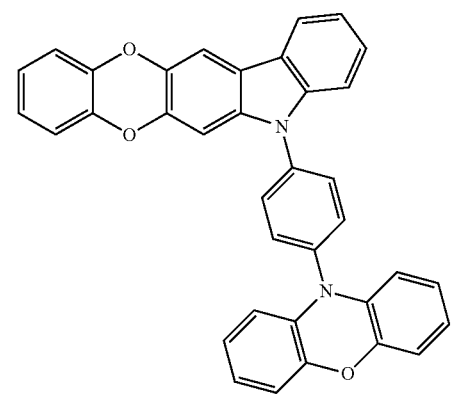

-continued
Cpd 109
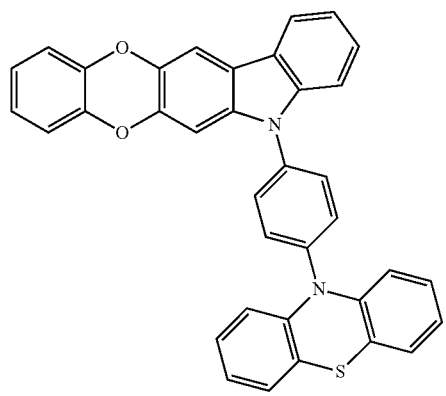
Cpd 110
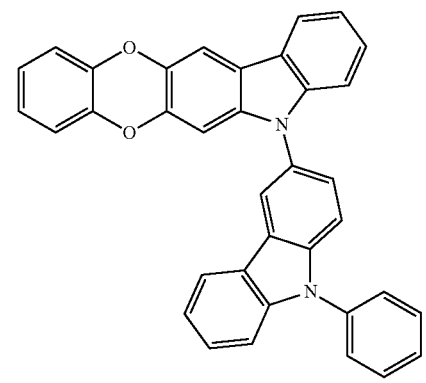
Cpd 111
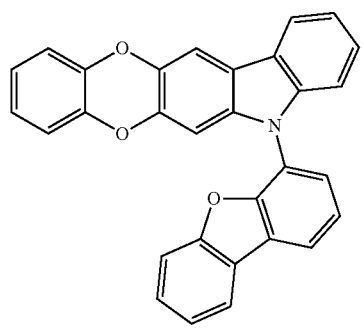
Cpd 112
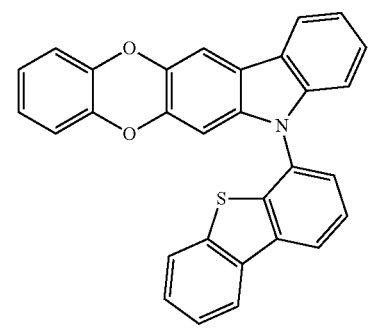
Cpd 113
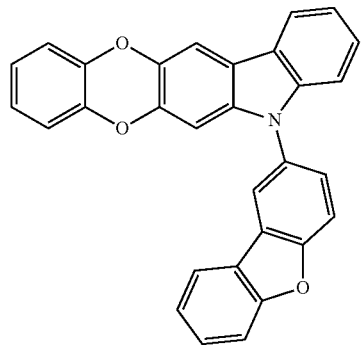
Cpd 114
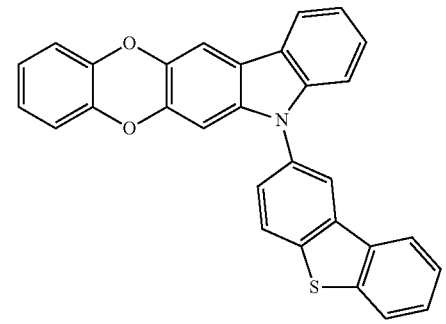
Cpd 115
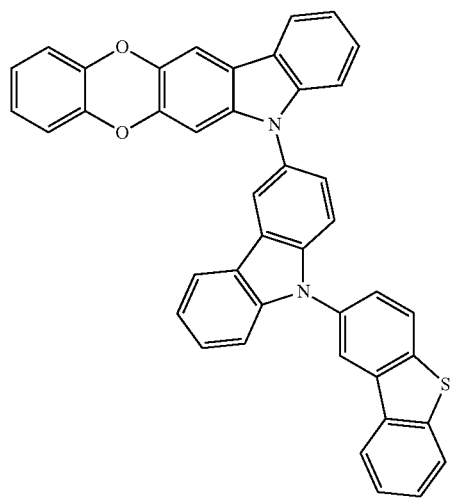
Cpd 116
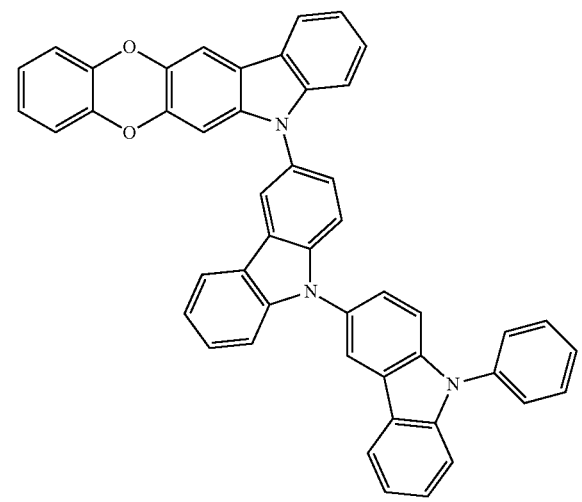

-continued
Cpd 117
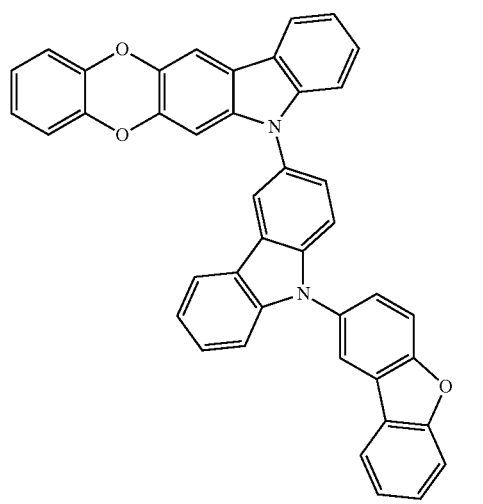
Cpd 118
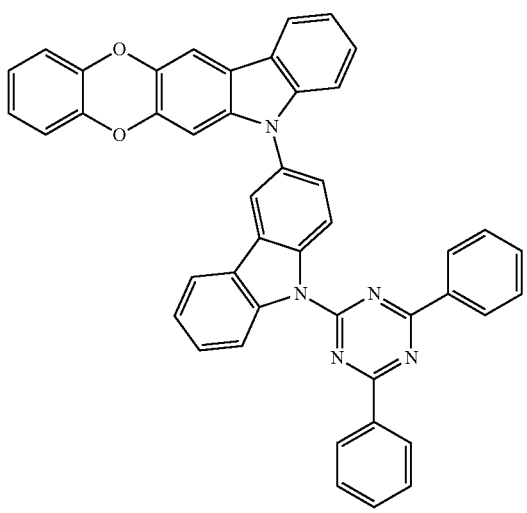
Cpd 119
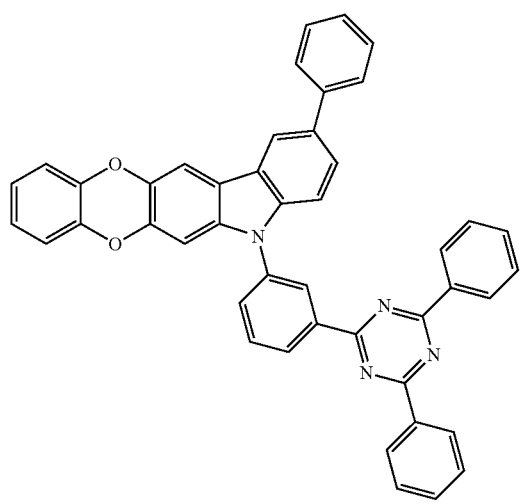
Cpd 120
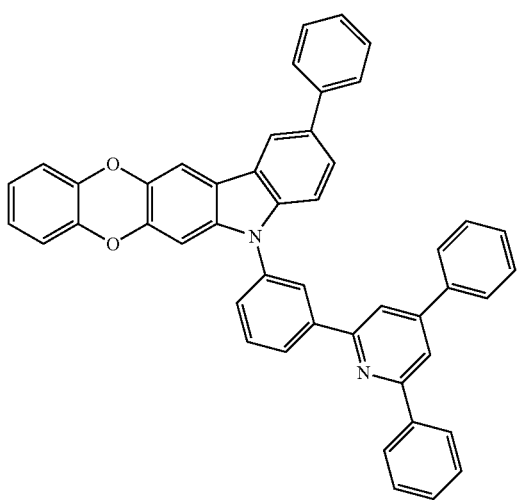
Cpd 121
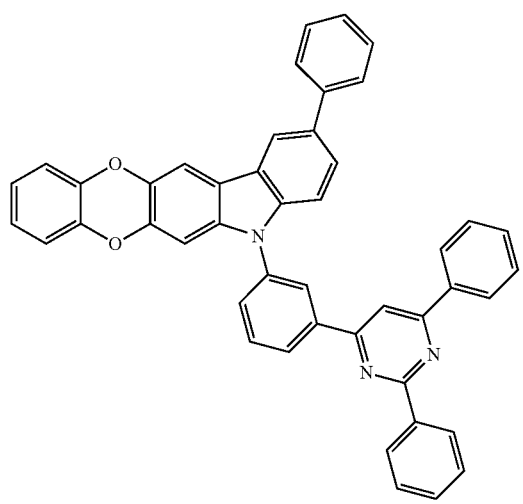
Cpd 122
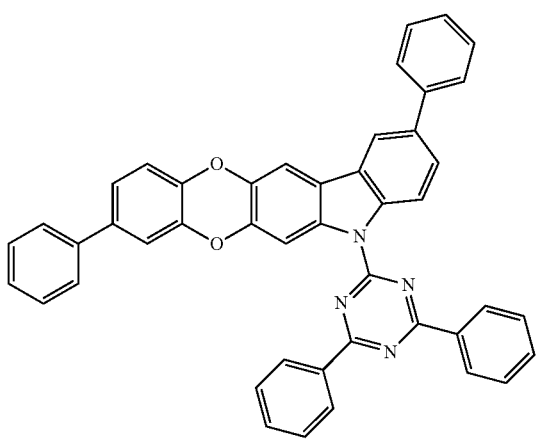

-continued
Cpd 123
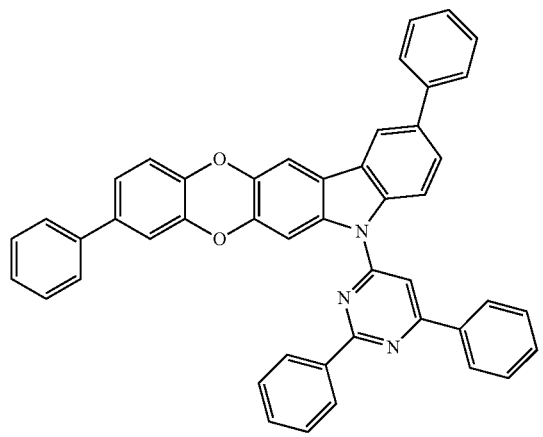
Cpd 124
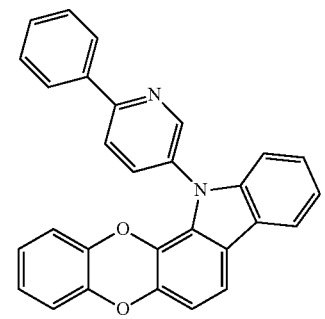
Cpd 125
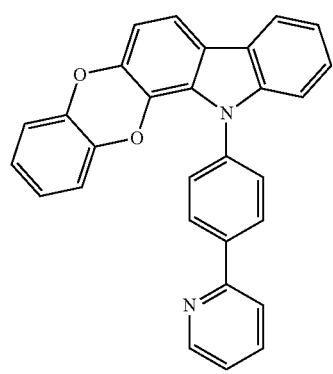
Cpd 126
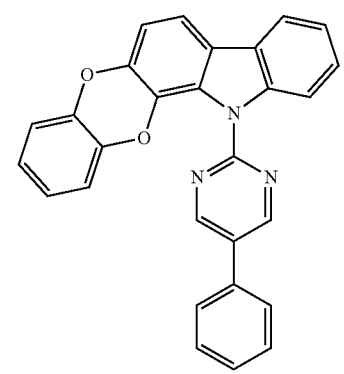
Cpd 127
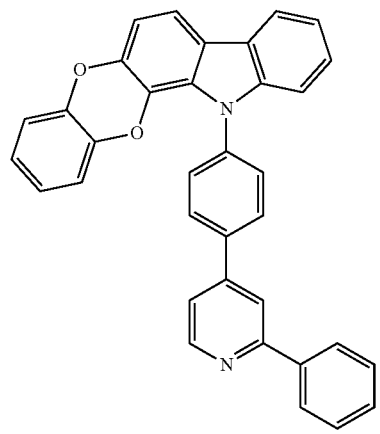
Cpd 128
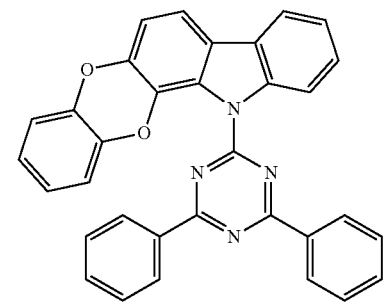
Cpd 129
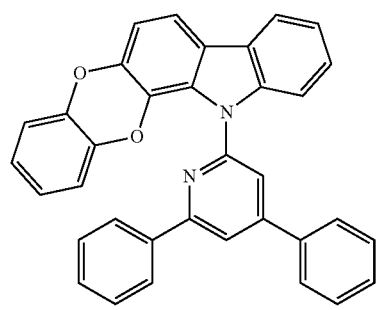
Cpd 130
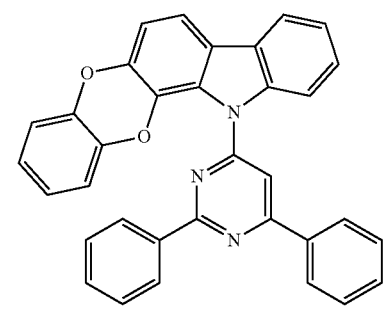

-continued
Cpd 131
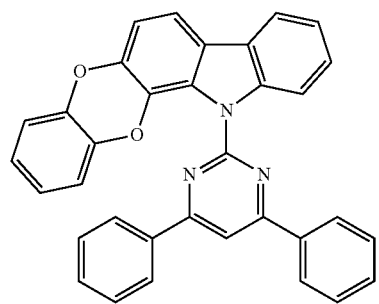
Cpd 132
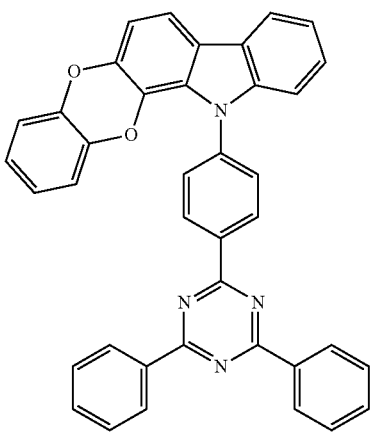
Cpd 133
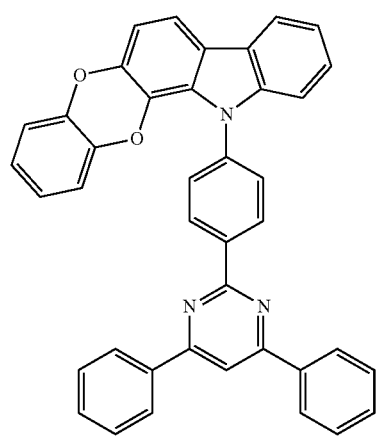
Cpd 134
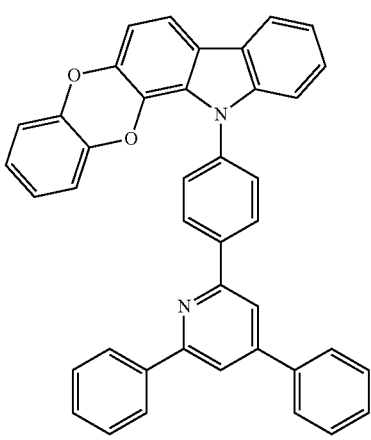
Cpd 135
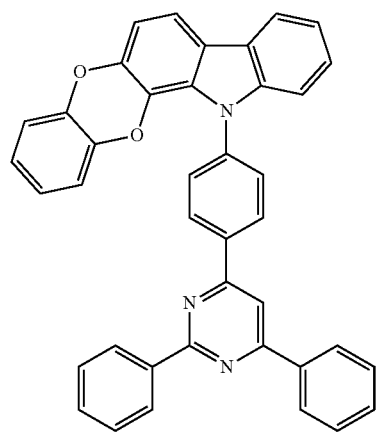
Cpd 136
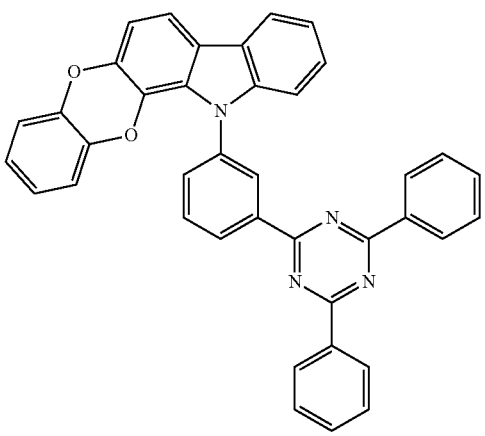

-continued
Cpd 137
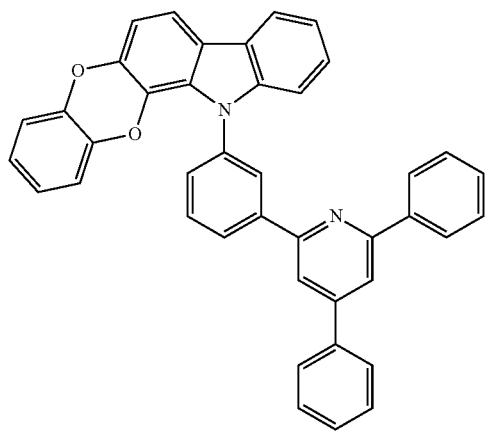
Cpd 138
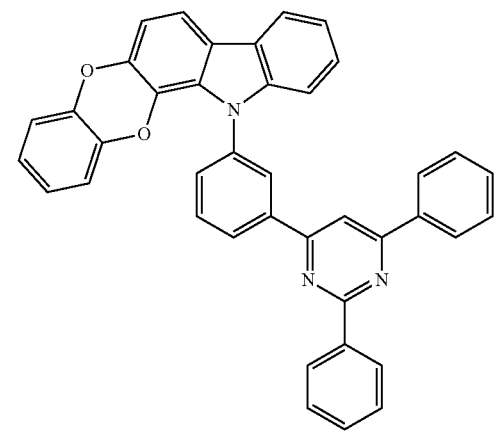
Cpd 139
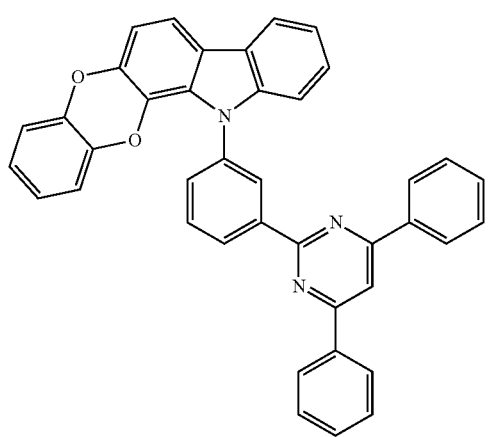
Cpd 140
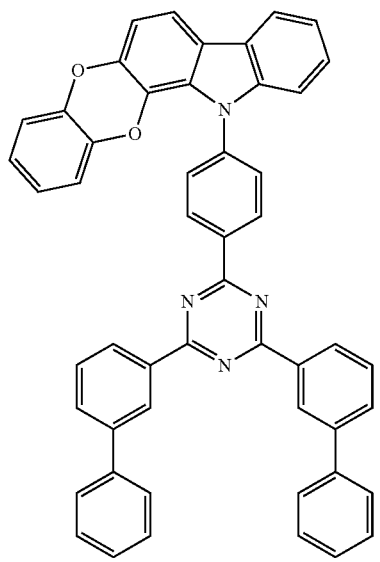
Cpd 141
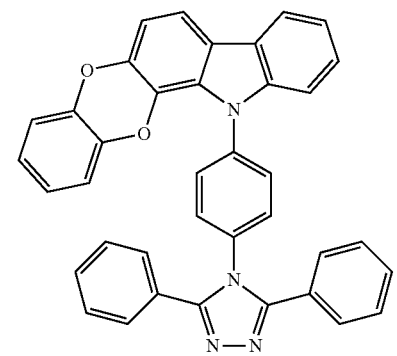

-continued
Cpd 142
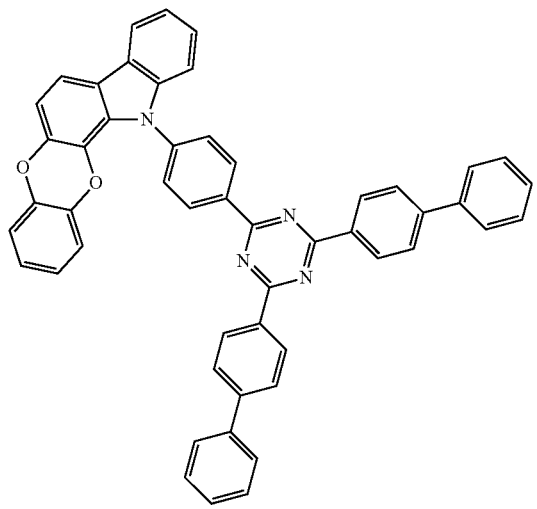
Cpd 143
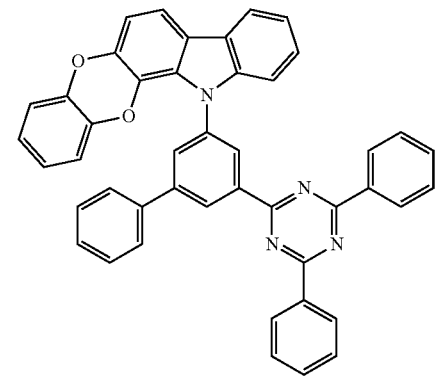
Cpd 144
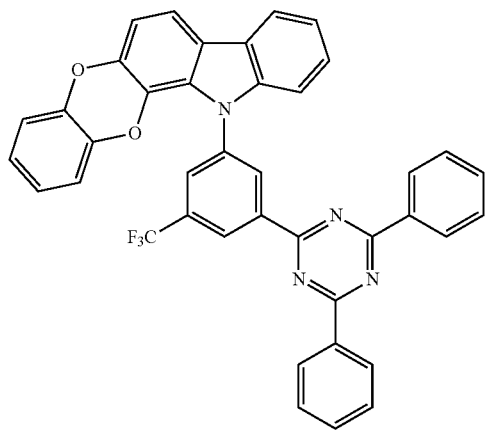
Cpd 145
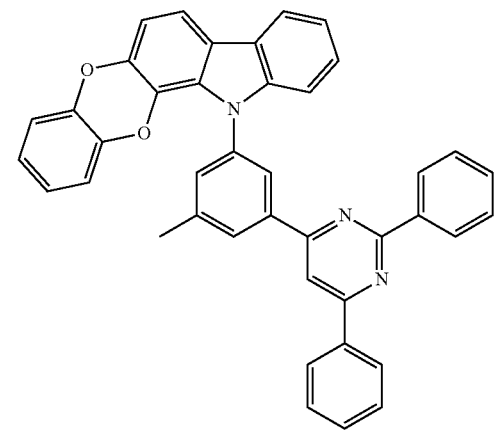
Cpd 146
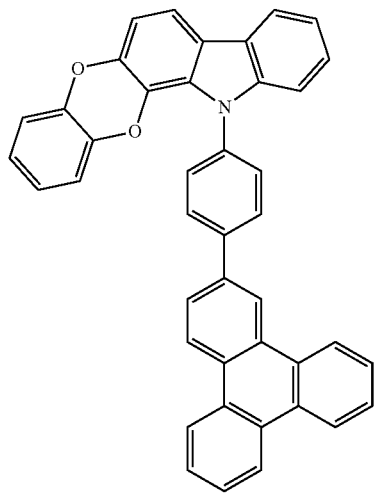
Cpd 147
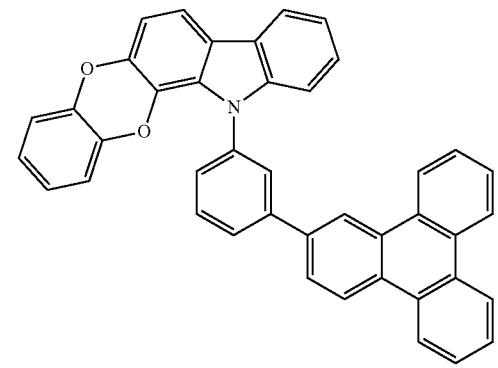

Cpd 148
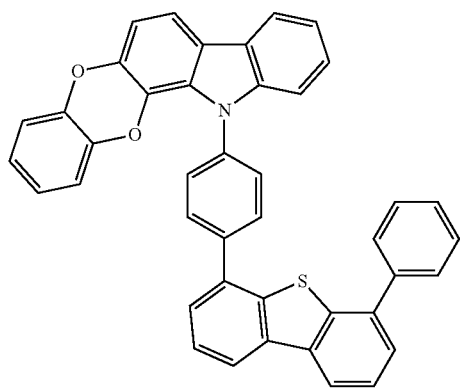
Cpd 149
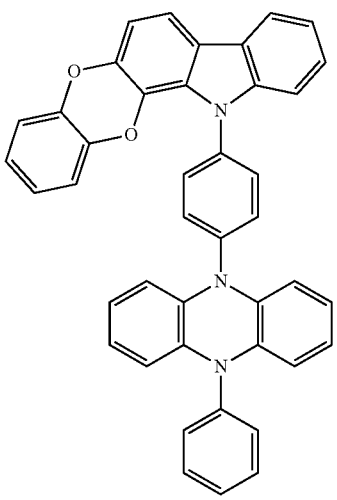
Cpd 150
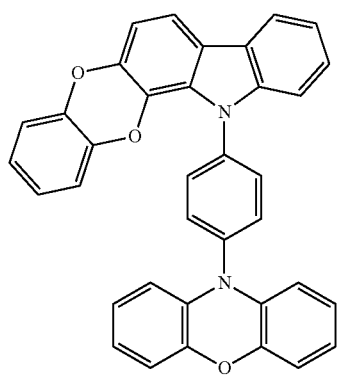
Cpd 151
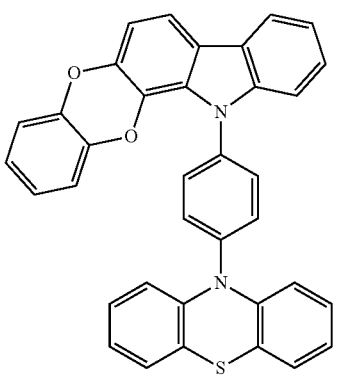
Cpd 152
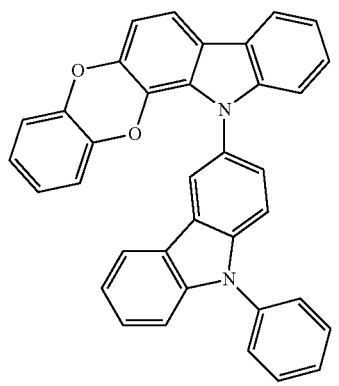
Cpd 153
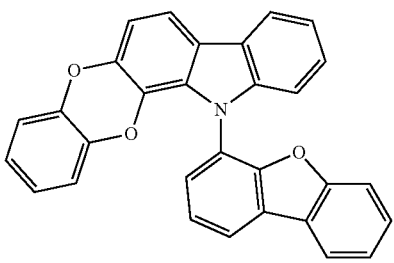
Cpd 154
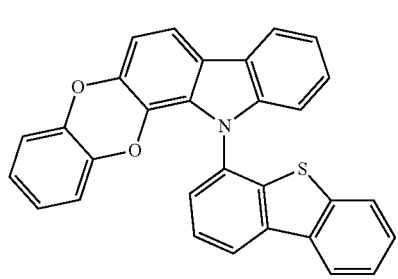
Cpd 155
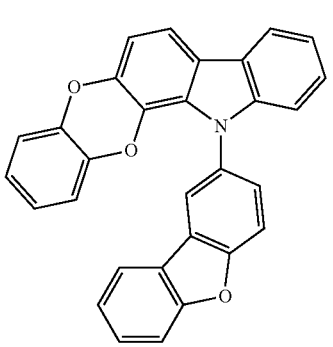

-continued
Cpd 156
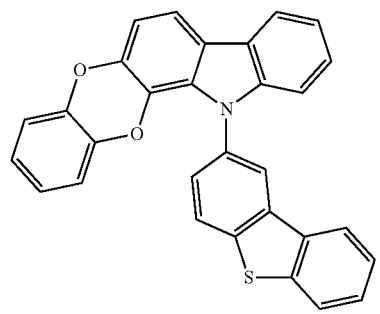
Cpd 157
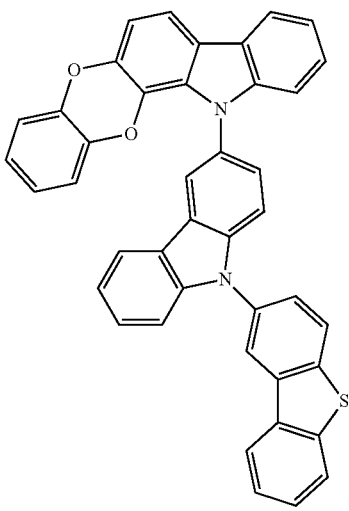
Cpd 158
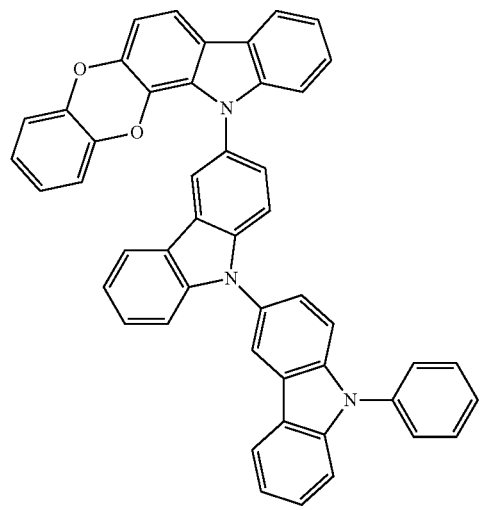
Cpd 159
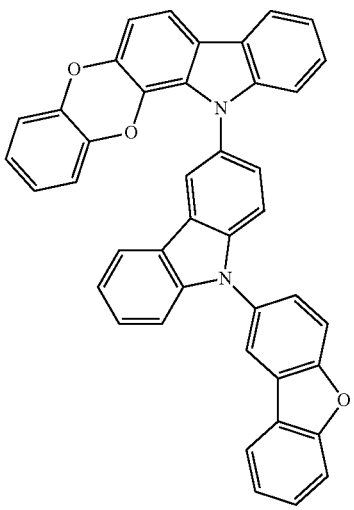
Cpd 160
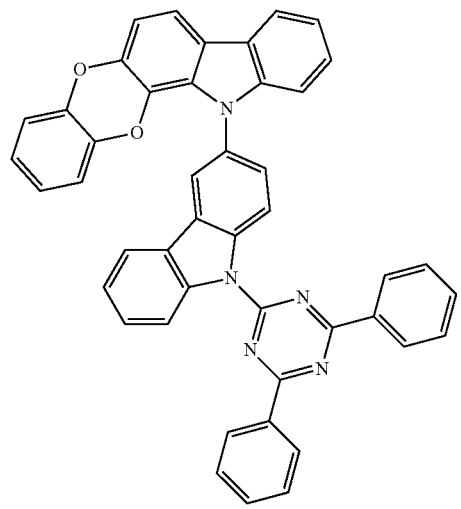
Cpd 161
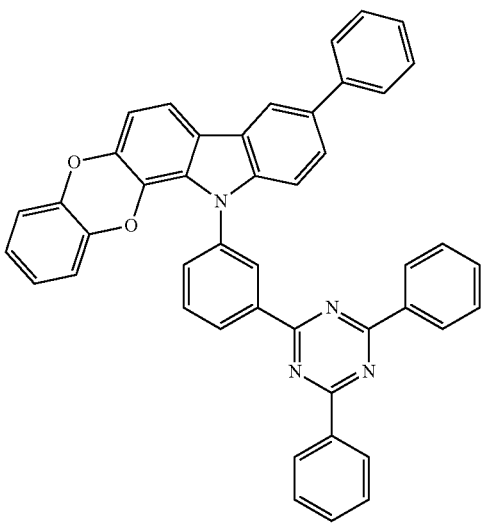

-continued
Cpd 162
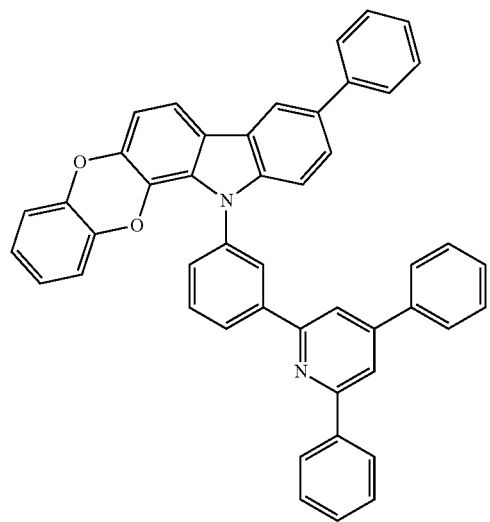
Cpd 163
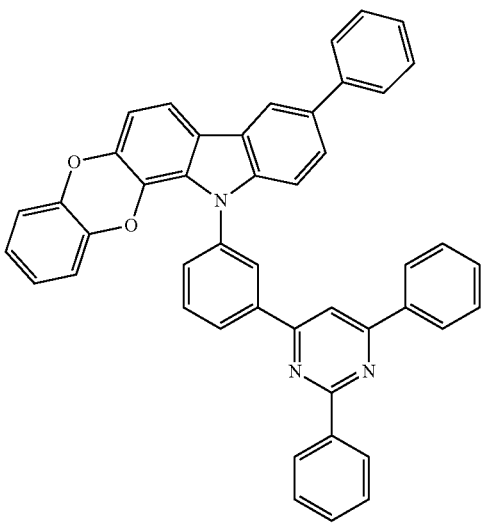
Cpd 164
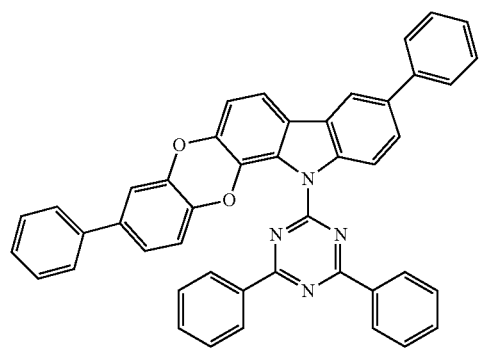
Cpd 165
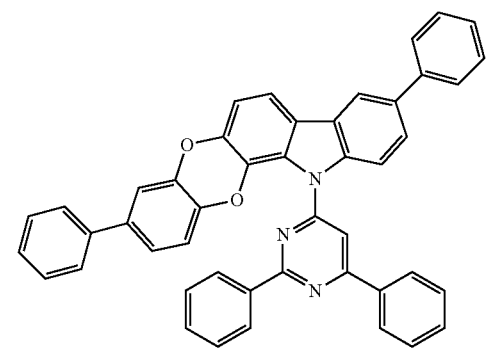
Cpd 166
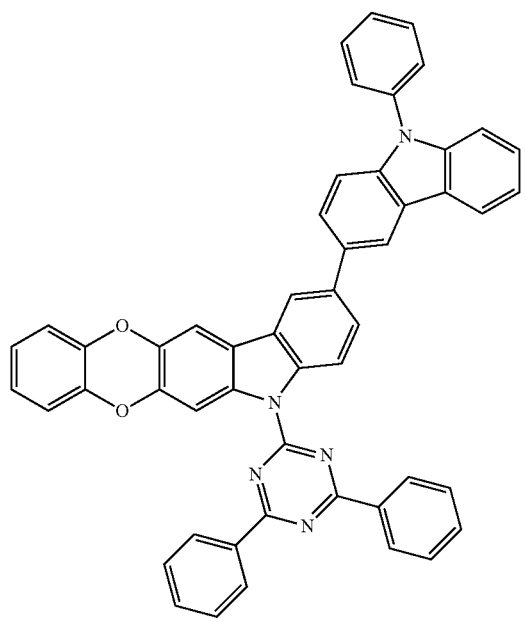
Cpd 167
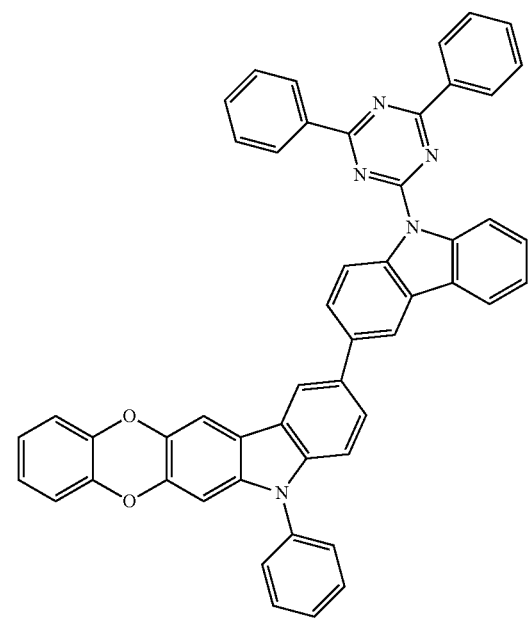

-continued
Cpd 168
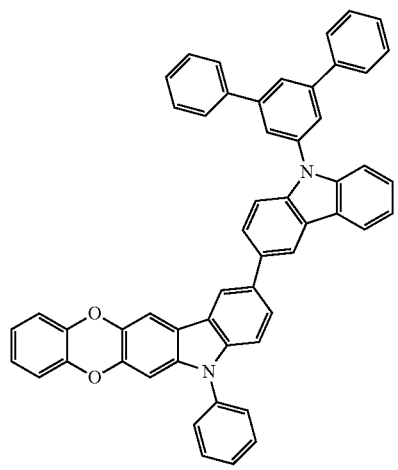
Cpd 169
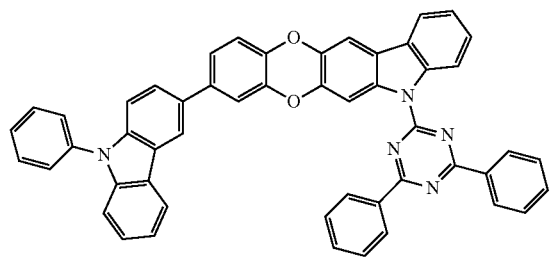
Cpd 170
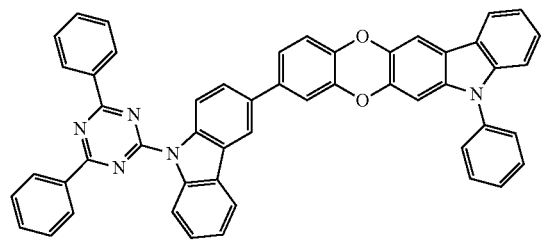
Cpd 171
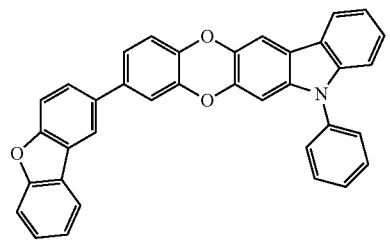
Cpd 172
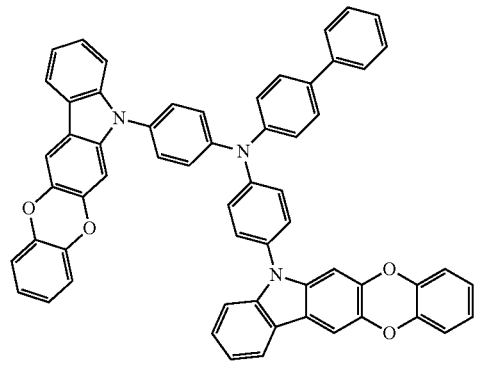
Cpd 173
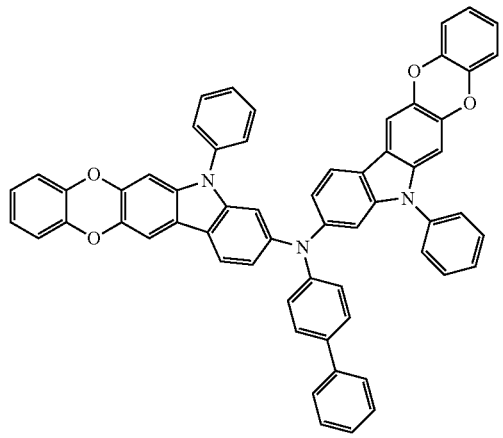
Cpd 174
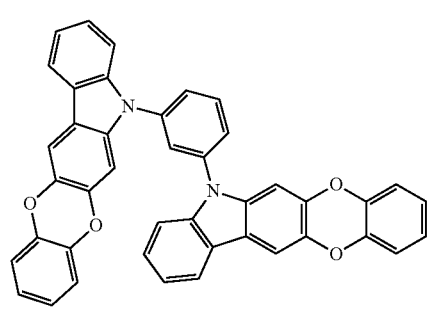
Cpd 175
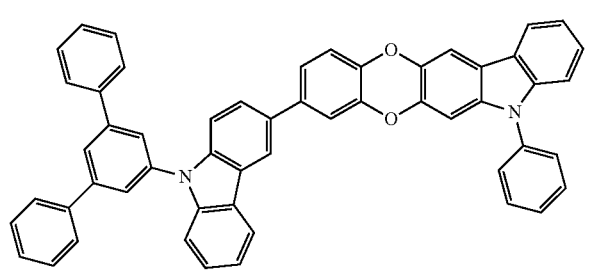

-continued

Cpd 176

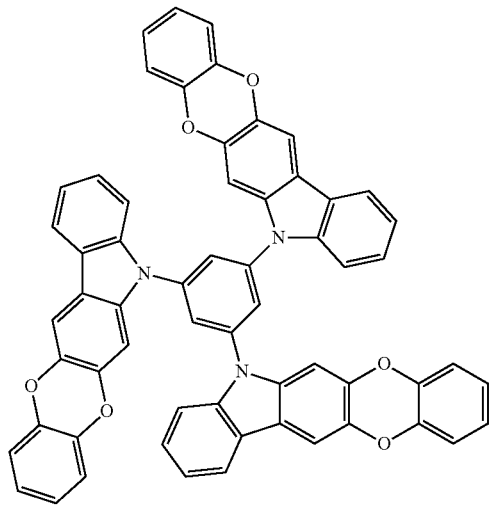

Cpd 177

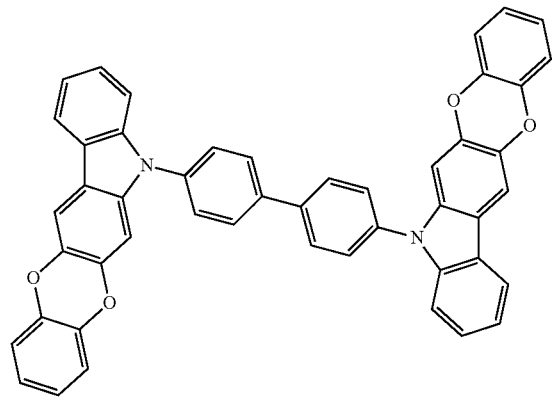

The "unsubstituted alkyl" used in the present disclosure means a monovalent functional group obtained by removing a hydrogen atom from a linear or branched, saturated hydrocarbon having 1 to 40 carbon atoms. Non-limiting examples thereof include methyl, ethyl, propyl, isobutyl, sec-butyl, pentyl, iso-amyl, hexyl, and the like.

The "unsubstituted alkenyl" used in the present disclosure means a monovalent functional group obtained by removing a hydrogen atom from a linear or branched, unsaturated hydrocarbon having 2 to 40 carbon atoms, which has one or more carbon-carbon double bonds. Non-limiting examples thereof include vinyl, allyl, isopropenyl, 2-butenyl, and the like.

The "unsubstituted alkynyl" used in the present disclosure means a monovalent functional group obtained by removing a hydrogen atom from a linear or branched, unsaturated hydrocarbon having 2 to 40 carbon atoms, which has one or more carbon-carbon triple bonds. Non-limiting examples thereof include ethynyl, 2-propynyl, and the like.

The "unsubstituted cycloalkyl" used in the present disclosure means a monovalent functional group obtained by removing a hydrogen atom from a monocyclic or polycyclic non-aromatic hydrocarbon (saturated cyclic hydrocarbon) having 3 to 40 carbon atoms. Non-limiting examples thereof include cyclopropyl, cyclopentyl, cyclohexyl, norbornyl, adamantine, and the like.

The "unsubstituted heterocycloalkyl" used in the present disclosure means a monovalent functional group obtained by removing a hydrogen atom from a non-aromatic hydrocarbon (saturated cyclic hydrocarbon) having 3 to 40 nuclear atoms, and one or more carbons in the ring, preferably 1 to 3 carbons are substituted with a heteroatom such as N, O, Se, or S. Non-limiting examples thereof include morpholine, piperazine, and the like.

The "unsubstituted aryl" used in the present disclosure means a monovalent functional group obtained by removing a hydrogen atom from an aromatic hydrocarbon having 6 to 60 carbon atoms, in which a single ring or two or more rings are combined. In this case, the two or more rings may be simply pendant to each other or pendant to each other in a fused form. Non-limiting examples thereof include phenyl, biphenyl, terphenyl, naphthyl, phenanthryl, anthryl, and the like.

The "unsubstituted heteroaryl" used in the present disclosure is a monovalent functional group obtained by removing a hydrogen atom from a monoheterocyclic or polyheterocyclic aromatic hydrocarbon having 5 to 60 nuclear atoms, and one or more carbons in the ring, preferably 1 to 3 carbons are substituted with a heteroatom such as nitrogen (N), oxygen (O), sulfur (S), or selenium (Se). In this case, the two or more rings may be simply pendant to each other or pendant to each other in a fused form in the heteroaryl, and furthermore, the heteroaryl may also include a form fused with an aryl group. Non-limiting examples of the heteroaryl include: a 6-membered monocyclic ring, such as pyridyl, pyrazinyl, pyrimidinyl, pyridazinyl, and triazinyl; a polycyclic ring, such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like.

The "unsubstituted alkyloxy" used in the present disclosure means a monovalent functional group represented by RO—, and the R is an alkyl having 1 to 40 carbon atoms, and may include a linear, branched, or cyclic structure. Non-limiting examples of the alkyloxy include methoxy, ethoxy, n-propoxy, 1-propoxy, t-butoxy, n-butoxy, pentoxy, and the like.

The "unsubstituted aryloxy" used in the present disclosure means a monovalent functional group represented by R'O—, and the R' is an aryl having 6 to 60 carbon atoms. Non-limiting examples of the aryloxy include phenyloxy, naphthyloxy, diphenyloxy, and the like.

The "unsubstituted alkylsilyl" used in the present disclosure means a silyl which is substituted with an alkyl having 1 to 40 carbon atoms, the "unsubstituted arylsilyl" means a silyl which is substituted with an aryl having 6 to 60 carbon atoms, the "unsubstituted alkylboron" means a boron which is substituted with an alkyl having 1 to 40 carbon atoms, the "unsubstituted arylboron" means a boron which is substituted with an aryl having 6 to 60 carbon atoms, the "unsubstituted arylphosphine" means a phosphine which is substituted with an aryl having 1 to 60 carbon atoms, and the "unsubstituted arylamine" means an amine which is substituted with an aryl having 6 to 60 carbon atoms.

The "fused ring" used in the present disclosure means a fused aliphatic ring, a fused aromatic ring, a fused heteroaliphatic ring, a fused heteroaromatic ring, or a combined form thereof.

The compound of Formula 1 of the present disclosure may be synthesized by a general synthesis method (see Chem. Rev., 60:313 (1960); J. Chem. Soc. 4482 (1955); Chem. Rev. 95: 2457 (1995), and the like). The detailed synthesis process on the compound of the present disclosure will be specifically described in Synthesis Examples to be described below.

Meanwhile, the present disclosure provides an organic electroluminescent device including the above-described compound represented by Formula 1.

Specifically, the present disclosure includes an anode, a cathode, and one or more organic material layers interposed between the anode and the cathode, and at least one of the organic material layers includes the compound represented by Formula 1. In this case, the compounds represented by Formula 1 may be used either alone or in mixture of two or more thereof.

According to an exemplary embodiment of the present disclosure, the one or more organic material layers include a hole injection layer, a hole transport layer, a light emitting layer, an electron transport layer, and an electron injection layer, and among them, at least one of the organic material layer includes the compound represented by Formula 1, and preferably, the light emitting layer or the hole transport layer may include the compound represented by Formula 1. In particular, when the compound represented by Formula 1 is included as a material of light emitting layer in an organic electroluminescent device, the light emitting efficiency, luminance, power efficiency, thermal stability, and device lifetime of the organic electroluminescent device may be enhanced.

For example, the compound represented by Formula 1 may be a phosphorescent host, a fluorescent host, or a dopant material for a light emitting layer, and may be preferably a phosphorescent host of a light emitting layer.

According to another exemplary embodiment of the present disclosure, the one or more organic material layers include a hole injection layer, a hole transport layer, a light emitting auxiliary layer, a light emitting layer, an electron transport layer, and an electron injection layer, and in this case, at least one of the organic material layer, preferably a light emitting auxiliary layer may include the compound of Formula 1. In particular, when the compound of Formula 1 may be used as a material of light emitting auxiliary layer for an organic electroluminescent device, the efficiency (light emitting efficiency and power efficiency), lifetime, luminance, driving voltage, and the like of the organic electroluminescent device may be enhanced.

According to still another exemplary embodiment of the present disclosure, the one or more organic material layers include a hole injection layer, a hole transport layer, a light emitting layer, an electron transport auxiliary layer, an electron transport layer, and an electron injection layer, and in this case, at least one of the organic material layer, preferably an electron transport auxiliary layer may include the compound of Formula 1. In particular, when the compound of Formula 1 may be used as a material of electron transport auxiliary layer for an organic electroluminescent device, the efficiency (light emitting efficiency and power efficiency), lifetime, luminance, driving voltage, and the like of the organic electroluminescent device may be enhanced.

The structure of the above-described organic electroluminescent device of the present disclosure is not particularly limited, and may be, for example, a structure in which an anode, one or more organic material layers, and a cathode are sequentially laminated on a substrate, and an insulation layer or an adhesive layer is inserted into the interface between the electrode and the organic material layer.

According to an exemplary embodiment, the organic electroluminescent device may have a structure in which an anode, a hole injection layer, a hole transport layer, a light emitting layer, an electron transport layer, and a cathode are sequentially laminated on a substrate. Optionally, a light emitting auxiliary layer may be interposed between the hole transport layer and the light emitting layer. Additionally, an electron injection layer may also be disposed on the electron transport layer.

The organic electroluminescent device of the present disclosure may be manufactured by forming an organic material layer and an electrode using materials and methods known in the art, except that at least one (for example, a light emitting layer or a light emitting auxiliary layer) of the aforementioned organic material layers is formed so as to include the compound represented by Formula 1.

The organic material layer may be formed by a vacuum deposition method or a solution application method. Examples of the solution application method include spin coating, dip coating, doctor blading, inkjet printing, or a thermal transfer method, but are not limited thereto.

Examples of a substrate which may be used in the present disclosure include a silicon wafer, a quartz or glass plate, a metal plate, a plastic film or sheet, and the like, and are not limited thereto.

Alternatively, examples of an anode material include a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as polythiophene, poly(3-methylthiophene), poly[3,4-(ethylene-1, 2-dioxy)thiophene] (PEDT), polypyrrole, and polyaniline; or carbon black, and the like, but are not limited thereto.

Further, examples of a cathode material include: a metal, such as magnesium, calcium, sodium, potassium, titanium, indium, yttrium, lithium, gadolinium, aluminum, silver, tin, or lead, or alloys thereof; a multi-layer structured material, such as LiF/Al or $LiO_2$/Al, and the like, but are not limited thereto.

Further, a material used for a hole injection layer, a hole transport layer, an electron injection layer, and an electron transport layer is not particularly limited as long as the material is a typical material known in the art.

Hereinafter, the present disclosure will be described in detail through Examples, but the following Examples only exemplify the present disclosure, and the present disclosure is not limited by the following Examples.

[Preparation Example 1] Synthesis of Compounds Inv1 and Inv2

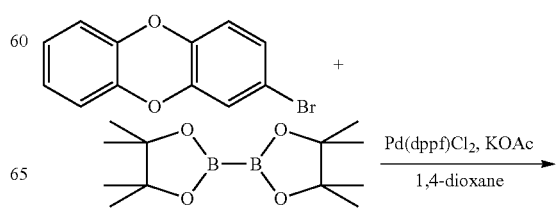

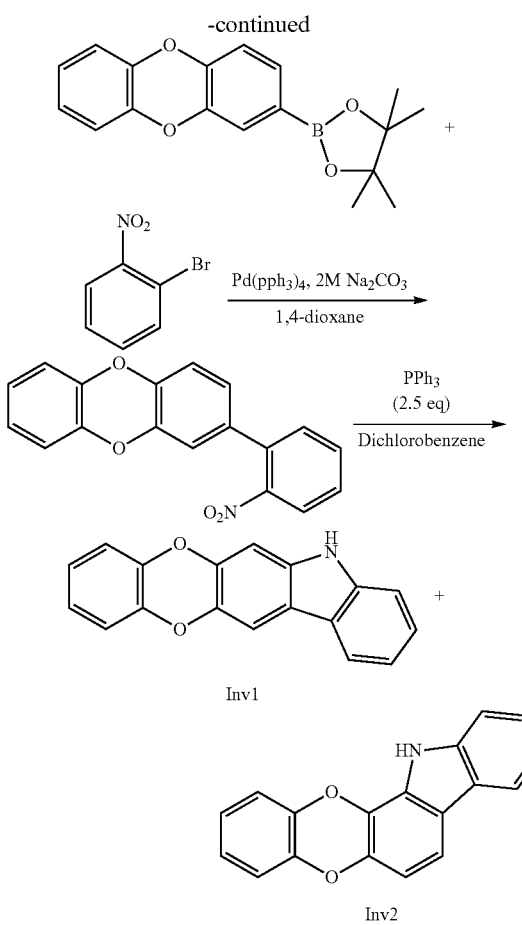

Inv1

Inv2

<Step 1> Synthesis of 2-(dibenzo[b,e][1,4]dioxin-2-yl)-4,4,5,5-tetramethyl-1,3,2-dioxaborolane 2-bromodibenzo[b,e][1,4]dioxine (100 g, 0.38 mol), bis(pinacolato)diboron (115.8 g, 0.46 mol), Pd(dppf)Cl$_2$ (31 g, 0.038 mol), and KOAc (111.9 g, 1.14 mol) were put into a flask, 1,4-dioxane (2 L) was added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(dibenzo[b,e][1,4]dioxin-2-yl)-4,4,5,5-tetramethyl-1,3,2-dioxaborolane (73 g, yield 62%).

<Step 2> Synthesis of 2-(2-nitrophenyl)dibenzo[b,e][1,4]dioxine

The 2-(dibenzo[b,e][1,4]dioxin-2-yl)-4,4,5,5-tetramethyl-1,3,2-dioxaborolane (73 g, 0.235 mol) obtained in <Step 1>, 1-bromo-2-nitrobenzene (57 g, 0.282 mol), and Pd(PPh$_3$)$_4$ (13.5 g, 0.011 mol) were put into a flask, a 2 M saturated aqueous solution of Na$_2$CO$_3$ (352 ml) and 1,4-dioxane (2 L) were added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(2-nitrophenyl)dibenzo[b,e][1,4]dioxine (65 g, yield 91%).

<Step 3> Synthesis of Compounds Inv1 and Inv2

The 2-(2-nitrophenyl)dibenzo[b,e][1,4]dioxine (65 g, 0.212 mol) obtained in <Step 2>, triphenylphosphine (PPh$_3$) (67 g, 0.255 mol), and 1,2-dichlorobenzene (1 L) were mixed under nitrogen flow, and then the resulting mixture was stirred for 12 hours. After the reaction was terminated, 1,2-dichlorobenzene was removed, and an organic layer was extracted with dichloromethane. The obtained organic layer was dried over Na$_2$SO$_4$, distilled under reduced pressure, and then purified with column chromatography to obtain Compound Inv1 (35 g, yield 60%) and Compound Inv2 (12 g, yield 20%).

[Preparation Example 2] Synthesis of Compounds Inv3 and Inv4

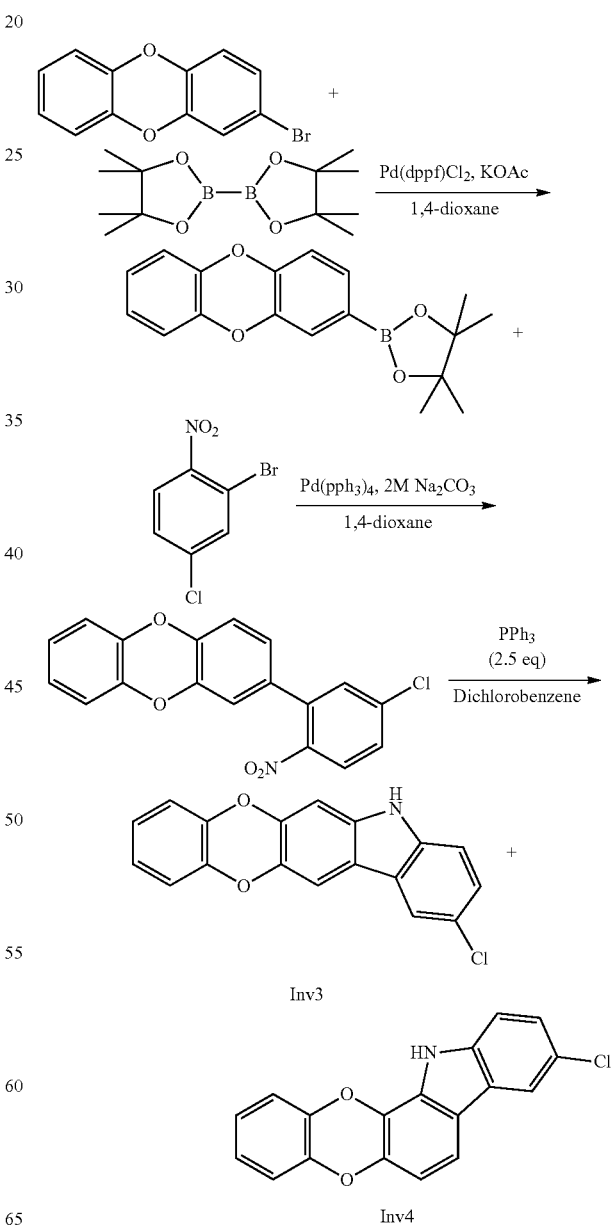

Inv3

Inv4

<Step 1> Synthesis of 2-(dibenzo[b,e][1,4]dioxin-2-yl)-4,4,5,5-tetramethyl-1,3,2-dioxaborolane 2-bromodibenzo[b,e][1,4]dioxine (100 g, 0.38 mol), bis(pinacolato)diboron (115.8 g, 0.46 mol), Pd(dppf)Cl$_2$ (31 g, 0.038 mol), and KOAc (111.9 g, 1.14 mol) were put into a flask, 1,4-dioxane (2 L) was added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(dibenzo[b,e][1,4]dioxin-2-yl)-4,4,5,5-tetramethyl-1,3,2-dioxaborolane (73 g, yield 62%).

<Step 2> Synthesis of 2-(5-chloro-2-nitrophenyl)dibenzo[b,e][1,4]dioxine

The 2-(dibenzo[b,e][1,4]dioxin-2-yl)-4,4,5,5-tetramethyl-1,3,2-dioxaborolane (73 g, 0.235 mol) obtained in <Step 1>, 2-bromo-4-chloro-1-nitrobenzene (67 g, 0.282 mol), and Pd(PPh$_3$)$_4$ (13.5 g, 0.011 mol) were put into a flask, a 2 M saturated aqueous solution of Na$_2$CO$_3$ (352 ml) and 1,4-dioxane (2 L) were added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(5-chloro-2-nitrophenyl)dibenzo[b,e][1,4]dioxine (72 g, yield 91%).

<Step 3> Synthesis of Compounds Inv3 and Inv4

The 2-(5-chloro-2-nitrophenyl)dibenzo[b,e][1,4]dioxine (72 g, 0.212 mol) obtained in <Step 2>, triphenylphosphine (67 g, 0.255 mol), and 1,2-dichlorobenzene (1 L) were mixed under nitrogen flow, and then the resulting mixture was stirred for 12 hours. After the reaction was terminated, 1,2-dichlorobenzene was removed, and an organic layer was extracted with dichloromethane. The obtained organic layer was dried over Na$_2$SO$_4$, distilled under reduced pressure, and then purified with column chromatography to obtain Compound Inv3 (35 g, yield 53%) and Compound Inv4 (23 g, yield 35%).

[Preparation Example 3] Synthesis of Compounds Inv5 and Inv6

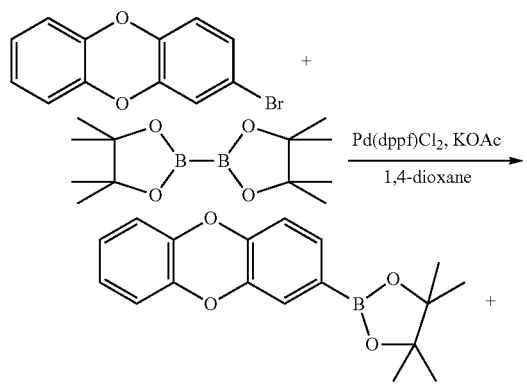

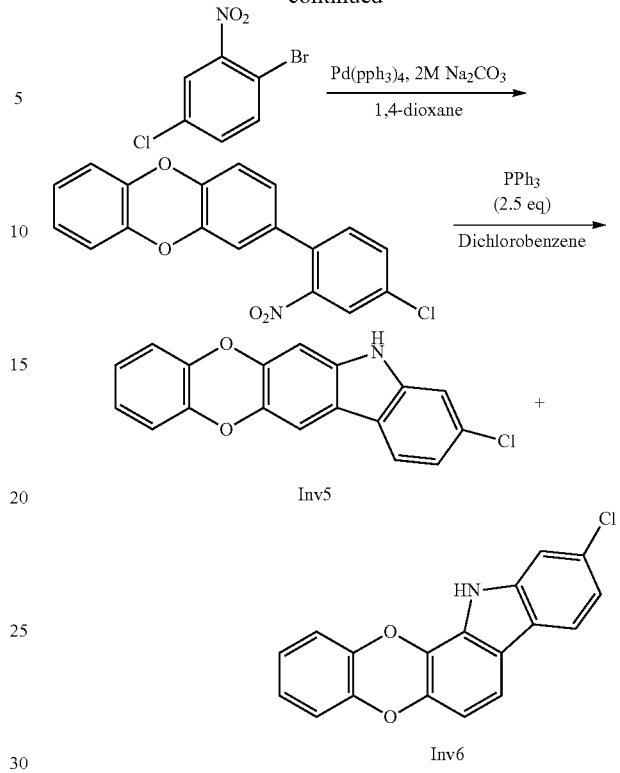

<Step 1> Synthesis of 2-(dibenzo[b,e][1,4]dioxin-2-yl)-4,4,5,5-tetramethyl-1,3,2-dioxaborolane 2-bromodibenzo[b,e][1,4]dioxine (100 g, 0.38 mol), bis(pinacolato)diboron (115.8 g, 0.46 mol), Pd(dppf)Cl$_2$ (31 g, 0.038 mol), and KOAc (111.9 g, 1.14 mol) were put into a flask, 1,4-dioxane (2 L) was added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(dibenzo[b,e][1,4]dioxin-2-yl)-4,4,5,5-tetramethyl-1,3,2-dioxaborolane (73 g, yield 62%).

<Step 2> Synthesis of 2-(4-chloro-2-nitrophenyl)dibenzo[b,e][1,4]dioxine

The 2-(dibenzo[b,e][1,4]dioxin-2-yl)-4,4,5,5-tetramethyl-1,3,2-dioxaborolane (73 g, 0.235 mol) obtained in <Step 1>, 1-bromo-4-chloro-2-nitrobenzene (67 g, 0.282 mol), and Pd(PPh$_3$)$_4$ (13.5 g, 0.011 mol) were put into a flask, a 2 M saturated aqueous solution of Na$_2$CO$_3$ (352 ml) and 1,4-dioxane (2 L) were added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(4-chloro-2-nitrophenyl)dibenzo[b,e][1,4]dioxine (72 g, yield 91%).

<Step 3> Synthesis of Compounds Inv5 and Inv6

The 2-(4-chloro-2-nitrophenyl)dibenzo[b,e][1,4]dioxine (72 g, 0.212 mol) obtained in <Step 2>, triphenylphosphine (67 g, 0.255 mol), and 1,2-dichlorobenzene (1 L) were mixed under nitrogen flow, and then the resulting mixture was stirred for 12 hours. After the reaction was terminated, 1,2-dichlorobenzene was removed, and an organic layer was extracted with dichloromethane. The obtained organic layer was dried over Na$_2$SO$_4$, distilled under reduced pressure, and then purified with column chromatography to obtain Compound Inv5 (35 g, yield 53%) and Compound Inv6 (23 g, yield 35%).

[Preparation Example 4] Synthesis of Compounds Inv7 and Inv8

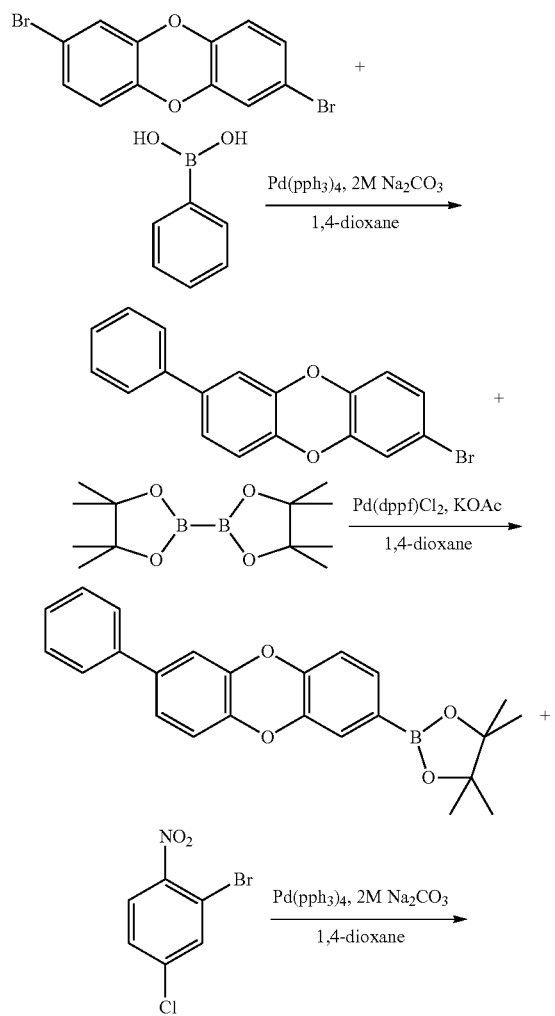

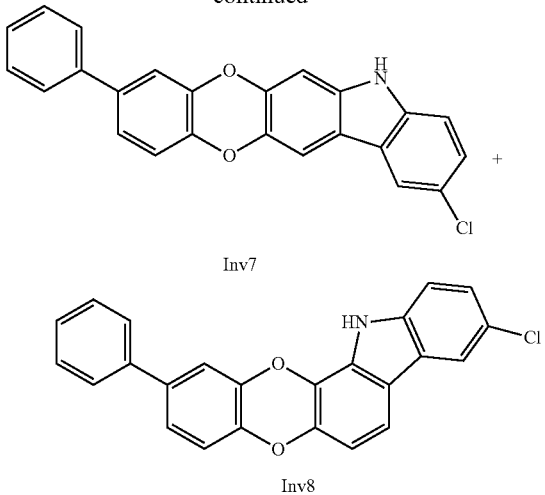

<Step 1> Synthesis of 2-bromo-7-phenyldibenzo[b,e][1,4]dioxine 2,7-dibromodibenzo[b,e][1,4]dioxine (137 g, 0.400 mol), phenylboronic acid (49 g, 0.400 mol), and Pd(dppf)Cl$_2$ (23.1 g, 0.02 mol) were put into a flask, a 2 M saturated aqueous solution of Na$_2$CO$_3$ (600 ml) and 1,4-dioxane (2 L) were added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-bromo-7-phenyldibenzo[b,e][1,4]dioxine (129 g, yield 95%).

<Step 2> Synthesis of 4,4,5,5-tetramethyl-2-(7-phenyldibenzo[b,e][1,4]dioxin-2-yl)-1,3,2-dioxaborolane The 2-bromo-7-phenyldibenzo[b,e][1,4]dioxine (129 g, 0.38 mol) obtained in <Step 1>, bis(pinacolato)diboron (115.8 g, 0.46 mol), Pd(dppf)Cl$_2$ (31 g, 0.038 mol), and KOAc (111.9 g, 1.14 mol) were put into a flask, 1,4-dioxane (2 L) was added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 4,4,5,5-tetramethyl-2-(7-phenyldibenzo[b,e][1,4]dioxin-2-yl)-1,3,2-dioxaborolane (91 g, yield 62%).

<Step 3> Synthesis of 2-(5-chloro-2-nitrophenyl)-7-phenyldibenzo[b,e][1,4]dioxine The 4,4,5,5-tetramethyl-2-(7-phenyldibenzo[b,e][1,4]dioxin-2-yl)-1,3,2-dioxaborolane (91 g, 0.235 mol) obtained in <Step 2>, 2-bromo-4-chloro-1-nitrobenzene (67 g, 0.282 mol), and Pd(PPh$_3$)$_4$ (13.5 g, 0.011 mol) were put into a flask, a 2 M saturated aqueous solution of Na$_2$CO$_3$ (352 ml) and 1,4-dioxane (2 L) were added thereto to dissolve the mixture, and then the resulting solution was heated and stirred for 8 hours. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain a compound 2-(5-chloro-2-nitrophenyl)-7-phenyldibenzo[b,e][1,4]dioxine (88 g, yield 91%).

<Step 4> Synthesis of Compounds Inv7 and Inv8

The 2-(5-chloro-2-nitrophenyl)-7-phenyldibenzo[b,e][1,4]dioxine (88 g, 0.212 mol) obtained in <Step 3>, triphenylphosphine (67 g, 0.255 mol), and 1,2-dichlorobenzene (1 L) were mixed under nitrogen flow, and then the resulting mixture was stirred for 12 hours. After the reaction was terminated, 1,2-dichlorobenzene was removed, and an organic layer was extracted with dichloromethane. The obtained organic layer was dried over Na$_2$SO$_4$, distilled under reduced pressure, and then purified with column chromatography to obtain Compound Inv7 (43 g, yield 53%) and Compound Inv8 (28 g, yield 35%).

[Synthesis Example 1] Synthesis of Cpd1

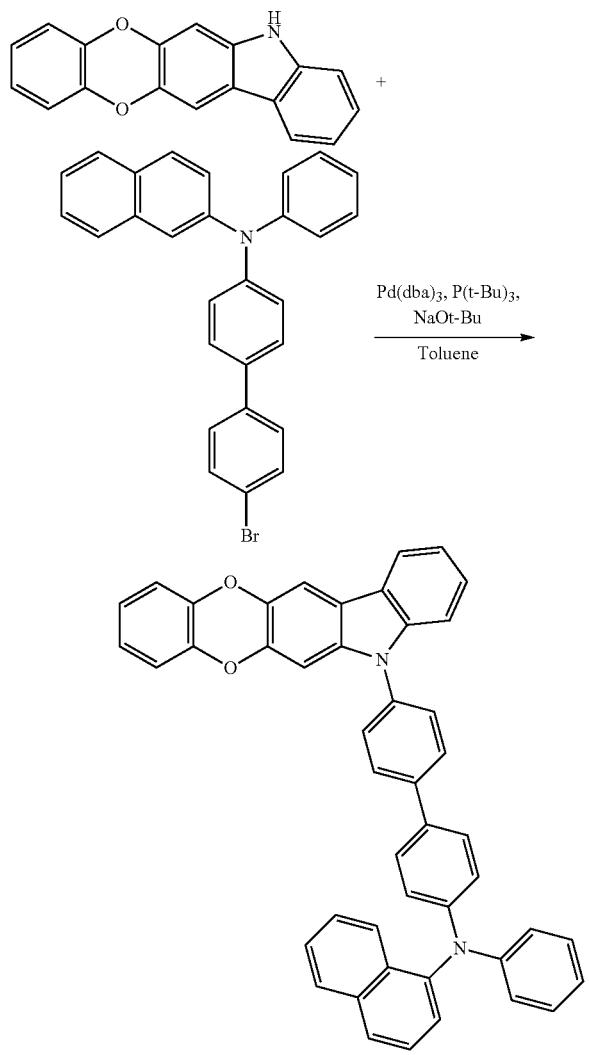

Compound Inv 1 (2.7 g, 10.0 mmol) synthesized in Preparation Example 1 and N-(4'-bromo-[1,1'-biphenyl]-4-yl)-N-phenylnaphthalen-2-amine (5.4 g, 12.0 mmol) were dissolved in 100 ml of toluene, and then Pd$_2$(dba)$_3$ (0.9 g, 1.0 mmol) was introduced thereto under nitrogen. Thereafter, NaOtBu (2.9 g, 30 mmol) was added thereto, (t-Bu)$_3$P (1.0 ml, 1.0 mmol) was introduced into the reaction solution, and then the mixture was refluxed and stirred for 5 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain Compound Cpd1 (5.5 g, yield 86%).

HRMS [M]$^+$: 642.230

[Synthesis Example 2] Synthesis of Cpd2

Compound Cpd2 (5.8 g, yield 85%) was obtained by performing the same process as in Synthesis Example 1, except that 7-bromo-9,9-dimethyl-N-(naphthalen-1-yl)-N-phenyl-9H-fluoren-2-amine (5.9 g, 12.0 mmol) was used instead of N-(4'-bromo-[1,1'-biphenyl]-4-yl)-N-phenylnaphthalen-2-amine used in Synthesis Example 1.

HRMS [M]$^+$: 682.262

[Synthesis Example 3] Synthesis of Cpd3

Compound Cpd3 (6.7 g, yield 85%) was obtained by performing the same process as in Synthesis Example 1, except that N,N-di([1,1'-biphenyl]-4-yl)-4'-bromo-[1,1'-biphenyl]-4-amine (6.6 g, 12.0 mmol) was used instead of N-(4'-bromo-[1,1'-biphenyl]-4-yl)-N-phenylnaphthalen-2-amine used in Synthesis Example 1.

HRMS [M]$^+$: 744.277

[Synthesis Example 4] Synthesis of Cpd4

Compound Cpd4 (6.7 g, yield 81%) was obtained by performing the same process as in Synthesis Example 1, except that N1-([1,1'-biphenyl]-4-yl)-N1-(4'-bromo-[1,1'-biphenyl]-4-yl)-N4,N4-diphenylbenzene-1,4-diamine (7.7 g, 12.0 mmol) was used instead of N-(4'-bromo-[1,1'-biphenyl]-4-yl)-N-phenylnaphthalen-2-amine used in Synthesis Example 1.

HRMS [M]$^+$: 835.319

[Synthesis Example 5] Synthesis of Cpd5

Compound Cpd5 (6.9 g, yield 88%) was obtained by performing the same process as in Synthesis Example 1, except that N-([1,1'-biphenyl]-4-yl)-N-(4'-bromo-[1,1'-biphenyl]-4-yl)-9,9-dimethyl-9H-fluoren-2-amine (7.1 g, 12.0 mmol) was used instead of N-(4'-bromo-[1,1'-biphenyl]-4-yl)-N-phenylnaphthalen-2-amine used in Synthesis Example 1.

HRMS [M]$^+$: 784.309

[Synthesis Example 6] Synthesis of Cpd6

Compound Cpd6 (7.0 g, yield 85%) was obtained by performing the same process as in Synthesis Example 1, except that N1-(4'-bromo-[1,1'-biphenyl]-4-yl)-N1-(9,9-dimethyl-9H-fluoren-2-yl)-N4,N4-diphenylbenzene-1,4-di-

93 amine (8.2 g, 12.0 mmol) was used instead of N-(4'-bromo-[1,1'-biphenyl]-4-yl)-N-phenylnaphthalen-2-amine used in Synthesis Example 1.

HRMS [M]+: 875.351

[Synthesis Example 7] Synthesis of Cpd7

Compound Cpd7 (5.7 g, yield 86%) was obtained by performing the same process as in Synthesis Example 1, except that N-([1,1'-biphenyl]-4-yl)-N-(4-bromophenyl)-[1,1'-biphenyl]-4-amine (5.7 g, 12.0 mmol) was used instead of N-(4'-bromo-[1,1'-biphenyl]-4-yl)-N-phenylnaphthalen-2-amine used in Synthesis Example 1.

HRMS [M]+: 668.246

[Synthesis Example 8] Synthesis of Cpd8

Compound Cpd8 (6.9 g, yield 85%) was obtained by performing the same process as in Synthesis Example 1, except that N,N-di([1,1'-biphenyl]-4-yl)-4"-chloro-[1,1':4',1"-terphenyl]-4-amine (7.0 g, 12.0 mmol) was used instead of N-(4'-bromo-[1,1'-biphenyl]-4-yl)-N-phenylnaphthalen-2-amine used in Synthesis Example 1.

HRMS [M]+: 820.309

[Synthesis Example 9] Synthesis of Cpd12

Compound Cpd12 (6.8 g, yield 80%) was obtained by performing the same process as in Synthesis Example 1, except that 4'-chloro-N,N-bis(4-(naphthalen-1-yl)phenyl)-[1,1'-biphenyl]-4-amine (7.3 g, 12.0 mmol) was used instead of N-(4'-bromo-[1,1'-biphenyl]-4-yl)-N-phenylnaphthalen-2-amine used in Synthesis Example 1.

HRMS [M]+: 844.309

[Synthesis Example 10] Synthesis of Cpd13

Compound Cpd13 (6.9 g, yield 84%) was obtained by performing the same process as in Synthesis Example 1, except that N-([1,1'-biphenyl]-4-yl)-N-(4-(5-(4-bromophenyl)thiophen-2-yl)phenyl)-[1,1'-biphenyl]-4-amine (7.6 g, 12.0 mmol) was used instead of N-(4'-bromo-[1,1'-biphenyl]-4-yl)-N-phenylnaphthalen-2-amine used in Synthesis Example 1.

HRMS [M]+: 826.265

[Synthesis Example 11] Synthesis of Cpd14

Compound Cpd14 (7.0 g, yield 86%) was obtained by performing the same process as in Synthesis Example 1, except that N-([1,1'-biphenyl]-4-yl)-N-(4-(5-(4-chlorophenyl)furan-2-yl)phenyl)-[1,1'-biphenyl]-4-amine (6.9 g, 12.0 mmol) was used instead of N-(4'-bromo-[1,1'-biphenyl]-4-yl)-N-phenylnaphthalen-2-amine used in Synthesis Example 1.

HRMS [M]+: 810.288

[Synthesis Example 12] Synthesis of Cpd15

Compound Cpd15 (6.4 g, yield 89%) was obtained by performing the same process as in Synthesis Example 1, except that N,N-di([1,1'-biphenyl]-4-yl)-6-bromonaphthalen-2-amine (6.3 g, 12.0 mmol) was used instead of N-(4'-bromo-[1,1'-biphenyl]-4-yl)-N-phenylnaphthalen-2-amine used in Synthesis Example 1.

HRMS [M]+: 718.262

[Synthesis Example 13] Synthesis of Cpd16

Compound Cpd16 (6.4 g, yield 83%) was obtained by performing the same process as in Synthesis Example 1, except that N-([1,1'-biphenyl]-4-yl)-N-(4'-bromo-[1,1'-biphenyl]-4-yl)phenanthren-9-amine (6.9 g, 12.0 mmol) was used instead of N-(4'-bromo-[1,1'-biphenyl]-4-yl)-N-phenylnaphthalen-2-amine used in Synthesis Example 1.

HRMS [M]+: 867.277

[Synthesis Example 14] Synthesis of Cpd17

Compound Cpd17 (6.8 g, yield 85%) was obtained by performing the same process as in Synthesis Example 1, except that N-(4'-bromo-[1,1'-biphenyl]-4-yl)-N-(9,9-dimethyl-9H-fluoren-2-yl)phenanthren-2-amine (7.4 g, 12.0 mmol) was used instead of N-(4'-bromo-[1,1'-biphenyl]-4-yl)-N-phenylnaphthalen-2-amine used in Synthesis Example 1.

HRMS [M]+: 808.309

[Synthesis Example 15] Synthesis of Cpd18

Compound Cpd18 (6.5 g, yield 88%) was obtained by performing the same process as in Synthesis Example 1, except that N-(4'-bromo-[1,1'-biphenyl]-4-yl)-N-phenyl-[1,1':4',1"-terphenyl]-4-amine (6.6 g, 12.0 mmol) was used instead of N-(4'-bromo-[1,1'-biphenyl]-4-yl)-N-phenylnaphthalen-2-amine used in Synthesis Example 1.

HRMS [M]+: 744.277

[Synthesis Example 16] Synthesis of Cpd22

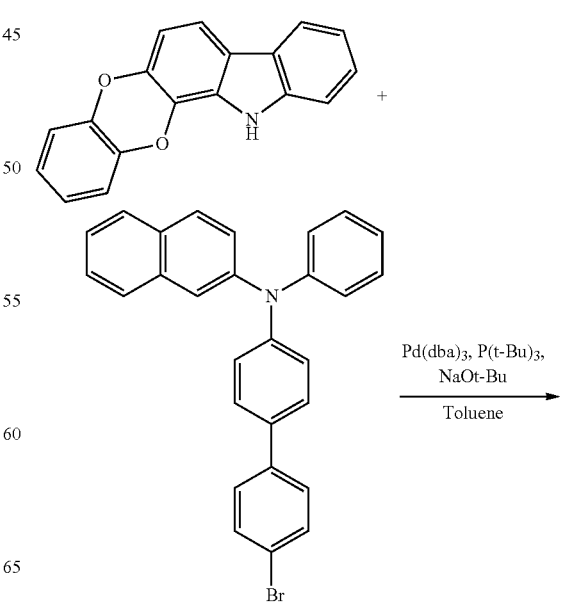

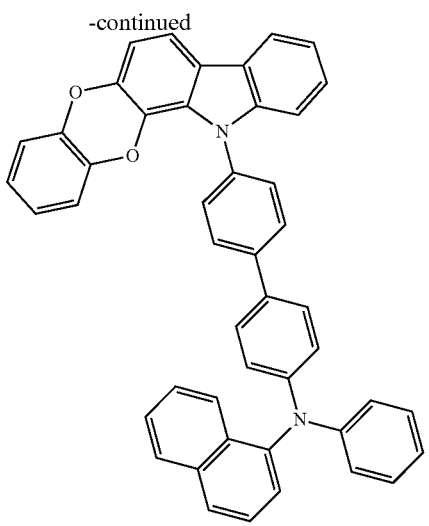

Compound Inv 2 (2.7 g, 10.0 mmol) synthesized in Preparation Example 1 and N-(4'-bromo-[1,1'-biphenyl]-4-yl)-N-phenylnaphthalen-2-amine (5.4 g, 12.0 mmol) were dissolved in toluene (100 ml), and then Pd$_2$(dba)$_3$ (0.9 g, 1.0 mmol) was introduced thereto under nitrogen. Thereafter, NaOtBu (2.9 g, 30 mmol) was added thereto, (t-Bu)$_3$P (1.0 ml, 1.0 mmol) was introduced into the reaction solution, and then the mixture was refluxed and stirred for 5 hours. After it was confirmed by TLC that the reaction was terminated, the temperature was cooled to normal temperature. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain Compound Cpd22 (5.5 g, yield 86%).

HRMS [M]$^+$: 642.230

[Synthesis Example 17] Synthesis of Cpd23

Compound Cpd23 (5.8 g, yield 85%) was obtained by performing the same process as in Synthesis Example 16, except that 7-bromo-9,9-dimethyl-N-(naphthalen-1-yl)-N-phenyl-9H-fluoren-2-amine (5.9 g, 12.0 mmol) was used instead of N-(4'-bromo-[1,1'-biphenyl]-4-yl)-N-phenylnaphthalen-2-amine used in Synthesis Example 16.

HRMS [M]$^+$: 682.262

[Synthesis Example 18] Synthesis of Cpd24

Compound Cpd24 (6.7 g, yield 85%) was obtained by performing the same process as in Synthesis Example 16, except that N,N-di([1,1'-biphenyl]-4-yl)-4'-bromo-[1,1'-biphenyl]-4-amine (6.6 g, 12.0 mmol) was used instead of N-(4'-bromo-[1,1'-biphenyl]-4-yl)-N-phenylnaphthalen-2-amine used in Synthesis Example 16.

HRMS [M]$^+$: 744.277

[Synthesis Example 19] Synthesis of Cpd25

Compound Cpd25 (6.7 g, yield 81%) was obtained by performing the same process as in Synthesis Example 16, except that N1-([1,1'-biphenyl]-4-yl)-N1-(4'-bromo-[1,1'-biphenyl]-4-yl)-N4,N4-diphenylbenzene-1,4-diamine (7.7 g, 12.0 mmol) was used instead of N-(4'-bromo-[1,1'-biphenyl]-4-yl)-N-phenylnaphthalen-2-amine used in Synthesis Example 16.

HRMS [M]$^+$: 835.319

[Synthesis Example 20] Synthesis of Cpd26

Compound Cpd26 (6.9 g, yield 88%) was obtained by performing the same process as in Synthesis Example 16, except that N-([1,1'-biphenyl]-4-yl)-N-(4'-bromo-[1,1'-biphenyl]-4-yl)-9,9-dimethyl-9H-fluoren-2-amine (7.1 g, 12.0 mmol) was used instead of N-(4'-bromo-[1,1'-biphenyl]-4-yl)-N-phenylnaphthalen-2-amine used in Synthesis Example 16.

HRMS [M]$^+$: 784.309

[Synthesis Example 21] Synthesis of Cpd27

Compound Cpd27 (7.0 g, yield 85%) was obtained by performing the same process as in Synthesis Example 16, except that N1-(4'-bromo-[1,1'-biphenyl]-4-yl)-N1-(9,9-dimethyl-9H-fluoren-2-yl)-N4,N4-diphenylbenzene-1,4-diamine (8.2 g, 12.0 mmol) was used instead of N-(4'-bromo-[1,1'-biphenyl]-4-yl)-N-phenylnaphthalen-2-amine used in Synthesis Example 16.

HRMS [M]$^+$: 875.351

[Synthesis Example 22] Synthesis of Cpd28

Compound Cpd28 (5.7 g, yield 86%) was obtained by performing the same process as in Synthesis Example 16, except that N-([1,1'-biphenyl]-4-yl)-N-(4-bromophenyl)-[1,1'-biphenyl]-4-amine (5.7 g, 12.0 mmol) was used instead of N-(4'-bromo-[1,1'-biphenyl]-4-yl)-N-phenylnaphthalen-2-amine used in Synthesis Example 16.

HRMS [M]$^+$: 668.246

[Synthesis Example 23] Synthesis of Cpd29

Compound Cpd29 (6.9 g, yield 85%) was obtained by performing the same process as in Synthesis Example 16, except that N,N-di([1,1'-biphenyl]-4-yl)-4''-chloro-[1,1':4',1''-terphenyl]-4-amine (7.0 g, 12.0 mmol) was used instead of N-(4'-bromo-[1,1'-biphenyl]-4-yl)-N-phenylnaphthalen-2-amine used in Synthesis Example 16.

HRMS [M]$^+$: 820.309

[Synthesis Example 24] Synthesis of Cpd33

Compound Cpd33 (6.8 g, yield 80%) was obtained by performing the same process as in Synthesis Example 16, except that 4'-chloro-N,N-bis(4-(naphthalen-1-yl)phenyl)-[1,1'-biphenyl]-4-amine (7.3 g, 12.0 mmol) was used instead of N-(4'-bromo-[1,1'-biphenyl]-4-yl)-N-phenylnaphthalen-2-amine used in Synthesis Example 16.

HRMS [M]$^+$: 844.309

[Synthesis Example 25] Synthesis of Cpd34

Compound Cpd34 (6.9 g, yield 84%) was obtained by performing the same process as in Synthesis Example 16, except that N-([1,1'-biphenyl]-4-yl)-N-(4-(5-(4-bromophenyl)thiophen-2-yl)phenyl)-[1,1'-biphenyl]-4-amine (7.6 g, 12.0 mmol) was used instead of N-(4'-bromo-[1,1'-biphenyl]-4-yl)-N-phenylnaphthalen-2-amine used in Synthesis Example 16.

HRMS [M]$^+$: 826.265

[Synthesis Example 26] Synthesis of Cpd35

Compound Cpd35 (7.0 g, yield 86%) was obtained by performing the same process as in Synthesis Example 16, except that N-([1,1'-biphenyl]-4-yl)-N-(4-(5-(4-chlorophenyl)furan-2-yl)phenyl)-[1,1'-biphenyl]-4-amine (6.9 g, 12.0 mmol) was used instead of N-(4'-bromo-[1,1'-biphenyl]-4-yl)-N-phenylnaphthalen-2-amine used in Synthesis Example 16.

HRMS [M]+: 810.288

[Synthesis Example 27] Synthesis of Cpd36

Compound Cpd36 (6.4 g, yield 89%) was obtained by performing the same process as in Synthesis Example 16, except that N,N-di([1,1'-biphenyl]-4-yl)-6-bromonaphthalen-2-amine (6.3 g, 12.0 mmol) was used instead of N-(4'-bromo-[1,1'-biphenyl]-4-yl)-N-phenylnaphthalen-2-amine used in Synthesis Example 16.

HRMS [M]+: 718.262

[Synthesis Example 28] Synthesis of Cpd37

Compound Cpd37 (6.4 g, yield 83%) was obtained by performing the same process as in Synthesis Example 16, except that N-([1,1'-biphenyl]-4-yl)-N-(4'-bromo-[1,1'-biphenyl]-4-yl)phenanthren-9-amine (6.9 g, 12.0 mmol) was used instead of N-(4'-bromo-[1,1'-biphenyl]-4-yl)-N-phenylnaphthalen-2-amine used in Synthesis Example 16.

HRMS [M]+: 867.277

[Synthesis Example 29] Synthesis of Cpd38

Compound Cpd38 (6.8 g, yield 85%) was obtained by performing the same process as in Synthesis Example 16, except that N-(4'-bromo-[1,1'-biphenyl]-4-yl)-N-(9,9-dimethyl-9H-fluoren-2-yl)phenanthren-2-amine (7.4 g, 12.0 mmol) was used instead of N-(4'-bromo-[1,1'-biphenyl]-4-yl)-N-phenylnaphthalen-2-amine used in Synthesis Example 16.

HRMS [M]+: 808.309

[Synthesis Example 30] Synthesis of Cpd39

Compound Cpd39 (6.5 g, yield 88%) was obtained by performing the same process as in Synthesis Example 16, except that N-(4'-bromo-[1,1'-biphenyl]-4-yl)-N-phenyl-[1,1':4',1''-terphenyl]-4-amine (6.6 g, 12.0 mmol) was used instead of N-(4'-bromo-[1,1'-biphenyl]-4-yl)-N-phenylnaphthalen-2-amine used in Synthesis Example 16.

HRMS [M]+: 744.277

[Synthesis Example 31] Synthesis of Cpd19

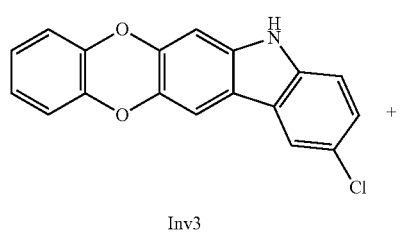

Inv3

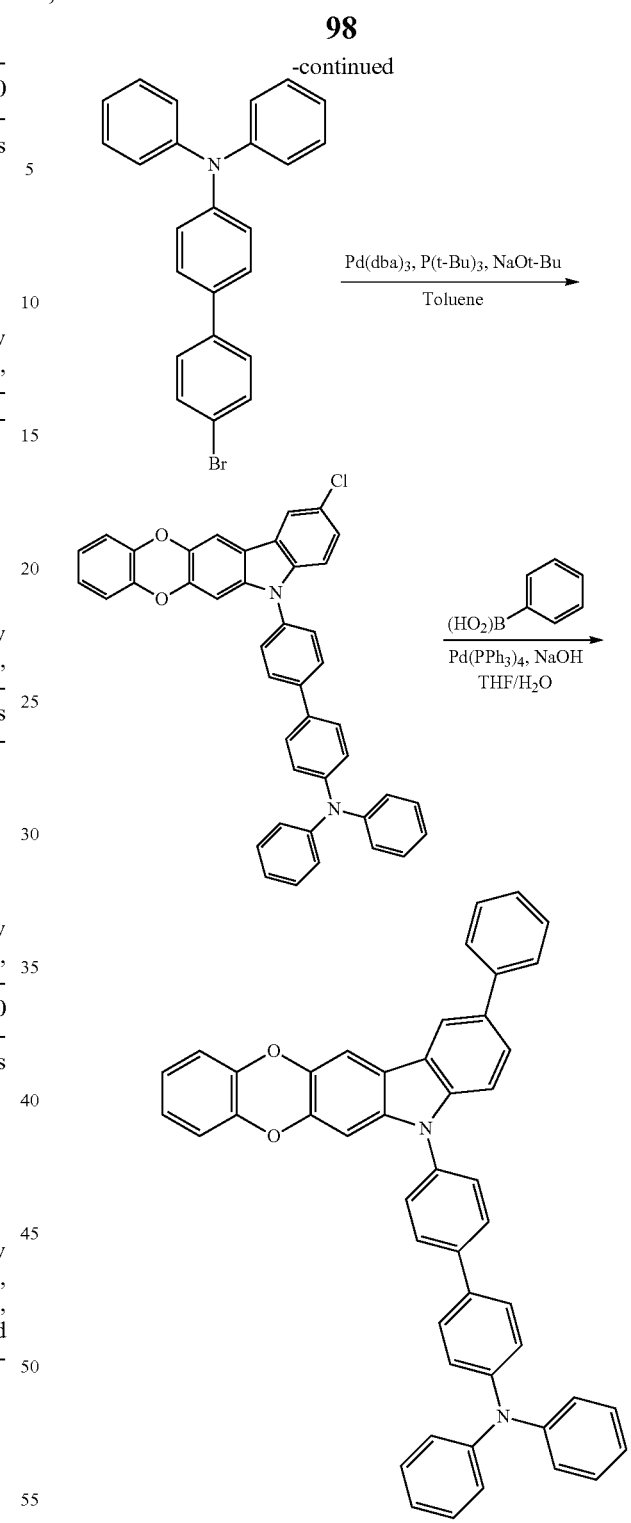

<Step 1> Synthesis of 2-(dibenzo[b,e][1,4]dioxin-2-yl)-4,4,5,5-tetramethyl-1,3,2-dioxaborolane Compound Inv 3 (3.1 g, 10.0 mmol) synthesized in Preparation Example 2 and 4'-bromo-N,N-diphenyl-[1,1'-biphenyl]-4-amine (4.8 g, 12.0 mmol) were dissolved in toluene (100 ml), and then Pd$_2$(dba)$_3$ (0.9 g, 1.0 mmol) was introduced thereto under nitrogen. Thereafter, NaOtBu (2.9 g, 30 mmol) was added thereto, (t-Bu)$_3$P (1.0 ml, 1.0 mmol)

was introduced into the reaction solution, and then the mixture was refluxed and stirred for 5 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over $Na_2SO_4$, distilled under reduced pressure, and then purified with column chromatography to obtain a compound 4'-(2-chloro-5H-benzo[5,6][1,4]dioxino[2,3-b]carbazol-5-yl)-N,N-diphenyl-[1,1'-biphenyl]-4-amine (4.8 g, yield 77%).

<Step 2> Synthesis of Cpd19

The 4'-(2-chloro-5H-benzo[5,6][1,4]dioxino[2,3-b]carbazol-5-yl)-N,N-diphenyl-[1,1'-biphenyl]-4-amine (4.8 g, 7.70 mmol) obtained in <Step 1>, phenylboronic acid (1.18 g, 9.67 mmol), NaOH (1.06 g, 26.4 mmol), and $THF/H_2O$ (100 ml/50 ml) were put into a flask, and the resulting mixture was stirred. Thereafter, $Pd(PPh_3)_4$ (5 mol %, 0.51 g) was added thereto at 40° C., and the resulting mixture was stirred at 80° C. for 12 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over $Na_2SO_4$, distilled under reduced pressure, and then purified with column chromatography to obtain Compound Cpd19 (4.1 g, yield 80%).

HRMS $[M]^+$: 668.246

[Synthesis Example 32] Synthesis of Cpd21

Compound Cpd21 (5.3 g, yield 64%) was obtained by performing the same process as in Synthesis Example 31, except that N,N-di([1,1'-biphenyl]-4-yl)-4'-bromo-[1,1'-biphenyl]-4-amine (6.6 g, 12.0 mmol) was used instead of 4'-bromo-N,N-diphenyl-[1,1'-biphenyl]-4-amine used in Synthesis Example 31.

HRMS $[M]^+$: 820.309

[Synthesis Example 33] Synthesis of Cpd40

Compound Cpd40 (4.1 g, yield 65%) was obtained by performing the same process as in Synthesis Example 31, except that Compound Inv 4 (3.1 g, 10.0 mmol) synthesized in Preparation Example 2 was used instead of Compound Inv 3 used in Synthesis Example 31.

HRMS $[M]^+$: 668.246

[Synthesis Example 34] Synthesis of Cpd42

Compound Cpd42 (4.9 g, yield 60%) was obtained by performing the same process as in Synthesis Example 32, except that Compound Inv 4 (3.1 g, 10.0 mmol) synthesized in Preparation Example 2 was used instead of Compound Inv 3 used in Synthesis Example 32.

HRMS $[M]^+$: 820.309

[Synthesis Example 35] Synthesis of Cpd46

Compound Cpd46 (4.5 g, yield 60%) was obtained by performing the same process as in Synthesis Example 31, except that iodobenzene (2.4 g, 12.0 mmol) and N-([1,1'-biphenyl]-4-yl)-N-(4-(4,4,5,5-tetramethyl-1,3,2-dioxaborolan-2-yl)phenyl)-[1,1'-biphenyl]-4-amine (5.1 g, 9.67 mmol) were used instead of 4'-bromo-N,N-diphenyl-[1,1'-biphenyl]-4-amine and phenylboronic acid used in Synthesis Example 31, respectively.

HRMS $[M]^+$: 744.277

[Synthesis Example 36] Synthesis of Cpd47

Compound Cpd47 (4.5 g, yield 58%) was obtained by performing the same process as in Synthesis Example 31, except that iodobenzene (2.4 g, 12.0 mmol) and N-([1,1'-biphenyl]-4-yl)-9,9-dimethyl-N-(4-(4,4,5,5-tetramethyl-1,3,2-dioxaborolan-2-yl)phenyl)-9H-fluoren-2-amine (5.4 g, 9.67 mmol) were used instead of 4'-bromo-N,N-diphenyl-[1,1'-biphenyl]-4-amine and phenylboronic acid used in Synthesis Example 31, respectively.

HRMS $[M]^+$: 784.309

[Synthesis Example 37] Synthesis of Cpd49

Compound Cpd49 (5.2 g, yield 63%) was obtained by performing the same process as in Synthesis Example 31, except that iodobenzene (2.4 g, 12.0 mmol) and N,N-di([1,1'-biphenyl]-4-yl)-4'-(4,4,5,5-tetramethyl-1,3,2-dioxaborolan-2-yl)-[1,1'-biphenyl]-4-amine (5.8 g, 9.67 mmol) were used instead of 4'-bromo-N,N-diphenyl-[1,1'-biphenyl]-4-amine and phenylboronic acid used in Synthesis Example 31, respectively.

HRMS $[M]^+$: 820.309

[Synthesis Example 38] Synthesis of Cpd51

Compound Cpd51 (5.6 g, yield 68%) was obtained by performing the same process as in Synthesis Example 31, except that 4-bromo-1,1'-biphenyl (2.8 g, 12.0 mmol) and N-([1,1'-biphenyl]-4-yl)-N-(4-(4,4,5,5-tetramethyl-1,3,2-dioxaborolan-2-yl)phenyl)-[1,1'-biphenyl]-4-amine (5.1 g, 9.67 mmol) were used instead of 4'-bromo-N,N-diphenyl-[1,1'-biphenyl]-4-amine and phenylboronic acid used in Synthesis Example 31, respectively.

HRMS $[M]^+$: 820.309

[Synthesis Example 39] Synthesis of Cpd52

Compound Cpd52 (4.6 g, yield 57%) was obtained by performing the same process as in Synthesis Example 31, except that iodobenzene (2.4 g, 12.0 mmol) and N-(9,9-dimethyl-9H-fluoren-2-yl)-N-(4-(4,4,5,5-tetramethyl-1,3,2-dioxaborolan-2-yl)phenyl)phenanthren-2-amine (5.7 g, 9.67 mmol) were used instead of 4'-bromo-N,N-diphenyl-[1,1'-biphenyl]-4-amine and phenylboronic acid used in Synthesis Example 31, respectively.

HRMS $[M]^+$: 808.309

[Synthesis Example 40] Synthesis of Cpd54

Compound Cpd54 (4.5 g, yield 60%) was obtained by performing the same process as in Synthesis Example 35, except that Compound Inv 5 (3.1 g, 10.0 mmol) synthesized in Preparation Example 3 was used instead of Compound Inv 3 used in Synthesis Example 35.

HRMS $[M]^+$: 744.277

[Synthesis Example 41] Synthesis of Cpd55

Compound Cpd55 (4.5 g, yield 58%) was obtained by performing the same process as in Synthesis Example 36, except that Compound Inv 5 (3.1 g, 10.0 mmol) synthesized in Preparation Example 3 was used instead of Compound Inv 3 used in Synthesis Example 36.
HRMS [M]$^+$: 784.309

[Synthesis Example 42] Synthesis of Cpd57

Compound Cpd57 (5.2 g, yield 63%) was obtained by performing the same process as in Synthesis Example 37, except that Compound Inv 5 (3.1 g, 10.0 mmol) synthesized in Preparation Example 3 was used instead of Compound Inv 3 used in Synthesis Example 37.
HRMS [M]$^+$: 820.309

[Synthesis Example 43] Synthesis of Cpd60

Compound Cpd60 (4.6 g, yield 57%) was obtained by performing the same process as in Synthesis Example 39, except that Compound Inv 5 (3.1 g, 10.0 mmol) synthesized in Preparation Example 3 was used instead of Compound Inv 3 used in Synthesis Example 39.
HRMS [M]$^+$: 808.309

[Synthesis Example 44] Synthesis of Cpd70

Compound Cpd70 (4.5 g, yield 60%) was obtained by performing the same process as in Synthesis Example 35, except that Compound Inv 4 (3.1 g, 10.0 mmol) synthesized in Preparation Example 2 was used instead of Compound Inv 3 used in Synthesis Example 35.
HRMS [M]$^+$: 744.277

[Synthesis Example 45] Synthesis of Cpd71

Compound Cpd71 (4.5 g, yield 58%) was obtained by performing the same process as in Synthesis Example 36, except that Compound Inv 4 (3.1 g, 10.0 mmol) synthesized in Preparation Example 2 was used instead of Compound Inv 3 used in Synthesis Example 36.
HRMS [M]$^+$: 784.309

[Synthesis Example 46] Synthesis of Cpd73

Compound Cpd73 (5.2 g, yield 63%) was obtained by performing the same process as in Synthesis Example 37, except that Compound Inv 4 (3.1 g, 10.0 mmol) synthesized in Preparation Example 2 was used instead of Compound Inv 3 used in Synthesis Example 37.
HRMS [M]$^+$: 820.309

[Synthesis Example 47] Synthesis of Cpd75

Compound Cpd75 (5.6 g, yield 68%) was obtained by performing the same process as in Synthesis Example 38, except that Compound Inv 4 (3.1 g, 10.0 mmol) synthesized in Preparation Example 2 was used instead of Compound Inv 3 used in Synthesis Example 38.
HRMS [M]$^+$: 820.309

[Synthesis Example 48] Synthesis of Cpd76

Compound Cpd76 (4.6 g, yield 57%) was obtained by performing the same process as in Synthesis Example 39, except that Compound Inv 4 (3.1 g, 10.0 mmol) synthesized in Preparation Example 2 was used instead of Compound Inv 3 used in Synthesis Example 39.
HRMS [M]$^+$: 808.309

[Synthesis Example 49] Synthesis of Cpd77

Compound Cpd77 (4.5 g, yield 60%) was obtained by performing the same process as in Synthesis Example 35, except that Compound Inv 6 (3.1 g, 10.0 mmol) synthesized in Preparation Example 3 was used instead of Compound Inv 3 used in Synthesis Example 35.
HRMS [M]$^+$: 744.277

[Synthesis Example 50] Synthesis of Cpd78

Compound Cpd78 (4.5 g, yield 58%) was obtained by performing the same process as in Synthesis Example 36, except that Compound Inv 6 (3.1 g, 10.0 mmol) synthesized in Preparation Example 3 was used instead of Compound Inv 3 used in Synthesis Example 36.
HRMS [M]$^+$: 784.309

[Synthesis Example 51] Synthesis of Cpd80

Compound Cpd80 (5.2 g, yield 63%) was obtained by performing the same process as in Synthesis Example 37, except that Compound Inv 6 (3.1 g, 10.0 mmol) synthesized in Preparation Example 3 was used instead of Compound Inv 3 used in Synthesis Example 37.
HRMS [M]$^+$: 820.309

[Synthesis Example 52] Synthesis of Cpd81

Compound Cpd81 (4.6 g, yield 57%) was obtained by performing the same process as in Synthesis Example 39, except that Compound Inv 6 (3.1 g, 10.0 mmol) synthesized in Preparation Example 3 was used instead of Compound Inv 3 used in Synthesis Example 39.
HRMS [M]$^+$: 808.309

[Synthesis Example 53] Synthesis of Cpd20

Compound Cpd20 (4.6 g, yield 65%) was obtained by performing the same process as in Synthesis Example 31, except that Compound Inv 7 (3.8 g, 10.0 mmol) and N-(4'-bromo-[1,1'-biphenyl]-4-yl)-N-phenylnaphthalen-2-amine (5.4 g, 12.0 mmol) synthesized in Preparation Example 4 were used instead of Compound Inv 3 and 4'-bromo-N,N-diphenyl-[1,1'-biphenyl]-4-amine used in Synthesis Example 31, respectively.
HRMS [M]$^+$: 794.293

[Synthesis Example 54] Synthesis of Cpd41

Compound Cpd41 (4.6 g, yield 65%) was obtained by performing the same process as in Synthesis Example 53, except that Compound Inv 8 (3.8 g, 10.0 mmol) synthesized in Preparation Example 4 was used instead of Inv 7 used in Synthesis Example 31.
HRMS [M]$^+$: 794.293

[Synthesis Example 55] Synthesis of Cpd48

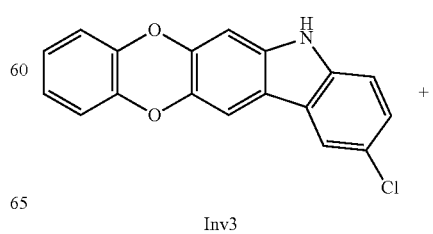

Inv3

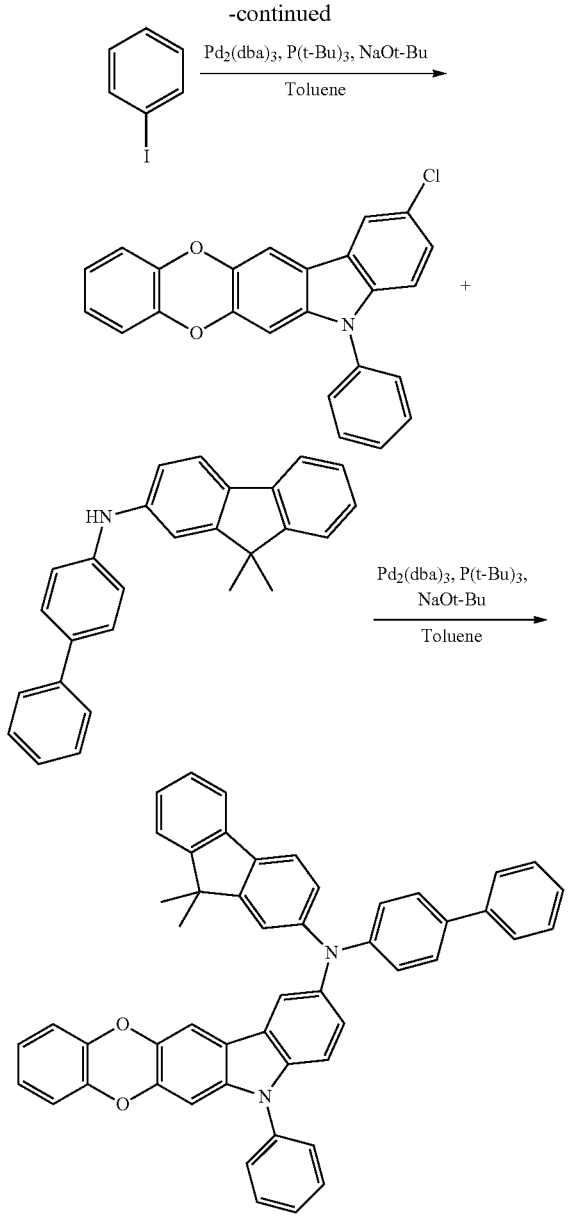

<Step 1> Synthesis of 2-(dibenzo[b,e][1,4]dioxin-2-yl)-4,4,5,5-tetramethyl-1,3,2-dioxaborolane Compound Inv 3 (3.1 g, 10.0 mmol) synthesized in Preparation Example 2 and iodobenzene (2.5 g, 12.0 mmol) were dissolved in toluene (100 ml), and then Pd$_2$(dba)$_3$ (0.9 g, 1.0 mmol) was introduced thereto under nitrogen. Thereafter, NaOtBu (2.9 g, 30 mmol) was added thereto, (t-Bu)$_3$P (1.0 ml, 1.0 mmol) was introduced into the reaction solution, and then the mixture was refluxed and stirred for 5 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain 2-chloro-5-phenyl-5H-benzo[5,6][1,4]dioxino[2,3-b]carbazole (3.3 g, yield 83%).

<Step 2> Synthesis of Cpd48

The 2-chloro-5-phenyl-5H-benzo[5,6][1,4]dioxino[2,3-b]carbazole (3.3 g, 8.5 mmol) obtained in <Step 1> and N-([1,1'-biphenyl]-4-yl)-9,9-dimethyl-9H-fluoren-2-amine (3.7 g, 10.2 mmol) were dissolved in toluene (85 ml), and then Pd$_2$(dba)$_3$ (0.76 g, 0.8 mmol) was introduced thereinto under nitrogen. Thereafter, NaOtBu (2.4 g, 25 mmol) was added thereto, (t-Bu)$_3$P (0.8 ml, 0.8 mmol) was introduced into the reaction solution, and then the mixture was refluxed and stirred for 5 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over Na$_2$SO$_4$, distilled under reduced pressure, and then purified with column chromatography to obtain Compound Cpd48 (4.8 g, yield 80%).

HRMS [M]$^+$: 708.277

[Synthesis Example 56] Synthesis of Cpd56

Compound Cpd56 (4.6 g, yield 65%) was obtained by performing the same process as in Synthesis Example 55, except that Compound Inv 5 (3.1 g, 10.0 mmol) synthesized in Preparation Example 3 was used instead of Compound Inv 3 used in Synthesis Example 55.

HRMS [M]$^+$: 708.277

[Synthesis Example 57] Synthesis of Cpd72

Compound Cpd72 (4.3 g, yield 61%) was obtained by performing the same process as in Synthesis Example 55, except that Compound Inv 4 (3.1 g, 10.0 mmol) synthesized in Preparation Example 3 was used instead of Compound Inv 3 used in Synthesis Example 55.

HRMS [M]$^+$: 708.277

[Synthesis Example 58] Synthesis of Cpd79

Compound Cpd79 (4.2 g, yield 60%) was obtained by performing the same process as in Synthesis Example 55, except that Compound Inv 6 (3.1 g, 10.0 mmol) synthesized in Preparation Example 3 was used instead of Compound Inv 3 used in Synthesis Example 55.

HRMS [M]$^+$: 708.277

[Synthesis Example 59] Synthesis of Cpd86

Compound Inv 1 (2.7 g, 10.0 mmol) synthesized in Preparation Example 1, 2-chloro-4,6-diphenyl-1,3,5-triazine (2.67 g, 10.0 mmol), NaH (0.24 g, 10.0 mmol), and DMF (50 ml) were mixed, and the resulting mixture was stirred at normal temperature for 1 hour. After the reaction was terminated, water was added thereto, and a solid product was filtered and then purified with column chromatography to obtain Compound Cpd86 (4.7 g, yield 93%).

HRMS [M]$^+$: 504.158

[Synthesis Example 60] Synthesis of Cpd87

Compound Cpd87 (4.3 g, yield 85%) was obtained by performing the same process as in Synthesis Example 59, except that 2-chloro-4,6-diphenylpyridine (2.6 g, 10.0 mmol) was used instead of 2-chloro-4,6-diphenyl-1,3,5-triazine used in Synthesis Example 59.
HRMS [M]+: 502.168

[Synthesis Example 61] Synthesis of Cpd88

Compound Cpd88 (4.4 g, yield 88%) was obtained by performing the same process as in Synthesis Example 59, except that 4-bromo-2,6-diphenylpyrimidine (3.1 g, 10.0 mmol) was used instead of 2-chloro-4,6-diphenyl-1,3,5-triazine used in Synthesis Example 59.
HRMS [M]+: 503.163

[Synthesis Example 62] Synthesis of Cpd89

Compound Cpd89 (4.5 g, yield 88%) was obtained by performing the same process as in Synthesis Example 59, except that 2-bromo-4,6-diphenylpyrimidine (3.1 g, 10.0 mmol) was used instead of 2-chloro-4,6-diphenyl-1,3,5-triazine used in Synthesis Example 59.
HRMS [M]+: 503.163

[Synthesis Example 63] Synthesis of Cpd128

Compound Cpd128 (4.5 g, yield 88%) was obtained by performing the same process as in Synthesis Example 59, except that Compound Inv 2 (2.7 g, 10.0 mmol) synthesized in Preparation Example 1 was used instead of Compound Inv 1 used in Synthesis Example 59.
HRMS [M]+: 504.158

[Synthesis Example 64] Synthesis of Cpd129

Compound Cpd129 (4.3 g, yield 85%) was obtained by performing the same process as in Synthesis Example 60, except that Compound Inv 2 (2.7 g, 10.0 mmol) synthesized in Preparation Example 1 was used instead of Compound Inv 1 used in Synthesis Example 60.
HRMS [M]+: 502.168

[Synthesis Example 65] Synthesis of Cpd130

Compound Cpd130 (4.4 g, yield 88%) was obtained by performing the same process as in Synthesis Example 61, except that Compound Inv 2 (2.7 g, 10.0 mmol) synthesized in Preparation Example 1 was used instead of Compound Inv 1 used in Synthesis Example 61.
HRMS [M]+: 503.163

[Synthesis Example 66] Synthesis of Cpd131

Compound Cpd131 (4.5 g, yield 88%) was obtained by performing the same process as in Synthesis Example 62, except that Compound Inv 2 (2.7 g, 10.0 mmol) synthesized in Preparation Example 1 was used instead of Compound Inv 1 used in Synthesis Example 62.
HRMS [M]+: 503.163

[Synthesis Example 67] Synthesis of Cpd90

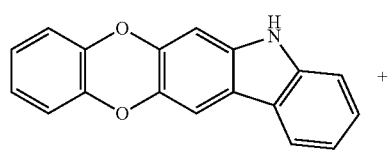
+

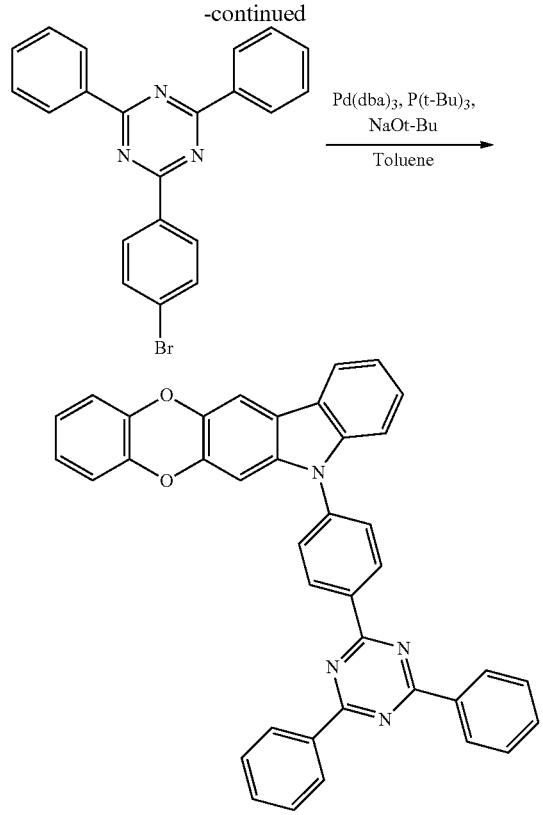

Compound Inv 1 (2.7 g, 10.0 mmol) synthesized in Preparation Example 1 and 2-(4-bromophenyl)-4,6-diphenyl-1,3,5-triazine (4.7 g, 12.0 mmol) were dissolved in toluene (100 ml), and then Pd2(dba)3 (0.9 g, 1.0 mmol) was introduced thereto under nitrogen. Thereafter, NaOtBu (2.9 g, 30 mmol) was added thereto, (t-Bu)3P (1.0 ml, 1.0 mmol) was introduced into the reaction solution, and then the mixture was refluxed and stirred for 5 hours.

After it was confirmed by TLC that the reaction was terminated, the temperature was cooled to normal temperature. After the reaction was terminated, distilled water was added thereto, and an organic layer was extracted with ethyl acetate. The obtained organic layer was dried over Na2SO4, distilled under reduced pressure, and then purified with column chromatography to obtain Compound Cpd90 (4.9 g, yield 84%).
HRMS [M]+: 580.189

[Synthesis Example 68] Synthesis of Cpd91

Compound Cpd91 (5.1 g, yield 88%) was obtained by performing the same process as in Synthesis Example 67, except that 2-(4-bromophenyl)-4,6-diphenylpyrimidine (4.6 g, 12.0 mmol) was used instead of 2-(4-bromophenyl)-4,6-diphenyl-1,3,5-triazine used in Synthesis Example 67.
HRMS [M]+: 579.194

[Synthesis Example 69] Synthesis of Cpd92

Compound Cpd92 (5.2 g, yield 90%) was obtained by performing the same process as in Synthesis Example 67, except that 2-(4-bromophenyl)-4,6-diphenylpyridine (4.6 g,

[Synthesis Example 70] Synthesis of Cpd93

Compound Cpd93 (4.9 g, yield 85%) was obtained by performing the same process as in Synthesis Example 67, except that 4-(4-bromophenyl)-2,6-diphenylpyrimidine (4.6 g, 12.0 mmol) was used instead of 2-(4-bromophenyl)-4,6-diphenyl-1,3,5-triazine used in Synthesis Example 67.
HRMS [M]$^+$: 579.194

[Synthesis Example 71] Synthesis of Cpd94

Compound Cpd94 (5.2 g, yield 90%) was obtained by performing the same process as in Synthesis Example 67, except that 2-(3-bromophenyl)-4,6-diphenyl-1,3,5-triazine (4.6 g, 12.0 mmol) was used instead of 2-(4-bromophenyl)-4,6-diphenyl-1,3,5-triazine used in Synthesis Example 67.
HRMS [M]$^+$: 580.189

[Synthesis Example 72] Synthesis of Cpd95

Compound Cpd95 (4.7 g, yield 82%) was obtained by performing the same process as in Synthesis Example 67, except that 2-(3-bromophenyl)-4,6-diphenylpyridine (4.6 g, 12.0 mmol) was used instead of 2-(4-bromophenyl)-4,6-diphenyl-1,3,5-triazine used in Synthesis Example 67.
HRMS [M]$^+$: 578.199

[Synthesis Example 73] Synthesis of Cpd96

Compound Cpd96 (5.1 g, yield 88%) was obtained by performing the same process as in Synthesis Example 67, except that 4-(3-bromophenyl)-2,6-diphenylpyrimidine (4.6 g, 12.0 mmol) was used instead of 2-(4-bromophenyl)-4,6-diphenyl-1,3,5-triazine used in Synthesis Example 67.
HRMS [M]$^+$: 579.194

[Synthesis Example 74] Synthesis of Cpd97

Compound Cpd97 (5.3 g, yield 91%) was obtained by performing the same process as in Synthesis Example 67, except that 2-(3-bromophenyl)-4,6-diphenylpyrimidine (4.6 g, 12.0 mmol) was used instead of 2-(4-bromophenyl)-4,6-diphenyl-1,3,5-triazine used in Synthesis Example 67.
HRMS [M]$^+$: 579.194

[Synthesis Example 75] Synthesis of Cpd100

Compound Cpd100 (6.1 g, yield 83%) was obtained by performing the same process as in Synthesis Example 67, except that 2,4-di([1,1'-biphenyl]-4-yl)-6-(4-bromophenyl)-1,3,5-triazine (6.5 g, 12.0 mmol) was used instead of 2-(4-bromophenyl)-4,6-diphenyl-1,3,5-triazine used in Synthesis Example 67.
HRMS [M]$^+$: 732.252

[Synthesis Example 76] Synthesis of Cpd101

Compound Cpd101 (5.2 g, yield 80%) was obtained by performing the same process as in Synthesis Example 67, except that 2-(5-bromo-[1,1'-biphenyl]-3-yl)-4,6-diphenyl-1,3,5-triazine (5.6 g, 12.0 mmol) was used instead of 2-(4-bromophenyl)-4,6-diphenyl-1,3,5-triazine used in Synthesis Example 67.
HRMS [M]$^+$: 656.221

[Synthesis Example 77] Synthesis of Cpd105

Compound Cpd105 (4.8 g, yield 83%) was obtained by performing the same process as in Synthesis Example 67, except that 2-(3-bromophenyl)triphenylene (4.6 g, 12.0 mmol) was used instead of 2-(4-bromophenyl)-4,6-diphenyl-1,3,5-triazine used in Synthesis Example 67.
HRMS [M]$^+$: 575.188

[Synthesis Example 78] Synthesis of Cpd106

Compound Cpd106 (4.9 g, yield 81%) was obtained by performing the same process as in Synthesis Example 67, except that 4-(4-bromophenyl)-6-phenyldibenzo[b,d]thiophene (5.0 g, 12.0 mmol) was used instead of 2-(4-bromophenyl)-4,6-diphenyl-1,3,5-triazine used in Synthesis Example 67.
HRMS [M]$^+$: 607.160

[Synthesis Example 79] Synthesis of Cpd110

Compound Cpd110 (4.8 g, yield 93%) was obtained by performing the same process as in Synthesis Example 67, except that 3-bromo-9-phenyl-9H-carbazole (3.9 g, 12.0 mmol) was used instead of 2-(4-bromophenyl)-4,6-diphenyl-1,3,5-triazine used in Synthesis Example 67.
HRMS [M]$^+$: 514.618

[Synthesis Example 80] Synthesis of Cpd111

Compound Cpd111 (3.6 g, yield 82%) was obtained by performing the same process as in Synthesis Example 67, except that 4-bromodibenzo[b,d]furan (3.0 g, 12.0 mmol) was used instead of 2-(4-bromophenyl)-4,6-diphenyl-1,3,5-triazine used in Synthesis Example 67.
HRMS [M]$^+$: 439.120

[Synthesis Example 81] Synthesis of Cpd112

Compound Cpd112 (3.6 g, yield 80%) was obtained by performing the same process as in Synthesis Example 67, except that 4-bromodibenzo[b,d]thiophene (3.2 g, 12.0 mmol) was used instead of 2-(4-bromophenyl)-4,6-diphenyl-1,3,5-triazine used in Synthesis Example 67.
HRMS [M]$^+$: 455.098

[Synthesis Example 82] Synthesis of Cpd113

Compound Cpd113 (3.9 g, yield 88%) was obtained by performing the same process as in Synthesis Example 67, except that 2-bromodibenzo[b,d]furan (3.0 g, 12.0 mmol) was used instead of 2-(4-bromophenyl)-4,6-diphenyl-1,3,5-triazine used in Synthesis Example 67.
HRMS [M]$^+$: 439.120

[Synthesis Example 83] Synthesis of Cpd114

Compound Cpd114 (4.1 g, yield 89%) was obtained by performing the same process as in Synthesis Example 67, except that 2-bromodibenzo[b,d]thiophene (3.2 g, 12.0 mmol) was used instead of 2-(4-bromophenyl)-4,6-diphenyl-1,3,5-triazine used in Synthesis Example 67.
HRMS [M]$^+$: 455.098

[Synthesis Example 84] Synthesis of Cpd115

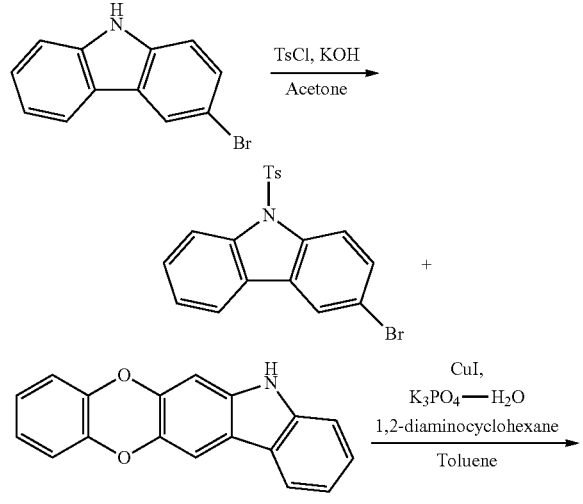

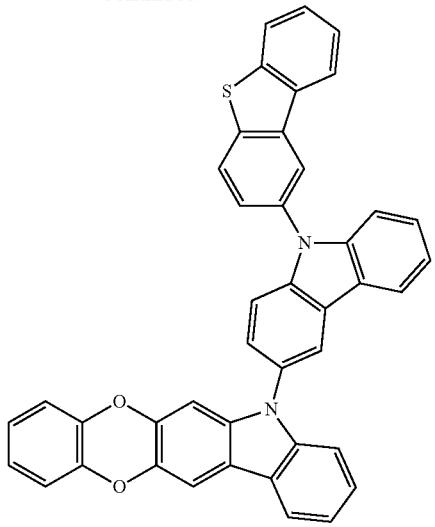 [SMILES: c1ccc2c(c1)Oc1cc3c4ccccc4n(-c4ccc5c(c4)c4ccccc4n5-c4ccc5sc6ccccc6c5c4)c3cc1O2]

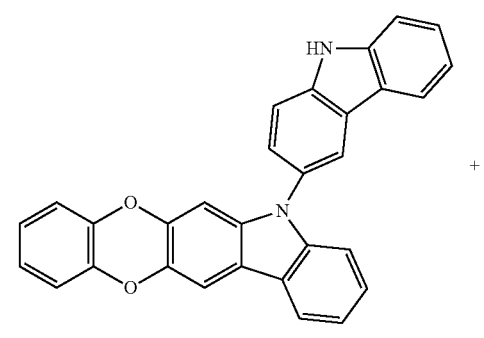

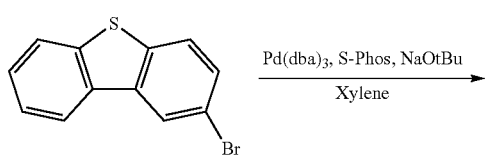

<Step 1> Synthesis of 3-bromo-9-tosyl-9H-carbazole

Acetone (200 mL) was put into KOH (2.7 g, 48 mmol) to dissolve KOH, and then 3-bromo-9H-carbazole (9.8 g, 40 mmol) was introduced thereinto. Thereafter, TsCl (8.4 g, 44 mmol) was added thereto, the mixture was refluxed for 3 hours, and then cooled, and 1 L of iced water was poured therein under stirring. After being stirred for 30 minutes, the mixture was filtered to obtain a crude product. Thereafter, the crude product was recrystallized from CH₂Cl2/EtOH, and then 3-bromo-9-tosyl-9H-carbazole (9.8 g, yield 61%) was obtained.

<Step 2> Synthesis of 5-(9-tosyl-9H-carbazol-3-yl)-5H-benzo[5,6][1,4]dioxino[2,3-b]carbazole The 3-bromo-9-tosyl-9H-carbazole (9.6 g, 24 mmol) obtained in <Step 1>, Compound Inv 1 (7.9 g, 29 mmol) synthesized in Preparation Example 1, CuI (0.4 g, 2.0 mmol), 1,2-diaminocyclohexane (0.3 g, 2.4 mmol), K₃PO₄—H₂O (10.6 g, 50 mmol), and toluene (150 ml) were added to a 500 mL round flask. The reactants were heated under reflux, and stirred under nitrogen atmosphere for 24 hours. After it was confirmed by TLC that the reaction was terminated, the temperature was cooled to normal temperature. After the reaction was terminated, distilled water was added thereto, and an organic layer was extracted with ethyl acetate. The obtained organic layer was dried over Na₂SO₄, distilled under reduced pressure, and then purified with column chromatography to obtain a compound 5-(9-tosyl-9H-carbazol-3-yl)-5H-benzo[5,6][1,4]dioxino[2,3-b]carbazole (12.4 g, yield 87%).

<Step 3> Synthesis of 5-(9H-carbazol-3-yl)-5H-benzo[5,6][1,4]dioxino[2,3-b]carbazole The 5-(9-tosyl-9H-carbazol-3-yl)-5H-benzo[5,6][1,4]dioxino[2,3-b]carbazole (12.4 g, 21 mmol) obtained in <Step 2>, NaOH (8.0 g, 200 mmol), THF (80 ml), MeOH (40 ml), and water (40 ml) were added to a 500 ml-round flask, and then the reactants were heated under reflux for 12 hours. After it was confirmed by TLC that the reaction was terminated, the temperature was cooled to normal temperature. After the reaction was terminated, distilled water was added thereto, and an organic layer was extracted with ethyl acetate. The obtained organic layer was dried over $Na_2SO_4$, distilled under reduced pressure, and then purified with column chromatography to obtain 5-(9H-carbazol-3-yl)-5H-benzo[5,6][1,4]dioxino[2,3-b]carbazole (8.4 g, yield 91%).

<Step 4> Synthesis of Cpd115

The 5-(9H-carbazol-3-yl)-5H-benzo[5,6][1,4]dioxino[2,3-b]carbazole (3.0 g, 7 mmol) obtained in <Step 3>, 2-bromodibenzo thiophene (3.0 g, 10 mmol), $Pd_2(dba)_3$ (0.5 g, 0.5 mmol), S-Phos (0.8 g, 2.0 mmol), NaOtBu (2.9 g, 30 mmol), and 200 ml of xylene were added to a 500 ml-round flask, and the reactants were heated under reflux and stirred under nitrogen atmosphere for 12 hours. After it was confirmed by TLC that the reaction was terminated, the temperature was cooled to normal temperature. After the reaction was terminated, distilled water was added thereto, and an organic layer was extracted with ethyl acetate. The obtained organic layer was dried over $Na_2SO_4$, distilled under reduced pressure, and then purified with column chromatography to obtain Compound Cpd115 (5.2 g, yield 84%).

HRMS [M]+: 620.155

[Synthesis Example 85] Synthesis of Cpd116

Compound Cpd116 (5.9 g, yield 87%) was obtained by performing the same process as in Synthesis Example 84, except that 3-bromo-9-phenyl-9H-carbazole (3.2 g, 10 mmol) was used instead of 2-bromodibenzo thiophene used in Synthesis Example 84.

HRMS [M]+: 679.226

[Synthesis Example 86] Synthesis of Cpd117

Compound Cpd117 (5.4 g, yield 90%) was obtained by performing the same process as in Synthesis Example 84, except that 2-bromodibenzo[b,d]furan (2.5 g, 10 mmol) was used instead of 2-bromodibenzo thiophene used in Synthesis Example 84.

HRMS [M]+: 604.178

[Synthesis Example 87] Synthesis of Cpd118

Compound Cpd118 (5.6 g, yield 83%) was obtained by performing the same process as in Synthesis Example 84, except that 2-chloro-4,6-diphenyl-1,3,5-triazine (2.7 g, 10 mmol) was used instead of 2-bromodibenzo thiophene used in Synthesis Example 84.

HRMS [M]+: 669.216

[Synthesis Example 88] Synthesis of Cpd119

Compound Cpd119 (4.2 g, yield 64%) was obtained by performing the same process as in Synthesis Example 31, except that 2-(3-bromophenyl)-4,6-diphenyl-1,3,5-triazine (4.7 g, 12.0 mmol) was used instead of 4'-bromo-N,N-diphenyl-[1,1'-biphenyl]-4-amine used in Synthesis Example 31.

HRMS [M]+: 656.221

[Synthesis Example 89] Synthesis of Cpd120

Compound Cpd120 (3.9 g, yield 60%) was obtained by performing the same process as in Synthesis Example 31, except that 2-(3-bromophenyl)-4,6-diphenylpyridine (4.6 g, 12.0 mmol) was used instead of 4'-bromo-N,N-diphenyl-[1,1'-biphenyl]-4-amine used in Synthesis Example 31.

HRMS [M]+: 654.230

[Synthesis Example 90] Synthesis of Cpd121

Compound Cpd121 (4.4 g, yield 68%) was obtained by performing the same process as in Synthesis Example 31, except that 4-(3-bromophenyl)-2,6-diphenylpyrimidine (4.7 g, 12.0 mmol) was used instead of 4'-bromo-N,N-diphenyl-[1,1'-biphenyl]-4-amine used in Synthesis Example 31.

HRMS [M]+: 655.226

[Synthesis Example 91] Synthesis of Cpd122

Compound Cpd122 (4.0 g, yield 60%) was obtained by performing the same process as in Synthesis Example 53, except that 2-chloro-4,6-diphenyl-1,3,5-triazine (3.2 g, 12.0 mmol) was used instead of N-(4'-bromo-[1,1'-biphenyl]-4-yl)-N-phenylnaphthalen-2-amine used in Synthesis Example 53.

HRMS [M]+: 656.221

[Synthesis Example 92] Synthesis of Cpd123

Compound Cpd123 (4.0 g, yield 62%) was obtained by performing the same process as in Synthesis Example 53, except that 4-chloro-2,6-diphenylpyrimidine (3.2 g, 12.0 mmol) was used instead of N-(4'-bromo-[1,1'-biphenyl]-4-yl)-N-phenylnaphthalen-2-amine used in Synthesis Example 53.

HRMS [M]+: 655.226

[Synthesis Example 93] Synthesis of Cpd132

Compound Cpd132 (4.9 g, yield 84%) was obtained by performing the same process as in Synthesis Example 67, except that Compound Inv 2 synthesized in Preparation Example 1 was used instead of Compound Inv 1 used in Synthesis Example 67.

HRMS [M]+: 580.189

[Synthesis Example 94] Synthesis of Cpd133

Compound Cpd133 (5.1 g, yield 88%) was obtained by performing the same process as in Synthesis Example 68, except that Compound Inv 2 (2.7 g, 10.0 mmol) synthesized in Preparation Example 1 was used instead of Compound Inv 1 used in Synthesis Example 68.

HRMS [M]+: 579.194

[Synthesis Example 95] Synthesis of Cpd134

Compound Cpd134 (5.2 g, yield 90%) was obtained by performing the same process as in Synthesis Example 69, except that Compound Inv 2 (2.7 g, 10.0 mmol) synthesized in Preparation Example 1 was used instead of Compound Inv 1 used in Synthesis Example 69.

HRMS [M]+: 578.199

[Synthesis Example 96] Synthesis of Cpd135

Compound Cpd135 (4.9 g, yield 85%) was obtained by performing the same process as in Synthesis Example 70, except that Compound Inv 2 (2.7 g, 10.0 mmol) synthesized in Preparation Example 1 was used instead of Compound Inv 1 used in Synthesis Example 70.

HRMS [M]⁺: 579.194

[Synthesis Example 97] Synthesis of Cpd136

Compound Cpd136 (5.2 g, yield 90%) was obtained by performing the same process as in Synthesis Example 71, except that Compound Inv 2 (2.7 g, 10.0 mmol) synthesized in Preparation Example 1 was used instead of Compound Inv 1 used in Synthesis Example 71.

HRMS [M]⁺: 580.189

[Synthesis Example 98] Synthesis of Cpd137

Compound Cpd137 (4.7 g, yield 82%) was obtained by performing the same process as in Synthesis Example 72, except that Compound Inv 2 (2.7 g, 10.0 mmol) synthesized in Preparation Example 1 was used instead of Compound Inv 1 used in Synthesis Example 72.

HRMS [M]⁺: 578.199

[Synthesis Example 99] Synthesis of Cpd138

Compound Cpd138 (5.1 g, yield 88%) was obtained by performing the same process as in Synthesis Example 73, except that Compound Inv 2 (2.7 g, 10.0 mmol) synthesized in Preparation Example 1 was used instead of Compound Inv 1 used in Synthesis Example 73.

HRMS [M]⁺: 579.194

[Synthesis Example 100] Synthesis of Cpd139

Compound Cpd139 (5.3 g, yield 91%) was obtained by performing the same process as in Synthesis Example 74, except that Compound Inv 2 (2.7 g, 10.0 mmol) synthesized in Preparation Example 1 was used instead of Compound Inv 1 used in Synthesis Example 74.

HRMS [M]⁺: 579.194

[Synthesis Example 101] Synthesis of Cpd142

Compound Cpd142 (6.1 g, yield 83%) was obtained by performing the same process as in Synthesis Example 75, except that Compound Inv 2 (2.7 g, 10.0 mmol) synthesized in Preparation Example 1 was used instead of Compound Inv 1 used in Synthesis Example 75.

HRMS [M]⁺: 732.252

[Synthesis Example 102] Synthesis of Cpd143

Compound Cpd143 (5.2 g, yield 80%) was obtained by performing the same process as in Synthesis Example 76, except that Compound Inv 2 (2.7 g, 10.0 mmol) synthesized in Preparation Example 1 was used instead of Compound Inv 1 used in Synthesis Example 76.

HRMS [M]⁺: 656.221

[Synthesis Example 103] Synthesis of Cpd147

Compound Cpd147 (4.8 g, yield 83%) was obtained by performing the same process as in Synthesis Example 77, except that Compound Inv 2 (2.7 g, 10.0 mmol) synthesized in Preparation Example 1 was used instead of Compound Inv 1 used in Synthesis Example 77.

HRMS [M]⁺: 575.188

[Synthesis Example 104] Synthesis of Cpd148

Compound Cpd148 (4.9 g, yield 81%) was obtained by performing the same process as in Synthesis Example 78, except that Compound Inv 2 (2.7 g, 10.0 mmol) synthesized in Preparation Example 1 was used instead of Compound Inv 1 used in Synthesis Example 78.

HRMS [M]⁺: 607.160

[Synthesis Example 105] Synthesis of Cpd152

Compound Cpd152 (4.8 g, yield 93%) was obtained by performing the same process as in Synthesis Example 79, except that Compound Inv 2 (2.7 g, 10.0 mmol) synthesized in Preparation Example 1 was used instead of Compound Inv 1 used in Synthesis Example 79.

HRMS [M]⁺: 514.618

[Synthesis Example 106] Synthesis of Cpd153

Compound Cpd153 (3.6 g, yield 82%) was obtained by performing the same process as in Synthesis Example 80, except that Compound Inv 2 (2.7 g, 10.0 mmol) synthesized in Preparation Example 1 was used instead of Compound Inv 1 used in Synthesis Example 80.

HRMS [M]⁺: 439.120

[Synthesis Example 107] Synthesis of Cpd154

Compound Cpd154 (3.6 g, yield 80%) was obtained by performing the same process as in Synthesis Example 81, except that Compound Inv 2 (2.7 g, 10.0 mmol) synthesized in Preparation Example 1 was used instead of Compound Inv 1 used in Synthesis Example 81.

HRMS [M]⁺: 455.098

[Synthesis Example 108] Synthesis of Cpd155

Compound Cpd155 (3.9 g, yield 88%) was obtained by performing the same process as in Synthesis Example 82, except that Compound Inv 2 (2.7 g, 10.0 mmol) synthesized in Preparation Example 1 was used instead of Compound Inv 1 used in Synthesis Example 82.

HRMS [M]⁺: 439.120

[Synthesis Example 109] Synthesis of Cpd156

Compound Cpd156 (4.1 g, yield 89%) was obtained by performing the same process as in Synthesis Example 83, except that Compound Inv 2 (2.7 g, 10.0 mmol) synthesized in Preparation Example 1 was used instead of Compound Inv 1 used in Synthesis Example 83.

HRMS [M]⁺: 455.098

[Synthesis Example 110] Synthesis of Cpd157

Compound Cpd157 (5.2 g, yield 84%) was obtained by performing the same process as in Synthesis Example 84, except that Compound Inv 2 (2.7 g, 10.0 mmol) synthesized in Preparation Example 1 was used instead of Compound Inv 1 used in Synthesis Example 84.

HRMS [M]⁺: 620.155

[Synthesis Example 111] Synthesis of Cpd158

Compound Cpd158 (5.9 g, yield 87%) was obtained by performing the same process as in Synthesis Example 85, except that Compound Inv 2 (2.7 g, 10.0 mmol) synthesized in Preparation Example 1 was used instead of Compound Inv 1 used in Synthesis Example 85.

HRMS [M]$^+$: 679.226

[Synthesis Example 112] Synthesis of Cpd159

Compound Cpd159 (5.4 g, yield 90%) was obtained by performing the same process as in Synthesis Example 86, except that Compound Inv 2 (2.7 g, 10.0 mmol) synthesized in Preparation Example 1 was used instead of Compound Inv 1 used in Synthesis Example 86.

HRMS [M]$^+$: 604.178

[Synthesis Example 113] Synthesis of Cpd160

Compound Cpd160 (5.6 g, yield 83%) was obtained by performing the same process as in Synthesis Example 87, except that Compound Inv 2 (2.7 g, 10.0 mmol) synthesized in Preparation Example 1 was used instead of Compound Inv 1 used in Synthesis Example 87.

HRMS [M]$^+$: 669.216

[Synthesis Example 114] Synthesis of Cpd161

Compound Cpd119 (4.2 g, yield 64%) was obtained by performing the same process as in Synthesis Example 88, except that Compound Inv 4 (3.1 g, 10.0 mmol) synthesized in Preparation Example 2 was used instead of Compound Inv 3 used in Synthesis Example 88.

HRMS [M]$^+$: 656.221

[Synthesis Example 115] Synthesis of Cpd162

Compound Cpd162 (3.9 g, yield 60%) was obtained by performing the same process as in Synthesis Example 89, except that Compound Inv 4 (3.1 g, 10.0 mmol) synthesized in Preparation Example 2 was used instead of Compound Inv 3 used in Synthesis Example 89.

HRMS [M]$^+$: 654.230

[Synthesis Example 116] Synthesis of Cpd163

Compound Cpd163 (4.4 g, yield 68%) was obtained by performing the same process as in Synthesis Example 90, except that Compound Inv 4 (3.1 g, 10.0 mmol) synthesized in Preparation Example 2 was used instead of Compound Inv 3 used in Synthesis Example 90.

HRMS [M]$^+$: 655.226

[Synthesis Example 117] Synthesis of Cpd164

Compound Cpd164 (4.0 g, yield 60%) was obtained by performing the same process as in Synthesis Example 91, except that Compound Inv 8 (3.1 g, 10.0 mmol) synthesized in Preparation Example 4 was used instead of Compound Inv 7 used in Synthesis Example 91.

HRMS [M]$^+$: 656.221

[Synthesis Example 118] Synthesis of Cpd165

Compound Cpd165 (4.0 g, yield 62%) was obtained by performing the same process as in Synthesis Example 92, except that Compound Inv 8 (3.1 g, 10.0 mmol) synthesized in Preparation Example 4 was used instead of Compound Inv 7 used in Synthesis Example 92.

HRMS [M]$^+$: 655.226

[Example 1] Manufacture of Green Organic Electroluminescent Device

Compound Cpd1 synthesized in Synthesis Example 1 was subjected to highly pure sublimation purification by a typically known method, and then a green organic electroluminescent device was manufactured as follows.

A glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating m-MTDATA (60 nm)/TCTA (80 nm)/Compound Cpd1 (40 nm)/CBP+10% Ir(ppy)$_3$ (300 nm)/BCP (10 nm)/Alq$_3$ (30 nm)/LiF (1 nm)/Al (200 nm) in this order on the thus prepared ITO transparent electrode.

Here, the structures of m-MTDATA, TCTA, Ir(ppy)$_3$, CBP, and BCP used are as follows.

m-MTDATA

TCTA

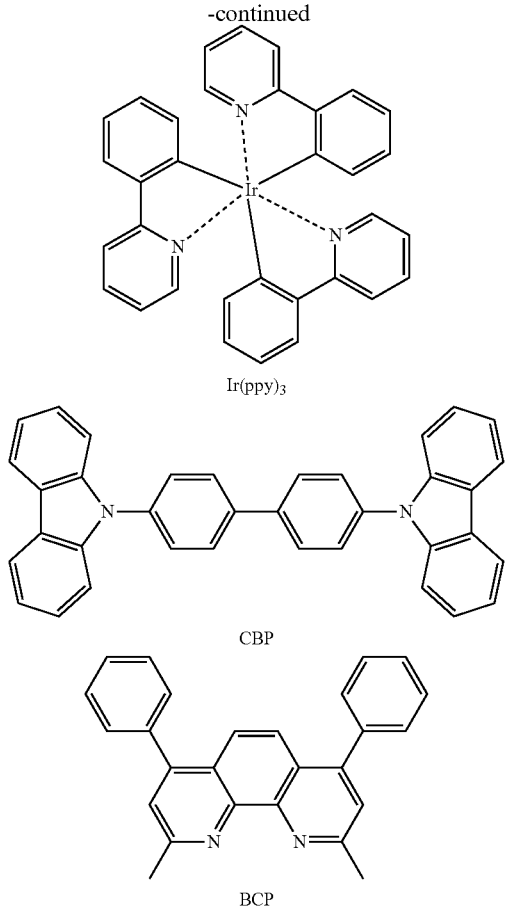

Ir(ppy)₃

CBP

BCP

[Examples 2 to 58] Manufacture of Green Organic Electroluminescent Device

An organic electroluminescent device was manufactured in the same manner as in Example 1, except that the compounds described in the following Table 1 were each used instead of Compound Cpd1 used in Example 1.

[Comparative Example 1] Manufacture of Green Organic Electroluminescent Device

A green organic electroluminescent device was manufactured in the same manner as in Example 1, except that Compound Cpd1 used in Example 1 was not used.

Evaluation Example 1

For each of the green organic electroluminescent devices manufactured in Examples 1 to 58 and Comparative Example 1, the driving voltage, current efficiency, and light emitting peak thereof were measured at a current density of 10 mA/cm², and the results are shown in the following Table 1.

TABLE 1

|  | Material of light emitting auxiliary layer | Driving voltage (V) | Light emitting peak (nm) | Current efficiency (cd/A) |
|---|---|---|---|---|
| Example 1 | Cpd1 | 6.80 | 517 | 42.0 |
| Example 2 | Cpd2 | 6.85 | 518 | 41.9 |

TABLE 1-continued

|  | Material of light emitting auxiliary layer | Driving voltage (V) | Light emitting peak (nm) | Current efficiency (cd/A) |
|---|---|---|---|---|
| Example 3 | Cpd3 | 6.71 | 520 | 41.5 |
| Example 4 | Cpd4 | 6.85 | 518 | 41.8 |
| Example 5 | Cpd5 | 6.85 | 520 | 41.8 |
| Example 6 | Cpd6 | 6.80 | 519 | 41.5 |
| Example 7 | Cpd7 | 6.90 | 518 | 41.8 |
| Example 8 | Cpd8 | 6.85 | 520 | 41.5 |
| Example 9 | Cpd12 | 6.73 | 518 | 41.5 |
| Example 10 | Cpd13 | 6.74 | 520 | 41.8 |
| Example 11 | Cpd14 | 6.75 | 518 | 41.8 |
| Example 12 | Cpd15 | 6.80 | 517 | 41.5 |
| Example 13 | Cpd16 | 6.77 | 518 | 42.0 |
| Example 14 | Cpd17 | 6.72 | 520 | 41.9 |
| Example 15 | Cpd18 | 6.80 | 518 | 41.5 |
| Example 16 | Cpd19 | 6.69 | 520 | 41.8 |
| Example 17 | Cpd20 | 6.82 | 517 | 41.8 |
| Example 18 | Cpd21 | 6.75 | 518 | 41.8 |
| Example 19 | Cpd22 | 6.80 | 520 | 42.0 |
| Example 20 | Cpd23 | 6.77 | 518 | 42.0 |
| Example 21 | Cpd24 | 6.85 | 520 | 41.5 |
| Example 22 | Cpd25 | 6.80 | 519 | 41.8 |
| Example 23 | Cpd26 | 6.90 | 517 | 41.8 |
| Example 24 | Cpd27 | 6.70 | 518 | 41.5 |
| Example 25 | Cpd28 | 6.73 | 520 | 41.8 |
| Example 26 | Cpd29 | 6.74 | 518 | 42.0 |
| Example 27 | Cpd33 | 6.69 | 520 | 41.8 |
| Example 28 | Cpd34 | 6.80 | 520 | 41.5 |
| Example 29 | Cpd35 | 6.71 | 519 | 41.8 |
| Example 30 | Cpd36 | 6.85 | 517 | 41.5 |
| Example 31 | Cpd37 | 6.69 | 520 | 41.8 |
| Example 32 | Cpd38 | 6.82 | 517 | 41.8 |
| Example 33 | Cpd39 | 6.75 | 518 | 41.8 |
| Example 34 | Cpd40 | 6.80 | 520 | 42.0 |
| Example 35 | Cpd41 | 6.80 | 520 | 41.8 |
| Example 36 | Cpd42 | 6.90 | 518 | 41.8 |
| Example 37 | Cpd46 | 6.75 | 518 | 41.9 |
| Example 38 | Cpd47 | 6.80 | 520 | 42.0 |
| Example 39 | Cpd48 | 6.71 | 518 | 41.9 |
| Example 40 | Cpd49 | 6.85 | 520 | 41.5 |
| Example 41 | Cpd51 | 6.80 | 518 | 41.8 |
| Example 42 | Cpd52 | 6.90 | 520 | 41.5 |
| Example 43 | Cpd54 | 6.80 | 520 | 42.0 |
| Example 44 | Cpd55 | 6.90 | 519 | 41.9 |
| Example 45 | Cpd56 | 6.70 | 517 | 41.5 |
| Example 46 | Cpd57 | 6.73 | 518 | 41.8 |
| Example 47 | Cpd60 | 6.80 | 520 | 41.5 |
| Example 48 | Cpd70 | 6.71 | 519 | 41.5 |
| Example 49 | Cpd71 | 6.85 | 517 | 41.8 |
| Example 50 | Cpd72 | 6.70 | 518 | 42.0 |
| Example 51 | Cpd73 | 6.70 | 517 | 42.0 |
| Example 52 | Cpd75 | 6.73 | 518 | 41.9 |
| Example 53 | Cpd76 | 6.70 | 517 | 41.5 |
| Example 54 | Cpd77 | 6.73 | 518 | 41.8 |
| Example 55 | Cpd78 | 6.74 | 520 | 41.5 |
| Example 56 | Cpd79 | 6.75 | 518 | 41.8 |
| Example 57 | Cpd80 | 6.85 | 517 | 41.5 |
| Example 58 | Cpd81 | 6.80 | 520 | 42.0 |
| Comparative Example 1 | — | 6.93 | 516 | 38.2 |

As shown in Table 1, it could be seen that the green organic electroluminescent devices in Examples 1 to 58 in which the compounds (Cpd1 to Cpd81) represented by Formula 1 according to the present disclosure were used as a material of light emitting auxiliary layer had slightly lower driving voltages than that of the green organic electroluminescent device in Comparative Example 1 in which only CBP was used as a material of light emitting layer without a light emitting auxiliary layer, and had better current efficiencies than that of the green organic electroluminescent device in Comparative Example 1.

[Example 59] Manufacture of Red Organic Electroluminescent Device

Compound Cpd1 synthesized in Synthesis Example 1 was subjected to highly pure sublimation purification by a typically known method, and then a red organic electroluminescent device was manufactured as follows.

First, a glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating m-MTDATA (60 nm)/TCTA (80 nm)/Compound Cpd1 (40 nm)/CBP+10% (piq)$_2$Ir(acac) (300 nm)/BCP (10 nm)/Alq$_3$ (30 nm)/LiF (1 nm)/Al (200 nm) in this order on the thus prepared ITO transparent electrode.

Here, the structures of m-MTDATA, TCTA, CBP, and BCP used are the same as described in Example 1, and (piq)$_2$Ir(acac) is as follows.

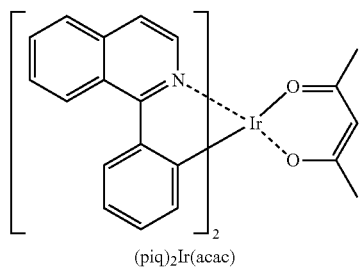

(piq)$_2$Ir(acac)

[Examples 60 to 116] Manufacture of Red Organic Electroluminescent Device

A red organic electroluminescent device was manufactured in the same manner as in Example 59, except that the compounds described in the following Table 2 were each used instead of Compound Cpd1 used in Example 59.

[Comparative Example 2] Manufacture of Red Organic Electroluminescent Device

A red organic electroluminescent device was manufactured in the same manner as in Example 59, except that Compound Cpd1 used in Example 59 was not used.

Evaluation Example 2

For each of the red organic electroluminescent devices manufactured in Examples 59 to 116 and Comparative Example 2, the driving voltage and current efficiency thereof were measured at a current density of 10 mA/cm$^2$, and the results are shown in the following Table 2.

TABLE 2

| | Material of light emitting auxiliary layer | Driving voltage (V) | Current efficiency (cd/A) |
|---|---|---|---|
| Example 59 | Cpd1 | 5.15 | 10.8 |
| Example 60 | Cpd2 | 5.10 | 11.2 |
| Example 61 | Cpd3 | 5.15 | 11.0 |
| Example 62 | Cpd4 | 5.20 | 10.8 |
| Example 63 | Cpd5 | 5.15 | 11.2 |
| Example 64 | Cpd6 | 5.10 | 11.0 |
| Example 65 | Cpd7 | 5.15 | 11.3 |
| Example 66 | Cpd8 | 5.10 | 11.0 |
| Example 67 | Cpd12 | 5.15 | 11.3 |
| Example 68 | Cpd13 | 5.20 | 10.8 |
| Example 69 | Cpd14 | 5.13 | 11.1 |
| Example 70 | Cpd15 | 5.16 | 11.5 |
| Example 71 | Cpd16 | 5.17 | 11.6 |
| Example 72 | Cpd17 | 5.14 | 11.0 |
| Example 73 | Cpd18 | 5.15 | 10.8 |
| Example 74 | Cpd19 | 5.10 | 11.2 |
| Example 75 | Cpd20 | 5.15 | 11.0 |
| Example 76 | Cpd21 | 5.20 | 11.3 |
| Example 77 | Cpd22 | 5.15 | 11.0 |
| Example 78 | Cpd23 | 5.10 | 11.3 |
| Example 79 | Cpd24 | 5.15 | 10.8 |
| Example 80 | Cpd25 | 5.10 | 11.1 |
| Example 81 | Cpd26 | 5.15 | 11.5 |
| Example 82 | Cpd27 | 5.20 | 10.8 |
| Example 83 | Cpd28 | 5.13 | 11.2 |
| Example 84 | Cpd29 | 5.20 | 11.0 |
| Example 85 | Cpd33 | 5.15 | 10.8 |
| Example 86 | Cpd34 | 5.10 | 11.2 |
| Example 87 | Cpd35 | 5.15 | 11.0 |
| Example 88 | Cpd36 | 5.10 | 11.3 |
| Example 89 | Cpd37 | 5.15 | 11.0 |
| Example 90 | Cpd38 | 5.20 | 11.3 |
| Example 91 | Cpd39 | 5.13 | 10.8 |
| Example 92 | Cpd40 | 5.16 | 11.1 |
| Example 93 | Cpd41 | 5.17 | 11.5 |
| Example 94 | Cpd42 | 5.14 | 11.6 |
| Example 95 | Cpd46 | 5.15 | 11.0 |
| Example 96 | Cpd47 | 5.10 | 10.8 |
| Example 97 | Cpd48 | 5.15 | 11.2 |
| Example 98 | Cpd49 | 5.20 | 11.1 |
| Example 99 | Cpd51 | 5.15 | 11.5 |
| Example 100 | Cpd52 | 5.10 | 11.6 |
| Example 101 | Cpd54 | 5.15 | 11.0 |
| Example 102 | Cpd55 | 5.10 | 10.8 |
| Example 103 | Cpd56 | 5.15 | 11.2 |
| Example 104 | Cpd57 | 5.20 | 11.0 |
| Example 105 | Cpd60 | 5.13 | 11.3 |
| Example 106 | Cpd70 | 5.20 | 11.0 |
| Example 107 | Cpd71 | 5.15 | 11.3 |
| Example 108 | Cpd72 | 5.10 | 10.8 |
| Example 109 | Cpd73 | 5.15 | 11.1 |
| Example 110 | Cpd75 | 5.10 | 11.5 |
| Example 111 | Cpd76 | 5.15 | 10.8 |
| Example 112 | Cpd77 | 5.15 | 11.2 |
| Example 113 | Cpd78 | 5.10 | 11.0 |
| Example 114 | Cpd79 | 5.15 | 10.8 |
| Example 115 | Cpd80 | 5.15 | 11.0 |
| Example 116 | Cpd81 | 5.10 | 10.8 |
| Comparative Example 2 | — | 5.25 | 8.2 |

As shown in Table 2, it could be seen that the red organic electroluminescent devices in Examples 59 to 116 in which the compounds (Cpd1 to Cpd81) represented by Formula 1 according to the present disclosure were used as a material of light emitting auxiliary layer had slightly lower driving voltages than that of the red organic electroluminescent device in Comparative Example 2 in which only CBP was used as a material of light emitting layer without a light emitting auxiliary layer, and had better current efficiencies than that of the red organic electroluminescent device in Comparative Example 2.

[Example 117] Manufacture of Blue Organic Electroluminescent Device

Compound Cpd1 synthesized in Synthesis Example 1 was subjected to highly pure sublimation purification by a typically known method, and then a blue organic electroluminescent device was manufactured as follows.

First, a glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating DS-205 (Manufactured by Doosan Corporation Electronics) (80 nm)/NPB (15 nm)/Compound Cpd1 (15 nm)/ADN+5% DS-405 (Manufactured by Doosan Corporation Electronics) (300 nm)/BCP (10 nm)/Alq$_3$ (30 nm)/LiF (1 nm)/Al (200 nm) in this order on the thus prepared ITO transparent electrode.

The BCP used is the same as that described in Example 1, and the structures of NPB and ADN are the same as those described as follows.

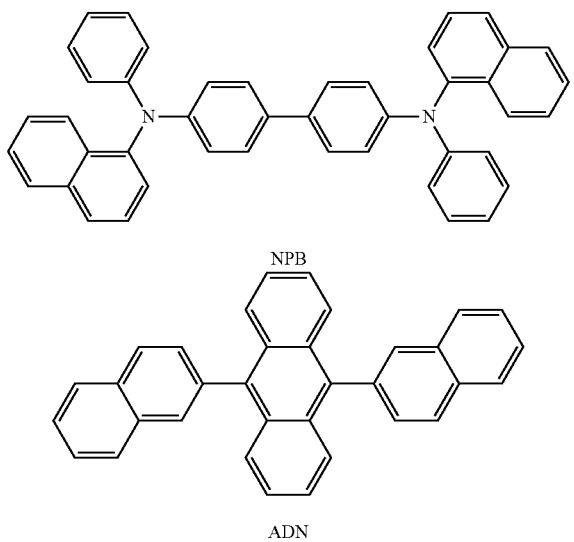

NPB

ADN

[Examples 118 to 174] Manufacture of Blue Organic Electroluminescent Device

A blue organic electroluminescent device was manufactured in the same manner as in Example 117, except that the compounds described in the following Table 3 were each used instead of Compound Cpd1 used in Example 117.

[Comparative Example 3] Manufacture of Blue Organic Electroluminescent Device A blue organic electroluminescent device was manufactured in the same manner as in Example 117, except that Compound Cpd1 used in Example 117 was not used.

Evaluation Example 3

For each of the blue organic electroluminescent devices manufactured in Examples 117 to 174 and Comparative Example 3, the driving voltage and current efficiency thereof were measured at a current density of 10 mA/cm$^2$, and the results are shown in the following Table 3.

TABLE 3

| | Material of light emitting auxiliary layer | Driving voltage (V) | Current efficiency (cd/A) |
| --- | --- | --- | --- |
| Example 117 | Cpd1 | 5.50 | 6.9 |
| Example 118 | Cpd2 | 5.60 | 6.6 |
| Example 119 | Cpd3 | 5.55 | 6.8 |
| Example 120 | Cpd4 | 5.60 | 6.9 |
| Example 121 | Cpd5 | 5.51 | 6.6 |
| Example 122 | Cpd6 | 5.55 | 6.8 |
| Example 123 | Cpd7 | 5.51 | 6.0 |
| Example 124 | Cpd8 | 5.55 | 6.4 |
| Example 125 | Cpd12 | 5.60 | 6.0 |
| Example 126 | Cpd13 | 5.65 | 6.4 |
| Example 127 | Cpd14 | 5.53 | 6.5 |
| Example 128 | Cpd15 | 5.56 | 6.8 |
| Example 129 | Cpd16 | 5.49 | 6.1 |
| Example 130 | Cpd17 | 5.50 | 6.9 |
| Example 131 | Cpd18 | 5.60 | 6.6 |
| Example 132 | Cpd19 | 5.55 | 6.8 |
| Example 133 | Cpd20 | 5.60 | 6.9 |
| Example 134 | Cpd21 | 5.51 | 6.6 |
| Example 135 | Cpd22 | 5.55 | 6.8 |
| Example 136 | Cpd23 | 5.51 | 6.0 |
| Example 137 | Cpd24 | 5.55 | 6.4 |
| Example 138 | Cpd25 | 5.60 | 6.5 |
| Example 139 | Cpd26 | 5.65 | 6.8 |
| Example 140 | Cpd27 | 5.53 | 6.1 |
| Example 141 | Cpd28 | 5.56 | 6.9 |
| Example 142 | Cpd29 | 5.49 | 6.6 |
| Example 143 | Cpd33 | 5.50 | 6.8 |
| Example 144 | Cpd34 | 5.60 | 6.9 |
| Example 145 | Cpd35 | 5.55 | 6.4 |
| Example 146 | Cpd36 | 5.60 | 6.5 |
| Example 147 | Cpd37 | 5.51 | 6.8 |
| Example 148 | Cpd38 | 5.55 | 6.1 |
| Example 149 | Cpd39 | 5.51 | 6.9 |
| Example 150 | Cpd40 | 5.55 | 6.6 |
| Example 151 | Cpd41 | 5.60 | 6.8 |
| Example 152 | Cpd42 | 5.65 | 6.9 |
| Example 153 | Cpd46 | 5.53 | 6.6 |
| Example 154 | Cpd47 | 5.56 | 6.4 |
| Example 155 | Cpd48 | 5.49 | 6.5 |
| Example 156 | Cpd49 | 5.60 | 6.8 |
| Example 157 | Cpd51 | 5.55 | 6.1 |
| Example 158 | Cpd52 | 5.60 | 6.9 |
| Example 159 | Cpd54 | 5.51 | 6.6 |
| Example 160 | Cpd55 | 5.55 | 6.8 |
| Example 161 | Cpd56 | 5.51 | 6.9 |
| Example 162 | Cpd57 | 5.55 | 6.6 |
| Example 163 | Cpd60 | 5.60 | 6.8 |
| Example 164 | Cpd70 | 5.65 | 6.0 |
| Example 165 | Cpd71 | 5.53 | 6.4 |
| Example 166 | Cpd72 | 5.60 | 6.5 |
| Example 167 | Cpd73 | 5.55 | 6.8 |
| Example 168 | Cpd75 | 5.60 | 6.1 |
| Example 169 | Cpd76 | 5.51 | 6.9 |
| Example 170 | Cpd77 | 5.55 | 6.6 |
| Example 171 | Cpd78 | 5.51 | 6.8 |
| Example 172 | Cpd79 | 5.55 | 6.1 |
| Example 173 | Cpd80 | 5.54 | 6.3 |
| Example 174 | Cpd81 | 5.58 | 6.1 |
| Comparative Example 3 | — | 5.60 | 4.8 |

As shown in Table 3, it could be seen that the blue organic electroluminescent devices in Examples 117 to 174 in which the compounds (Cpd1 to Cpd81) represented by Formula 1 according to the present disclosure were used as a material of light emitting auxiliary layer had driving voltages similar to that of the blue organic electroluminescent device in Comparative Example 3 in which ADN was used as a material of light emitting layer without a light emitting auxiliary layer, but had better current efficiencies than that of the organic electroluminescent device in Comparative Example 3.

[Example 175] Manufacture of Green Organic Electroluminescent Device

Compound Cpd86 synthesized in Synthesis Example 59 was subjected to highly pure sublimation purification by a typically known method, and then a green organic electroluminescent device was manufactured according to the following procedure.

First, a glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating m-MTDATA (60 nm)/TCTA (80 nm)/Compound Cpd86+10% Ir(ppy)$_3$ (300 nm)/BCP (10 nm)/Alq$_3$ (30 nm)/LiF (1 nm)/Al (200 nm) in this order on the thus prepared ITO transparent electrode.

[Examples 176 TO 234] Manufacture of Green Organic Electroluminescent Device

A green organic electroluminescent device was manufactured in the same manner as in Example 175, except that the compounds described in the following Table 4 were each used instead of Compound Cpd86 used in Example 217.

[Comparative Example 4] Manufacture of Green Organic Electroluminescent Device

A green organic electroluminescent device was manufactured by the same procedure as in Example 175, except that CBP was used instead of Compound Cpd86 used as a material of light emitting host when a light emitting layer was formed in Example 175.

Evaluation Example 4

For each of the green organic electroluminescent devices manufactured in Examples 175 to 234 and Comparative Example 4, the driving voltage, current efficiency, and light emitting peak thereof were measured at a current density of 10 mA/cm$^2$, and the results are shown in the following Table 4.

TABLE 4

| Sample | Host | Driving voltage (V) | EL peak (nm) | Current efficiency (cd/A) |
|---|---|---|---|---|
| Example 175 | Cpd86 | 6.63 | 518 | 40.5 |
| Example 176 | Cpd87 | 6.78 | 515 | 42.4 |
| Example 177 | Cpd88 | 6.81 | 518 | 41.1 |
| Example 178 | Cpd89 | 6.79 | 517 | 40.8 |
| Example 179 | Cpd90 | 6.81 | 518 | 41.1 |
| Example 180 | Cpd91 | 6.79 | 517 | 40.8 |
| Example 181 | Cpd92 | 6.78 | 515 | 42.4 |
| Example 182 | Cpd93 | 6.81 | 518 | 41.1 |
| Example 183 | Cpd94 | 6.79 | 517 | 40.8 |
| Example 184 | Cpd95 | 6.81 | 518 | 41.1 |
| Example 185 | Cpd96 | 6.79 | 517 | 40.8 |
| Example 186 | Cpd97 | 6.79 | 517 | 40.8 |
| Example 187 | Cpd100 | 6.81 | 518 | 41.1 |
| Example 188 | Cpd101 | 6.79 | 517 | 40.8 |
| Example 189 | Cpd105 | 6.81 | 518 | 41.1 |
| Example 190 | Cpd106 | 6.78 | 515 | 42.4 |
| Example 191 | Cpd110 | 6.79 | 517 | 40.8 |
| Example 192 | Cpd111 | 6.79 | 517 | 40.8 |
| Example 193 | Cpd112 | 6.81 | 518 | 41.1 |
| Example 194 | Cpd113 | 6.79 | 517 | 40.8 |
| Example 195 | Cpd114 | 6.78 | 515 | 42.4 |
| Example 196 | Cpd115 | 6.81 | 518 | 41.1 |
| Example 197 | Cpd116 | 6.79 | 517 | 40.8 |
| Example 198 | Cpd117 | 6.81 | 518 | 41.1 |
| Example 199 | Cpd118 | 6.79 | 517 | 40.8 |
| Example 200 | Cpd119 | 6.78 | 515 | 42.4 |
| Example 201 | Cpd120 | 6.81 | 518 | 41.1 |
| Example 202 | Cpd121 | 6.79 | 517 | 40.8 |
| Example 203 | Cpd122 | 6.81 | 518 | 41.1 |
| Example 204 | Cpd123 | 6.79 | 517 | 40.8 |
| Example 205 | Cpd128 | 6.79 | 517 | 40.8 |
| Example 206 | Cpd129 | 6.81 | 518 | 41.1 |
| Example 207 | Cpd130 | 6.79 | 517 | 40.8 |
| Example 208 | Cpd131 | 6.79 | 517 | 40.8 |
| Example 209 | Cpd132 | 6.81 | 518 | 41.1 |
| Example 210 | Cpd133 | 6.78 | 515 | 42.4 |
| Example 211 | Cpd134 | 6.81 | 518 | 41.1 |
| Example 212 | Cpd135 | 6.79 | 517 | 40.8 |
| Example 213 | Cpd136 | 6.81 | 518 | 41.1 |
| Example 214 | Cpd137 | 6.79 | 517 | 40.8 |
| Example 215 | Cpd138 | 6.79 | 517 | 40.8 |
| Example 216 | Cpd139 | 6.81 | 518 | 41.1 |
| Example 217 | Cpd142 | 6.78 | 515 | 42.4 |
| Example 218 | Cpd143 | 6.81 | 518 | 41.1 |
| Example 219 | Cpd147 | 6.79 | 517 | 40.8 |
| Example 220 | Cpd148 | 6.81 | 518 | 41.1 |
| Example 221 | Cpd152 | 6.81 | 518 | 41.1 |
| Example 222 | Cpd153 | 6.79 | 517 | 40.8 |
| Example 223 | Cpd154 | 6.79 | 517 | 40.8 |
| Example 224 | Cpd155 | 6.81 | 518 | 41.1 |
| Example 225 | Cpd156 | 6.79 | 517 | 40.8 |
| Example 226 | Cpd157 | 6.81 | 518 | 41.1 |
| Example 227 | Cpd158 | 6.78 | 515 | 42.4 |
| Example 228 | Cpd159 | 6.81 | 518 | 41.1 |
| Example 229 | Cpd160 | 6.79 | 517 | 40.8 |
| Example 230 | Cpd161 | 6.81 | 518 | 41.1 |
| Example 231 | Cpd162 | 6.79 | 517 | 40.8 |
| Example 232 | Cpd163 | 6.79 | 517 | 40.8 |
| Example 233 | Cpd164 | 6.81 | 518 | 41.1 |
| Example 234 | Cpd165 | 6.79 | 517 | 40.8 |
| Comparative Example 4 | CBP | 6.93 | 516 | 38.2 |

As shown in Table 4, it could be seen that the green organic electroluminescent devices in Examples 175 to 234 in which Compounds Cpd86 to 165 synthesized in Synthesis Examples 59 to 118 were each used as a material of light emitting layer exhibited better performances in terms of current efficiency and driving voltage than the green organic electroluminescent device in Comparative Example 4 in which CBP in the related art was used.

[Example 235] Manufacture of Blue Organic Electroluminescent Device

Compound Cpd105 synthesized in Synthesis Example 77 was subjected to highly pure sublimation purification by a typically known method, and then a blue organic electroluminescent device was manufactured according to the following procedure.

First, a glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating CuPc (10 nm)/TPAC (30 nm)/Compound Cpd105+7% Flrpic (300 nm)/Alq$_3$ (30 nm)/LiF (0.2 nm)/Al (150 nm) in this order on the thus prepared ITO transparent electrode.

Here, the structures of CuPc, TPAC, and Flrpic used are as follows.

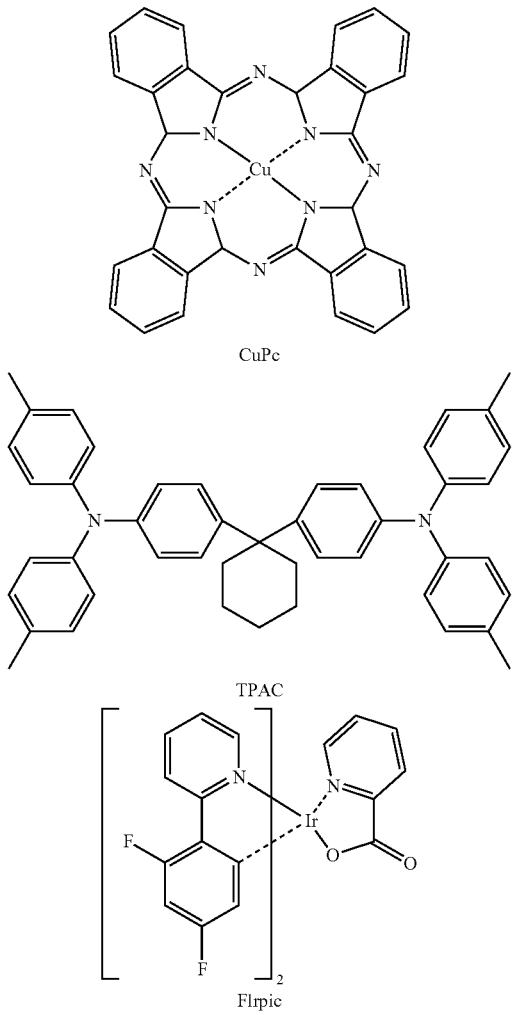

[Examples 236 to 257] Manufacture of Blue Organic Electroluminescent Device

A blue organic electroluminescent device was manufactured in the same manner as in Example 235, except that the compounds described in the following Table 5 were each used instead of Compound Cpd105 used in Example 235.

[Comparative Example 5] Manufacture of Blue Organic Electroluminescent Device

A blue organic electroluminescent device was manufactured by the same procedure as in Example 235, except that CBP was used instead of Compound Cpd105 used as a material of light emitting host when a light emitting layer was formed in Example 235.

Evaluation Example 5

For each of the blue organic electroluminescent devices manufactured in Examples 235 to 257 and Comparative Example 5, the driving voltage, current efficiency, and light emitting peak thereof were measured at a current density of 10 mA/cm$^2$, and the results are shown in the following Table 5.

TABLE 5

| Sample | Host | Driving voltage (V) | EL peak (nm) | Current efficiency (cd/A) |
|---|---|---|---|---|
| Example 235 | Cpd105 | 7.30 | 474 | 6.34 |
| Example 236 | Cpd106 | 7.24 | 475 | 6.55 |
| Example 237 | Cpd110 | 7.24 | 475 | 6.55 |
| Example 238 | Cpd111 | 7.15 | 471 | 6.94 |
| Example 239 | Cpd112 | 7.23 | 472 | 6.25 |
| Example 240 | Cpd113 | 7.12 | 472 | 5.85 |
| Example 241 | Cpd114 | 7.00 | 472 | 6.34 |
| Example 242 | Cpd115 | 7.29 | 473 | 6.90 |
| Example 243 | Cpd116 | 7.30 | 474 | 6.34 |
| Example 244 | Cpd117 | 7.24 | 475 | 6.55 |
| Example 245 | Cpd147 | 7.15 | 471 | 6.94 |
| Example 246 | Cpd148 | 7.23 | 472 | 6.25 |
| Example 247 | Cpd152 | 7.30 | 474 | 6.34 |
| Example 248 | Cpd153 | 7.24 | 475 | 6.55 |
| Example 249 | Cpd154 | 7.15 | 471 | 6.94 |
| Example 250 | Cpd155 | 7.23 | 472 | 6.25 |
| Example 251 | Cpd156 | 7.12 | 472 | 5.85 |
| Example 252 | Cpd157 | 7.00 | 472 | 6.34 |
| Example 253 | Cpd158 | 7.29 | 473 | 6.90 |
| Example 254 | Cpd159 | 7.30 | 474 | 6.34 |
| Example 255 | Cpd168 | 7.24 | 475 | 6.55 |
| Example 256 | Cpd171 | 7.24 | 475 | 6.55 |
| Example 257 | Cpd174 | 7.15 | 471 | 6.94 |
| Comparative Example 5 | CBP | 7.80 | 474 | 5.80 |

As shown in Table 5, it could be seen that the blue organic electroluminescent devices in Examples 235 to 257 in which the compounds (Compounds Cpd105 to Cpd174) according to the present disclosure were each used as a material of light emitting layer exhibited better performances in terms of current efficiency and driving voltage than the blue organic electroluminescent device in Comparative Example 5 in which CBP in the related art was used.

[Example 258] Manufacture of Green Organic Electroluminescent Device

A glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating m-MTDATA (60 nm)/Compound Cpd1 (80 nm)/DS-H522+5% DS-501 (Manufactured by Doosan Corporation Electronics) (300 nm)/BCP (10 nm)/Alq$_3$ (30 nm)/LiF (1 nm)/Al (200 nm) in this order, as a material of hole transport layer, on the ITO transparent electrode prepared as described above.

[Examples 259 to 315] Manufacture of Green Organic Electroluminescent Device

A green organic electroluminescent device was manufactured in the same manner as in Example 258, except that the compounds described in the following Table 6 were each used instead of Compound Cpd1 used in Example 258.

[Comparative Example 6] Manufacture of Organic Electroluminescent Device

An organic electroluminescent device was manufactured in the same manner as in Example 258, except that NPB was used as a material of hole transport layer instead of Compound Cpd1 used when a hole transport layer was formed in Example 258.

Evaluation Example 6

For each of the green organic electroluminescent devices manufactured in Examples 258 to 315 and Comparative Example 6, the driving voltage and current efficiency thereof were measured at a current density of 10 mA/cm$^2$, and the results are shown in the following Table 6.

TABLE 6

| Sample | Hole transport layer | Driving voltage (V) | Current efficiency (cd/A) |
| --- | --- | --- | --- |
| Example 258 | Cpd1 | 4.1 | 22.2 |
| Example 259 | Cpd2 | 4.3 | 20.1 |
| Example 260 | Cpd3 | 4.4 | 21.3 |
| Example 261 | Cpd4 | 4.0 | 22.6 |
| Example 262 | Cpd5 | 4.5 | 19.5 |
| Example 263 | Cpd6 | 4.7 | 20.1 |
| Example 264 | Cpd7 | 4.3 | 21.6 |
| Example 265 | Cpd8 | 4.5 | 20.5 |
| Example 266 | Cpd12 | 4.7 | 20.6 |
| Example 267 | Cpd13 | 4.4 | 21.6 |
| Example 268 | Cpd14 | 5.0 | 20.1 |
| Example 269 | Cpd15 | 5.1 | 18.6 |
| Example 270 | Cpd16 | 4.3 | 22.0 |
| Example 271 | Cpd17 | 4.6 | 21.2 |
| Example 272 | Cpd18 | 4.5 | 21.2 |
| Example 273 | Cpd19 | 4.4 | 22.3 |
| Example 274 | Cpd20 | 5.1 | 18.2 |
| Example 275 | Cpd21 | 5.0 | 18.9 |
| Example 276 | Cpd22 | 4.5 | 21.7 |
| Example 277 | Cpd23 | 4.7 | 21.2 |
| Example 278 | Cpd24 | 4.8 | 20.8 |
| Example 279 | Cpd25 | 4.5 | 21.4 |
| Example 280 | Cpd26 | 5.1 | 18.2 |
| Example 281 | Cpd27 | 5.1 | 18.5 |
| Example 282 | Cpd28 | 4.3 | 22.3 |
| Example 283 | Cpd29 | 4.6 | 21.4 |
| Example 284 | Cpd33 | 4.8 | 21.6 |
| Example 285 | Cpd34 | 4.2 | 22.5 |
| Example 286 | Cpd35 | 4.7 | 20.6 |
| Example 287 | Cpd36 | 4.6 | 20.2 |
| Example 288 | Cpd37 | 4.2 | 22.1 |
| Example 289 | Cpd38 | 4.6 | 21.2 |
| Example 290 | Cpd39 | 4.8 | 20.0 |
| Example 291 | Cpd40 | 4.2 | 22.3 |
| Example 292 | Cpd41 | 4.8 | 21.8 |
| Example 293 | Cpd42 | 5.0 | 19.2 |
| Example 294 | Cpd46 | 4.5 | 20.3 |
| Example 295 | Cpd47 | 5.3 | 17.2 |

TABLE 6-continued

| Sample | Hole transport layer | Driving voltage (V) | Current efficiency (cd/A) |
| --- | --- | --- | --- |
| Example 296 | Cpd48 | 4.9 | 20.3 |
| Example 297 | Cpd49 | 4.0 | 22.6 |
| Example 298 | Cpd51 | 4.5 | 19.5 |
| Example 299 | Cpd52 | 4.7 | 20.1 |
| Example 300 | Cpd54 | 4.3 | 21.6 |
| Example 301 | Cpd55 | 4.5 | 20.5 |
| Example 302 | Cpd56 | 4.7 | 20.6 |
| Example 303 | Cpd57 | 4.4 | 21.6 |
| Example 304 | Cpd60 | 4.0 | 22.6 |
| Example 305 | Cpd70 | 4.5 | 19.5 |
| Example 306 | Cpd71 | 4.7 | 20.1 |
| Example 307 | Cpd72 | 4.3 | 21.6 |
| Example 308 | Cpd73 | 4.5 | 20.5 |
| Example 309 | Cpd75 | 4.7 | 20.6 |
| Example 310 | Cpd76 | 4.4 | 21.6 |
| Example 311 | Cpd77 | 5.0 | 20.1 |
| Example 312 | Cpd78 | 4.5 | 20.3 |
| Example 313 | Cpd79 | 5.0 | 20.2 |
| Example 314 | Cpd80 | 4.9 | 20.3 |
| Example 315 | Cpd81 | 4.0 | 22.6 |
| Comparative Example 6 | NPB | 5.2 | 18.1 |

As shown in Table 6, it could be seen that the organic electroluminescent devices in Examples 258 to 315 in which the compounds (Cpd1 to Cpd81) represented by Formula 1 according to the present disclosure were used as a material of hole transport layer exhibited better performances in terms of current efficiency and driving voltage than the organic electroluminescent device in Comparative Example 6 in which NPB in the related art was used.

[Example 316] Manufacture of Blue Organic Electroluminescent Device

Compound Cpd86 synthesized in Synthesis Example 59 was subjected to highly pure sublimation purification by a typically known method, and then a blue organic electroluminescent device was manufactured as follows.

A glass substrate thinly coated with indium tin oxide (ITO) having a thickness of 1,500 Å was ultrasonically washed with distilled water. When the washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic electroluminescent device was manufactured by laminating DS-205 (Manufactured by Doosan Corporation Electronics) (80 nm)/NPB (15 nm)/ADN+5% DS-405 (Manufactured by Doosan Corporation Electronics) (30 nm)/Compound Cpd86 (5 nm)/Alq$_3$ (25 nm)/LiF (1 nm)/Al (200 nm) in this order on the ITO transparent electrode prepared as described above.

[Example 317 to 355] Manufacture of Blue Organic Electroluminescent Device

A blue organic electroluminescent device was manufactured in the same manner as in Example 316, except that each compound shown in Table 7 was used instead of Compound Cpd86 used as a material of electron transport auxiliary layer in Example 316.

[Comparative Example 7] Manufacture of Blue Organic Electroluminescent Device

A blue organic electroluminescent device was manufactured in the same manner as in Example 316, except that Alq₃ being a material of electron transport layer was deposited to have a thickness of 30 nm instead of 25 nm without using Compound Cpd86 used as a material of electron transport auxiliary layer in Example 316.

[Comparative Example 8] Manufacture of Blue Organic Electroluminescent Device

An organic electroluminescent device was manufactured in the same manner as in Example 316, except that BCP was used instead of Compound Cpd86 used as a material of electron transport auxiliary layer in Example 316.

In this case, the structure of BCP used is as follows.

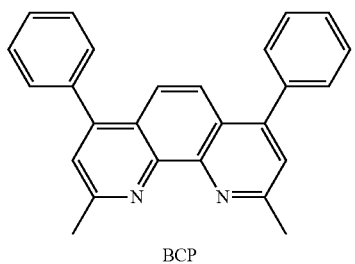

BCP

Evaluation Example 7

For each of the organic electroluminescent devices manufactured in Examples 316 to 355 and Comparative Examples 7 and 8, the driving voltage, current efficiency, light emitting wavelength, and lifetime (T97) thereof were measured at a current density of 10 mA/cm², and the results are shown in the following Table 7.

TABLE 7

| Sample | Electron transport auxiliary layer | Driving voltage (V) | Current efficiency (cd/A) | Light emitting peak (nm) | Lifetime (hr, $T_{97}$) |
|---|---|---|---|---|---|
| Example 316 | Cpd86 | 4.4 | 6.2 | 457 | 45 |
| Example 317 | Cpd87 | 4.1 | 6.3 | 458 | 62 |
| Example 318 | Cpd88 | 4.2 | 6.6 | 458 | 55 |
| Example 319 | Cpd89 | 4.5 | 6.2 | 458 | 75 |
| Example 320 | Cpd90 | 4.3 | 6.5 | 458 | 59 |
| Example 321 | Cpd91 | 4.3 | 6.1 | 458 | 78 |
| Example 322 | Cpd92 | 4.4 | 6.4 | 457 | 60 |
| Example 323 | Cpd93 | 4.1 | 6.2 | 458 | 64 |
| Example 324 | Cpd94 | 4.7 | 6.0 | 458 | 50 |
| Example 325 | Cpd95 | 4.7 | 6.4 | 457 | 85 |
| Example 326 | Cpd96 | 4.5 | 6.1 | 458 | 55 |
| Example 327 | Cpd97 | 4.4 | 6.0 | 458 | 75 |
| Example 328 | Cpd100 | 4.1 | 6.3 | 458 | 62 |
| Example 329 | Cpd101 | 4.2 | 6.6 | 458 | 55 |
| Example 330 | Cpd118 | 4.5 | 6.2 | 458 | 75 |
| Example 331 | Cpd119 | 4.3 | 6.4 | 457 | 60 |
| Example 332 | Cpd120 | 4.4 | 6.2 | 458 | 64 |
| Example 333 | Cpd121 | 4.1 | 6.0 | 458 | 50 |
| Example 334 | Cpd122 | 4.2 | 6.4 | 457 | 85 |
| Example 335 | Cpd123 | 4.4 | 6.1 | 458 | 55 |
| Example 336 | Cpd128 | 4.1 | 6.0 | 458 | 75 |
| Example 337 | Cpd129 | 4.7 | 6.3 | 458 | 62 |
| Example 338 | Cpd130 | 4.7 | 6.4 | 457 | 60 |
| Example 339 | Cpd131 | 4.5 | 6.2 | 458 | 64 |
| Example 340 | Cpd132 | 4.4 | 6.0 | 458 | 50 |
| Example 341 | Cpd133 | 4.1 | 6.4 | 457 | 85 |
| Example 342 | Cpd134 | 4.7 | 6.1 | 458 | 55 |
| Example 343 | Cpd135 | 4.7 | 6.0 | 458 | 75 |
| Example 344 | Cpd136 | 4.5 | 6.3 | 458 | 62 |
| Example 345 | Cpd137 | 4.4 | 6.6 | 458 | 55 |
| Example 346 | Cpd138 | 4.1 | 6.2 | 458 | 75 |
| Example 347 | Cpd139 | 4.2 | 6.4 | 457 | 60 |
| Example 348 | Cpd142 | 4.5 | 6.2 | 458 | 64 |
| Example 349 | Cpd143 | 4.3 | 6.0 | 458 | 50 |
| Example 350 | Cpd160 | 4.1 | 6.4 | 457 | 85 |
| Example 351 | Cpd161 | 4.2 | 6.1 | 458 | 55 |
| Example 352 | Cpd162 | 4.5 | 6.0 | 458 | 75 |
| Example 353 | Cpd163 | 4.3 | 6.3 | 458 | 62 |
| Example 354 | Cpd164 | 4.4 | 6.6 | 458 | 55 |
| Example 355 | Cpd165 | 4.1 | 6.2 | 458 | 75 |
| Comparative Example 7 | — | 4.7 | 5.6 | 458 | 32 |
| Comparative Example 8 | BCP | 5.3 | 5.9 | 458 | 28 |

As can be seen from Table 7, the blue organic electroluminescent devices in Examples 316 to 355, in which Compounds Cpd86 to 165 synthesized in Synthesis Examples 59 to 118 were used as a material of electron transport auxiliary layer, had a driving voltage which is similar to or slightly better than that of the blue organic electroluminescent device in Comparative Example 7 in which an electron transport auxiliary layer was not used, but had the significantly improved current efficiency and lifetime.

Further, the blue organic electroluminescent devices in Examples 316 to 355 had better driving voltage and current efficiency than those of the blue organic electroluminescent device in Comparative Example 8, in which the BCP in the related art was used as a material of electron transport auxiliary layer, and had the significantly improved lifetime.

Although the preferred exemplary embodiments of the present disclosure have been described above, the present disclosure is not limited thereto, and various modifications can be made and carried out within the scope of the claims and the detailed description of the invention, and also fall within the scope of the invention.

The invention claimed is:

1. A compound for an organic electroluminescence represented by any one selected from the following Formulae 3 to 5:

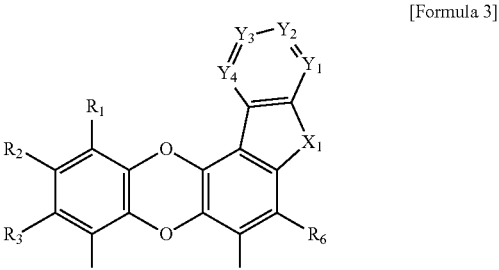

[Formula 3]

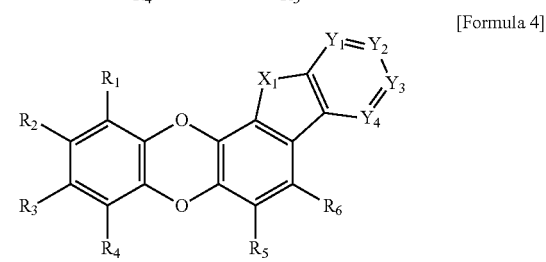

[Formula 4]

[Formula 5]

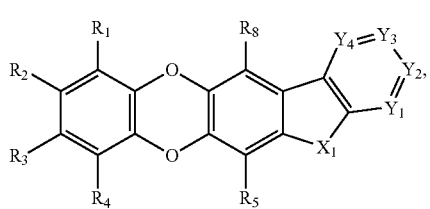

in Formulae 3 to 5, $X_1$ is selected from the group consisting of $N(Ar_1)$, O, S, $C(Ar_2)(Ar_3)$, and $Si(Ar_4)(Ar_5)$, with the proviso that, in Formula 3, $C(Ar_2)(Ar_3)$ is excluded from $X_1$, $Y_1$ to $Y_4$ are each independently N or $C(R_9)$, $Ar_1$ to $Ar_5$ are the same as or different from each other, and are each independently selected from the group consisting of a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combine with an adjacent group to form a fused ring, $R_1$ to $R_6$, $R_8$, and $R_9$ are the same as or different from each other, and are each independently selected from the group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or $R_1$ to $R_4$, and $R_9$ optionally combine with an adjacent group to form a fused ring, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ and $R_1$ to $R_6$, $R_8$, and $R_9$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and in this case, the substituent optionally combines with an adjacent group to form a fused ring, and when the substituent is present in plural numbers, the substituents are the same as or different from each other, with the proviso that where $X_1$ in the Formula 3 is $N(Ar_1)$, said $Ar_1$ is selected from the group consisting of a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combines with an adjacent group to form a fused ring, with the proviso that where $X_1$ in the Formula 5 is O, the case where all of $R_1$ to $R_5$, $R_8$ and $R_9$ are hydrogen is excluded.

2. The compound of claim 1, wherein the $Y_1$ to $Y_4$ are all $C(R_9)$, and a plurality of $C(R_9)$'s is the same as or different from each other, and $R_9$ is the same as that defined in claim 1.

3. The compound of claim 1, wherein at least one of the $Ar_1$ to $Ar_5$, $R_1$ to $R_6$, $R_5$, and $R_9$ is represented by the following Formula 6:

[Formula 6]

in Formula 6,

* is the location where the at least one of the $Ar_1$ to $Ar_5$, $R_1$ to $R_6$, $R_8$, and $R_9$ is bonded to the structure of Formula 3, 4, or 5, $L_1$ is a single bond or selected from the group consisting of a $C_6$ to $C_{18}$ arylene group and a heteroarylene group having 5 to 18 nuclear atoms, or optionally combines with an adjacent substituent to form a fused ring, and $R_a$ and $R_b$ are the same as or different from each other, and are each independently selected from the group consisting of a $C_1$ to $C_{40}$ alkyl group, a $C_6$ to $C_{60}$ aryl group, and a heteroaryl group having 5 to 60 nuclear atoms, or a substitution product represented by the following Formula 7 or 8, or optionally combine with an adjacent substituent to form a fused ring,

[Formula 7]

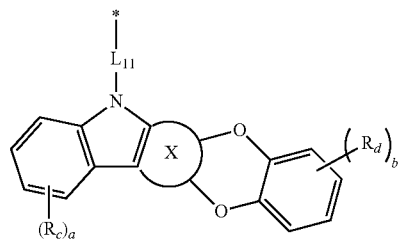

[Formula 8]

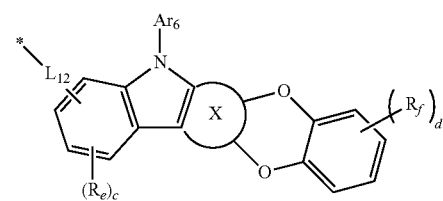

in Formulae 7 and 8,
* is the location where the $R_a$ and $R_b$ are bonded to the N atom of Formula 6,
X and Y are each a 6-membered aromatic ring,
$L_{11}$ and $L_{12}$ are each a single bond, or selected from the group consisting of a $C_6$ to $C_{18}$ arylene group and a heteroarylene group having 5 to 18 nuclear atoms,
$Ar_6$ is selected from the group consisting of a $C_6$ to $C_{18}$ aryl group and a heteroaryl group having 5 to 18 nuclear atoms,
a, b, and d are each an integer of 0 to 4, and the case where the a, b, and d are 0 means that hydrogen is not substituted with the substituent $R_c$, $R_d$, or $R_f$ and when the a, b, and d are each an integer of 1 to 3, $R_c$, $R_d$, or $R_f$ are each selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group,
c is an integer of 0 to 3, and the case where the c is 0 means that hydrogen is not substituted with the substituent $R_e$, and when the c is 1 to 3, $R_e$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group,
in this case, a plurality of $R_c$'s is the same as or different from each other, a plurality of $R_d$'s is the same as or different from each other, a plurality of $R_e$'s is the same as or different from each other, and a plurality of $R_f$'s is the same as or different from each other, and
the arylene group and the heteroarylene group of $L_1$ and the alkyl group, the aryl group, and the heteroaryl group of $R_a$ and $R_b$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

4. The compound of claim 1, wherein at least one of the $Ar_1$ to $Ar_5$, $R_1$ to $R_6$, $R_8$, and $R_9$ is represented by the following Formula 9:

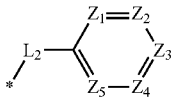
[Formula 9]

in Formula 9,
* is the location where the at least one of the $Ar_1$ to $Ar_5$, $R_1$ to $R_6$, $R_8$, and $R_9$ is bonded to the structure of Formula 3, 4, or 5,
$L_2$ is a single bond or selected from the group consisting of a $C_6$ to $C_{18}$ arylene group and a heteroarylene group having 5 to 18 nuclear atoms,
$Z_1$ to $Z_5$ are the same as or different from each other, and are each independently N or $C(R_{11})$, and in this case, at least one of the $Z_1$ to $Z_5$ is N, and when $C(R_{11})$ is present in plural numbers, a plurality of $C(R_{11})$'s is the same as or different from each other,
$R_{11}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, and
the arylene group and the heteroarylene group of $L_2$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{11}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

5. The compound of claim 1, wherein at least one of the $Ar_1$ to $Ar_5$, $R_1$ to $R_6$, $R_8$, and $R_9$ is selected from the group consisting of substituents represented by the following Formulae A-1 to A-15:

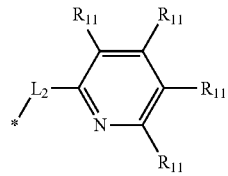
A-1 in Formulae A-1 to A-15,

* is the location where the at least one of the $Ar_1$ to $Ar_5$, $R_1$ to $R_6$, $R_8$, and $R_9$ is bonded to the structure of Formula 3, 4, or 5, $L_2$ is a single bond or selected from the group consisting of a $C_6$ to $C_{18}$ arylene group and a heteroarylene group having 5 to 18 nuclear atoms, when $R_{11}$ is present in plural numbers, a plurality of $R_{11}$'s is the same as or different from each other, $R_{11}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, n is an integer of 0 to 4, and when the n is an integer of 1 to 4, $R_{21}$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{11}$ and $R_{21}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

6. The compound of claim 1, wherein at least one of the $Ar_1$ to $Ar_5$, $R_1$ to $R_6$, $R_5$, and $R_9$ is represented by the following Formula 10 or 11:

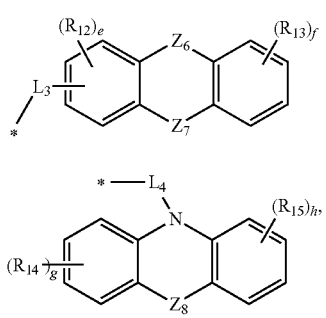

[Formula 10]

[Formula 11]

in Formulae 10 and 11,

* is the location where the at least one of the $Ar_1$ to $Ar_5$, $R_1$ to $R_6$, $R_8$, and $R_9$ is bonded to the structure of Formula 3, 4, or 5, $L_3$ and $L_4$ are each a single bond, or selected from the group consisting of a $C_6$ to $C_{18}$ arylene group and a heteroarylene group having 5 to 18 nuclear atoms, $Z_6$ to $Z_8$ are the same as or different from each other, and are each independently a single bond, or O, S, or $N(R_{16})$, provided that a case where $Z_6$ and $Z_7$ are all a single bond is excluded, in this case, when $N(R_{16})$ is present in plural numbers, a plurality of $N(R_{16})$'s is the same as or different from each other, $R_{16}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, e is an integer of 0 to 3, and when the e is 1 to 3, $R_{12}$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, f, g, and h are an integer of 0 to 4, and when the f, g, and h are each an integer of 1 to 4, $R_{13}$ to $R_{15}$ are selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, and in this case, the arylene group and the heteroarylene group of $L_3$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{12}$ to $R_{16}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

7. The compound of claim 1, wherein the $X_1$ is $N(Ar_1)$, and the $Ar_1$ is represented by the following Formula 12:

[Formula 12]

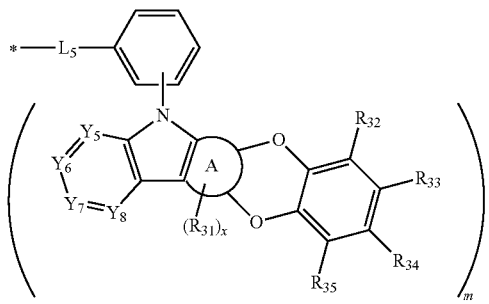

in Formula 12,

* is the location where the $Ar_1$ is bonded to the N atom of $N(Ar_1)$, $L_5$ is a single bond, or selected from the group consisting of a $C_6$ to $C_{60}$ aryl group, m is an integer of 1 and 2, A is a 6-membered aromatic ring, x is an integer of 0 to 2, and when the x is an integer of 1 and 2, $R_{31}$ are selected from the group consisting of deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combines with an adjacent group to form a fused ring, and in this case, when $R_{31}$ is present in plural numbers, a plurality of $R_{31}$'s is the same as or different from each other, $Y_5$ to $Y_8$ are each independently N or $C(R_{36})$, and in this case, when $C(R_{36})$ is present in plural numbers, a plurality of $C(R_{36})$'s is the same as or different from each other, $R_{32}$ to $R_{36}$ are the same as or different from each other, and are each independently selected from the group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combine with an adjacent group to form a fused ring, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_{31}$ to $R_{36}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, the substituent optionally combines with an adjacent group to form a fused ring, and in this case, when the substituent is present in plural numbers, the substituents are the same as or different from each other.

8. An organic electroluminescent device comprising:
an anode;
a cathode; and
one or more organic material layers interposed between the anode and the cathode,
wherein at least one of the organic material layers comprises the compound described in claim 1.

9. The organic electroluminescent device of claim 8, wherein the one or more organic material layers comprise a hole transport layer, a light emitting layer, and an electron transport layer, and the organic material layer comprising the compound is a light emitting layer or an electron transport layer.

10. The organic electroluminescent device of claim 8, wherein the one or more organic material layers comprise a hole transport layer, a light emitting auxiliary layer, a light emitting layer, and an electron transport layer, and the organic material layer comprising the compound is a light emitting auxiliary layer.

11. The organic electroluminescent device of claim 8, wherein the one or more organic material layers comprise a hole transport layer, a light emitting layer, an electron transport auxiliary layer, and an electron transport layer, and the organic material layer comprising the compound is an electron transport auxiliary layer.

12. The organic electroluminescent device of claim 8, wherein the $Y_1$ to $Y_4$ are all $C(R_9)$, and a plurality of $C(R_9)$'s is the same as or different from each other, and $R_9$ is the same as that defined in claim 8.

13. The organic electroluminescent device of claim 8, wherein at least one of the $Ar_1$ to $Ar_5$, $R_1$ to $R_6$, $R_8$, and $R_9$ is represented by the following Formula 6:

[Formula 6]

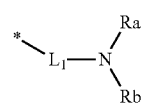

in Formula 6,

* is the location where the at least one of the $Ar_1$ to $Ar_5$, $R_1$ to $R_6$, $R_8$, and $R_9$ is bonded to the structure of Formula 3, 4, or 5, $L_1$ is a single bond or selected from the group consisting of a $C_6$ to $C_{18}$ arylene group and a heteroarylene group having 5 to 18 nuclear atoms, or optionally combines with an adjacent substituent to form a fused ring, and $R_a$ and $R_b$ are the same as or different from each other, and are each independently selected from the group consisting of a $C_1$ to $C_{40}$ alkyl group, a $C_6$ to $C_{60}$ aryl group, and a heteroaryl group having 5 to 60 nuclear atoms, or represented by the following Formula 7 or 8, or optionally combine with an adjacent substituent to form a fused ring,

[Formula 7]

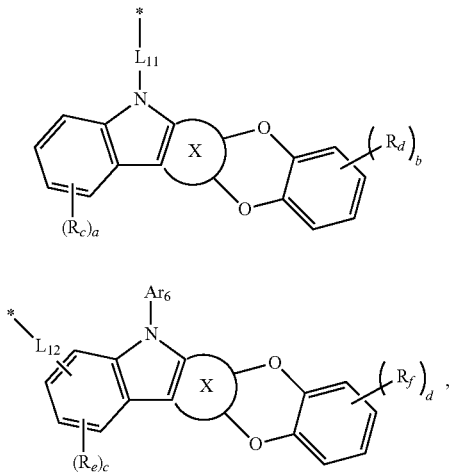

[Formula 8]

in Formulae 7 and 8,
* is the location where the Ra an Rb are bonded to the N atom of Formula 6,
X and Y are each a 6-membered aromatic ring,
$L_{11}$ and $L_{12}$ are each a single bond, or selected from the group consisting of a $C_6$ to $C_{18}$ arylene group and a heteroarylene group having 5 to 18 nuclear atoms,
$Ar_6$ is selected from the group consisting of a $C_6$ to $C_{18}$ aryl group and a heteroaryl group having 5 to 18 nuclear atoms,
a, b, and d are each an integer of 0 to 4, and the case where the a, b, and d are 0 means that hydrogen is not substituted with the substituent $R_c$, $R_d$, or $R_f$ and when the a, b, and d are each an integer of 1 to 3, $R_c$, $R_d$, or $R_f$ are each selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group,
c is an integer of 0 to 3, and the case where the c is 0 means that hydrogen is not substituted with the substituent $R_e$, and when the c is 1 to 3, $R_e$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group,
in this case, a plurality of $R_c$'s is the same as or different from each other, a plurality of $R_d$'s is the same as or different from each other, a plurality of $R_e$'s is the same as or different from each other, and a plurality of $R_f$'s is the same as or different from each other, and
the arylene group and the heteroarylene group of $L_1$ and the alkyl group, the aryl group, and the heteroaryl group of $R_a$ and $R_b$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

14. The organic electroluminescent device of claim 8, wherein at least one of the $Ar_1$ to $Ar_5$, $R_1$ to $R_6$, $R_8$, and $R_9$ is represented by the following Formula 9:

[Formula 9]

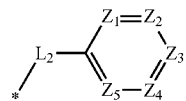

in Formula 9,
* is the location where the at least one of the $Ar_1$ to $Ar_5$, $R_1$ to $R_6$, $R_8$, and $R_9$ is bonded to the structure of Formula 3, 4, or 5,
$L_2$ is a single bond or selected from the group consisting of a $C_6$ to $C_{18}$ arylene group and a heteroarylene group having 5 to 18 nuclear atoms,
$Z_1$ to $Z_5$ are the same as or different from each other, and are each independently N or $C(R_{11})$, and in this case, at least one of the $Z_1$ to $Z_5$ is N, and when $C(R_{11})$ is present in plural numbers, a plurality of $C(R_{11})$'s is the same as or different from each other,
$R_{11}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, and
the arylene group and the heteroarylene group of $L_2$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{11}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

15. The organic electroluminescent device of claim 8, wherein at least one of the $Ar_1$ to $Ar_5$, $R_1$ to $R_6$, $R_8$, and $R_9$ is selected from the group consisting of substituents represented by the following Formulae A-1 to A-15:

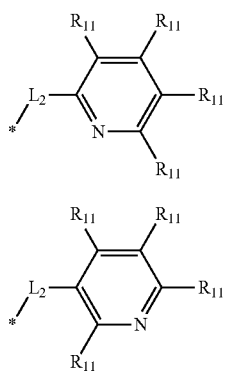

A-1

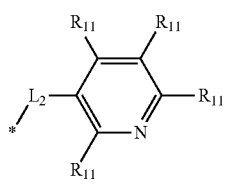

A-2

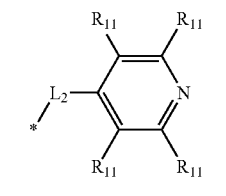

A-3

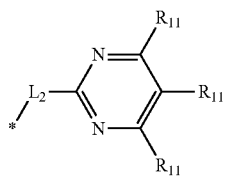

A-4

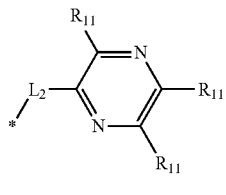

A-5

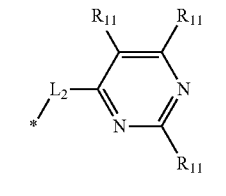

A-6

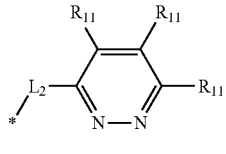

A-7

-continued

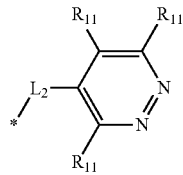

A-8

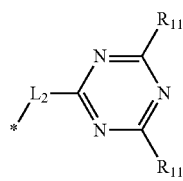

A-9

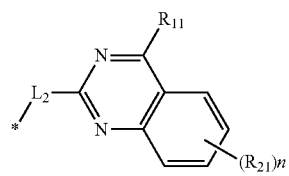

A-10

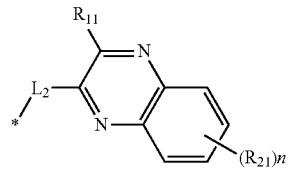

A-11

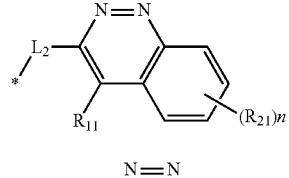

A-12

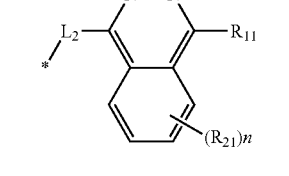

A-13

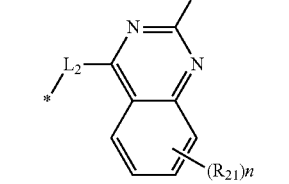

A-14

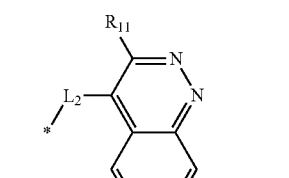

A-15 in Formulae A-1 to A-15,

* is the location where the at least one of the $Ar_1$ to $Ar_5$, $R_1$ to $R_6$, $R_8$, and $R_9$ is bonded to the structure of Formula 3, 4, or 5, $L_2$ is a single bond or selected from the group consisting of a $C_6$ to $C_{18}$ arylene group and a heteroarylene group having 5 to 18 nuclear atoms, when $R_{11}$ is present in plural numbers, a plurality of $R_{11}$'s is the same as or different from each other, $R_{11}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, n is an integer of 0 to 4, and when the n is an integer of 1 to 4, $R_{21}$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{11}$ and $R_{21}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

16. The organic electroluminescent device of claim 8, wherein at least one of the $Ar_1$ to $Ar_5$, $R_1$ to $R_6$, $R_8$, and $R_9$ is represented by the following Formula 10 or 11:

[Formula 10]

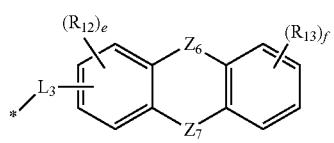

-continued

[Formula 11]

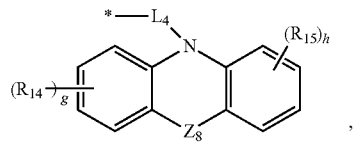

in Formulae 10 and 11,

* is the location where the at least one of the $Ar_1$ to $Ar_5$, $R_1$ to $R_6$, $R_8$, and $R_9$ is bonded to the structure of Formula 3, 4, or 5, $L_3$ and $L_4$ are each a single bond, or selected from the group consisting of a $C_6$ to $C_{18}$ arylene group and a heteroarylene group having 5 to 18 nuclear atoms, $Z_6$ to $Z_8$ are the same as or different from each other, and are each independently a single bond, or O, S, or $N(R_{16})$, provided that a case where $Z_6$ and $Z_7$ are all a single bond is excluded, in this case, when $N(R_{16})$ is present in plural numbers, a plurality of $N(R_{16})$'s is the same as or different from each other, $R_{16}$ is selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, or optionally combines with an adjacent group to form a fused ring, e is an integer of 0 to 3, and when the e is 1 to 3, $R_{12}$ is selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, f, g, and h are an integer of 0 to 4, and when the f, g, and h are each an integer of 1 to 4, $R_{13}$ to $R_{15}$ are selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_3$ to $C_{40}$ cycloalkyl group, a heterocycloalkyl group having 3 to 40 nuclear atoms, a $C_6$ to $C_{60}$ arylamine group, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group, and in this case, the arylene group and the heteroarylene group of $L_3$ and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphine group, the arylphosphine oxide group, and the arylsilyl group of $R_{12}$ to $R_{16}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_6$ to $C_{60}$ aryl group, a heteroaryl group having 5 to 60 nuclear atoms, a $C_6$ to $C_{60}$ aryloxy group, a $C_1$ to $C_{40}$ alkyloxy group, a $C_6$ to $C_{60}$ arylamine group, a $C_3$ to $C_{40}$ cycloalkyl group, a heterocycloalkyl group having 3 to 40 nuclear atoms, a $C_1$ to $C_{40}$ alkylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylsilyl group.

17. The organic electroluminescent device of claim 9, wherein the $X_1$ is $N(Ar_1)$, and the $Ar_1$ is represented by the following Formula 11:

[Formula 12]

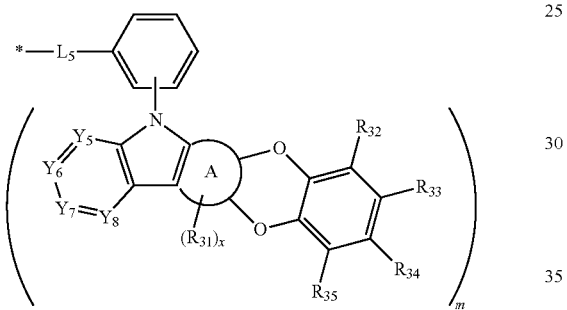

in Formula 12,

* is the location where the $Ar_1$ is bonded to the N atom of $N(Ar_1)$, $L_5$ is a single bond, or selected from the group consisting of a $C_6$ to $C_{60}$ aryl group, m is an integer of 1 and 2, A is a 6-membered aromatic ring, x is an integer of 0 to 2, and when the x is an integer of 1 and 2, $R_{31}$ are selected from the group consisting of deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combines with an adjacent group to form a fused ring, and in this case, when $R_{31}$ is present in plural numbers, a plurality of $R_{31}$'s is the same as or different from each other, $Y_5$ to $Y_8$ are each independently N or $C(R_{36})$, and in this case, when $C(R_{36})$ is present in plural numbers, a plurality of $C(R_{36})$'s is the same as or different from each other, $R_{32}$ to $R_{36}$ are the same as or different from each other, and are each independently selected from the group consisting of hydrogen, deuterium (D), halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, or optionally combine with an adjacent group to form a fused ring, and the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_{31}$ to $R_{36}$ are each independently unsubstituted or substituted with one or more substituents selected from the group consisting of deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, the substituent optionally combines with an adjacent group to form a fused ring, and in this case, when the substituent is present in plural numbers, the substituents are the same as or different from each other.

* * * * *